(12) United States Patent
Thon et al.

(10) Patent No.: US 12,060,576 B2
(45) Date of Patent: Aug. 13, 2024

(54) COMPOSITIONS AND METHODS FOR PRODUCING MEGAKARYOCYTES

(71) Applicant: Stellular Bio, Inc., Watertown, MA (US)

(72) Inventors: Jonathan Thon, Watertown, MA (US); Brad Dykstra, Watertown, MA (US)

(73) Assignee: Stellular Bio, Inc., Watertown, MA (US)

( * ) Notice: Subject to any disclaimer, the term of this patent is extended or adjusted under 35 U.S.C. 154(b) by 376 days.

(21) Appl. No.: 16/957,918

(22) PCT Filed: Jan. 5, 2019

(86) PCT No.: PCT/US2019/012437
§ 371 (c)(1),
(2) Date: Jun. 25, 2020

(87) PCT Pub. No.: WO2019/136318
PCT Pub. Date: Jul. 11, 2019

(65) Prior Publication Data
US 2021/0054336 A1    Feb. 25, 2021

Related U.S. Application Data

(60) Provisional application No. 62/614,117, filed on Jan. 5, 2018.

(51) Int. Cl.
*C12N 5/078* (2010.01)
*C12N 5/00* (2006.01)

(52) U.S. Cl.
CPC .......... *C12N 5/0644* (2013.01); *C12N 5/0075* (2013.01); *C12N 2501/115* (2013.01); *C12N 2501/125* (2013.01); *C12N 2501/145* (2013.01); *C12N 2501/155* (2013.01); *C12N 2501/165* (2013.01); *C12N 2501/2303* (2013.01); *C12N 2501/2306* (2013.01); *C12N 2501/2309* (2013.01); *C12N 2501/415* (2013.01); *C12N 2501/91* (2013.01); *C12N 2506/45* (2013.01); *C12N 2513/00* (2013.01); *C12N 2533/52* (2013.01)

(58) Field of Classification Search
CPC .................................................. C12N 5/0644
See application file for complete search history.

(56) References Cited

U.S. PATENT DOCUMENTS

| | | |
|---|---|---|
| 5,292,524 A | 3/1994 | Male et al. |
| 5,521,290 A | 5/1996 | Sivam et al. |
| 5,605,689 A | 2/1997 | Ammann |
| 5,733,254 A | 3/1998 | Jones et al. |
| 5,811,301 A | 9/1998 | Cameron |
| 6,225,119 B1 | 5/2001 | Qasba et al. |
| 6,589,759 B1 | 7/2003 | Loscalzo et al. |
| 6,723,497 B2 | 4/2004 | Wolkers et al. |
| 7,494,807 B2 | 2/2009 | Nakorn et al. |
| 7,794,707 B2 | 9/2010 | Penninger et al. |
| 7,939,063 B2 | 5/2011 | Cines et al. |
| 8,137,970 B2 | 3/2012 | Jhon et al. |
| 8,263,556 B2 | 9/2012 | Du Clos et al. |
| 8,372,642 B2 | 2/2013 | Rajesh et al. |
| 8,535,943 B2 | 9/2013 | Nakano et al. |
| 8,546,141 B2 | 10/2013 | Nakauchi et al. |
| 8,557,580 B2 | 10/2013 | Daigh et al. |
| 8,741,905 B2 | 6/2014 | Wagner et al. |
| 8,835,163 B2 | 9/2014 | Zhao et al. |
| 8,889,645 B2 | 11/2014 | Layzer et al. |
| 9,012,221 B2 | 4/2015 | Baruch et al. |
| 9,200,254 B2 | 12/2015 | Eto et al. |
| 9,259,443 B2 | 2/2016 | Poncz et al. |
| 9,574,178 B2 | 2/2017 | Mitchell et al. |
| 9,574,179 B2 | 2/2017 | Yu et al. |
| 9,738,906 B2 | 8/2017 | Eto et al. |
| 9,763,984 B2 | 9/2017 | Feng et al. |
| 9,795,965 B2 | 10/2017 | Italiano et al. |
| 9,803,164 B2 | 10/2017 | Mitchell |
| 9,909,102 B2 | 3/2018 | Baruch et al. |
| 9,982,034 B2 | 5/2018 | Wilcox et al. |
| 9,988,602 B2 | 6/2018 | Lanza et al. |
| 9,988,603 B2 | 6/2018 | Li et al. |

(Continued)

FOREIGN PATENT DOCUMENTS

| | | | |
|---|---|---|---|
| WO | 2006050330 A1 | 5/2006 | |
| WO | 2009002811 A1 | 12/2008 | |

(Continued)

OTHER PUBLICATIONS

Moreau, T., Evans, A. L., Vasquez, L., Tijssen, M. R., Yan, Y., Trotter, M. W., . . . & Ghevaert, C. (2016). Large-scale production of megakaryocytes from human pluripotent stem cells by chemically defined forward programming. Nature communications, 7(1), 11208. (Year: 2016).*

Feng, Q., Shabrani, N., Thon, J. N., Huo, H., Thiel, A., Machlus, K. R., . . . & Lanza, R. (2014). Scalable generation of universal platelets from human induced pluripotent stem cells. Stem cell reports, 3(5), 817-831. (Year: 2014).*

Wang, Y., Gao, Y., He, C., Ye, Z., Gerecht, S., & Cheng, L. (2016). Scalable production of human erythrocytes from induced pluripotent stem cells. BioRxiv, 050021. (Year: 2016).*

Galat, Y., Dambaeva, S., Elcheva, I., Khanolkar, A., Beaman, K., Iannaccone, P. M., & Galat, V. (2017). Cytokine-free directed differentiation of human pluripotent stem cells efficiently produces hemogenic endothelium with lymphoid potential. Stem cell research & therapy, 8(1), 1-11. (Year: 2017).*

Lam, A. T. L., Li, J., Chen, A. K. L., Birch, W. R., Reuveny, S., & Oh, S. K. W. (2015). Improved human pluripotent stem cell attachment and spreading on xeno-free laminin-521-coated microcarriers results in efficient growth in agitated cultures. BioResearch open access, 4(1), 242-257. (Year: 2015).*

(Continued)

*Primary Examiner* — Allison M Fox
*Assistant Examiner* — Jennifer S Spence
(74) *Attorney, Agent, or Firm* — Greenberg Traurig, LLP; Roman Fayerberg; George Banis

(57) ABSTRACT

Methods for producing megakaryocytic progenitors (preMKs) and megakaryocytes (MKs) from stem cells are provided. The present disclosure further provides compositions comprising preMKs and MKs and their lysates, and also methods of use of preMKs, MKs, their lysates and compositions thereof.

11 Claims, 54 Drawing Sheets

(56) References Cited

U.S. PATENT DOCUMENTS

| | | |
|---|---|---|
| 9,993,503 B2 | 6/2018 | Feng et al. |
| 10,100,282 B2 | 10/2018 | Rajesh et al. |
| 10,294,291 B2 | 5/2019 | Wilcox et al. |
| 10,307,462 B2 | 6/2019 | Ben Yehuda et al. |
| 10,426,799 B2 | 10/2019 | Feng et al. |
| 10,538,738 B2 | 1/2020 | Papoutsakis et al. |
| 10,604,738 B2 | 3/2020 | Pedersen et al. |
| 10,669,529 B2 | 6/2020 | Nakahata et al. |
| 10,729,730 B2 | 8/2020 | Zhao |
| 10,869,898 B2 | 12/2020 | Mata-Fink et al. |
| 10,894,065 B2 | 1/2021 | Feng et al. |
| 2002/0009500 A1 | 1/2002 | Wolkers et al. |
| 2002/0141992 A1 | 10/2002 | Nieswandt |
| 2002/0176804 A1 | 11/2002 | Strand et al. |
| 2005/0074426 A1 | 4/2005 | Corti et al. |
| 2005/0086710 A1 | 4/2005 | Peluso et al. |
| 2005/0252892 A1 | 11/2005 | Newman et al. |
| 2006/0099198 A1 | 5/2006 | Thomson et al. |
| 2006/0153813 A1 | 7/2006 | Quesenberry |
| 2007/0077246 A1 | 4/2007 | Koenig et al. |
| 2007/0077654 A1 | 4/2007 | Thomson et al. |
| 2007/0141656 A1 | 6/2007 | Mapes et al. |
| 2007/0243608 A1 | 10/2007 | Kyba et al. |
| 2008/0268535 A1 | 10/2008 | Jhon et al. |
| 2009/0232834 A1 | 9/2009 | Al-Harbi et al. |
| 2010/0063070 A1 | 3/2010 | Raud |
| 2010/0248361 A1 | 9/2010 | Lasky et al. |
| 2011/0039333 A1 | 2/2011 | Kahn et al. |
| 2011/0086424 A1 | 4/2011 | Lanza et al. |
| 2011/0243813 A1 | 10/2011 | Jackinsky et al. |
| 2012/0238020 A1 | 9/2012 | Mitchell et al. |
| 2012/0282228 A1 | 11/2012 | Bhasin |
| 2012/0301438 A1 | 11/2012 | Cheng |
| 2012/0315338 A1 | 12/2012 | Li et al. |
| 2013/0052662 A1 | 2/2013 | Barnes et al. |
| 2013/0061961 A1 | 3/2013 | Rapp et al. |
| 2013/0210141 A1 | 8/2013 | Rajesh et al. |
| 2014/0037600 A1 | 2/2014 | Yu et al. |
| 2014/0099359 A1 | 4/2014 | SenGupta et al. |
| 2014/0127815 A1 | 5/2014 | Eto et al. |
| 2014/0205582 A1 | 7/2014 | Karsunky et al. |
| 2014/0227780 A1 | 8/2014 | Nishino |
| 2014/0271590 A1 | 9/2014 | Feng et al. |
| 2014/0273211 A1 | 9/2014 | Slukvin et al. |
| 2015/0111296 A1 | 4/2015 | Pedersen et al. |
| 2015/0203819 A1 | 7/2015 | Murphy et al. |
| 2015/0275176 A1 | 10/2015 | Kobayashi et al. |
| 2015/0313944 A1 | 11/2015 | Feng et al. |
| 2015/0335682 A1 | 11/2015 | Murphy et al. |
| 2015/0361453 A1 | 12/2015 | Gresele et al. |
| 2016/0002586 A1 | 1/2016 | Mitchell |
| 2016/0002599 A1 | 1/2016 | Eto |
| 2016/0022736 A1 | 1/2016 | Feng et al. |
| 2016/0139124 A1 | 5/2016 | Newman et al. |
| 2016/0168540 A1 | 6/2016 | Hirata et al. |
| 2016/0177265 A1 | 6/2016 | Matsubara et al. |
| 2016/0209331 A1 | 7/2016 | Babic et al. |
| 2016/0272941 A1 | 9/2016 | Baruch et al. |
| 2016/0324897 A1 | 11/2016 | Ingber et al. |
| 2017/0121682 A1 | 5/2017 | Mitchell et al. |
| 2017/0130195 A1 | 5/2017 | Im et al. |
| 2017/0183616 A1 | 6/2017 | Thon et al. |
| 2018/0016597 A1 | 1/2018 | Eto et al. |
| 2018/0030415 A1 | 2/2018 | Nguyen et al. |
| 2018/0044634 A1 | 2/2018 | Dohda et al. |
| 2018/0055891 A1 | 5/2018 | Zhao |
| 2018/0135020 A1 | 5/2018 | Zhao |
| 2018/0161379 A1 | 6/2018 | Peterson et al. |
| 2018/0201889 A1 | 7/2018 | Sharei et al. |
| 2018/0237797 A1 | 8/2018 | Loh |
| 2018/0258395 A1 | 9/2018 | Shigemori et al. |
| 2018/0282697 A1 | 10/2018 | Hirose et al. |
| 2018/0318352 A1 | 11/2018 | Shigemori et al. |
| 2018/0318353 A1 | 11/2018 | Feng et al. |
| 2018/0334652 A1 | 11/2018 | Thon |
| 2019/0032015 A1 | 1/2019 | Eto et al. |
| 2019/0048317 A1 | 2/2019 | Eto et al. |
| 2019/0144823 A1 | 5/2019 | Slukvin et al. |
| 2019/0160103 A1 | 5/2019 | Garbin |
| 2019/0169566 A1 | 6/2019 | Gevaert et al. |
| 2019/0269732 A1 | 9/2019 | Matsubara et al. |
| 2019/0290686 A1 | 9/2019 | Wickham et al. |
| 2019/0290696 A1 | 9/2019 | DeMiroschedji |
| 2019/0376034 A1 | 12/2019 | Kahvejian et al. |
| 2020/0010809 A1 | 1/2020 | Wamhoff et al. |
| 2020/0017812 A1 | 1/2020 | Thon |
| 2020/0023011 A1 | 1/2020 | Feng et al. |
| 2020/0138868 A1 | 5/2020 | Thon et al. |
| 2020/0255804 A1 | 8/2020 | Pedersen et al. |
| 2021/0000750 A1 | 1/2021 | Gu et al. |
| 2021/0252070 A1 | 8/2021 | Thon et al. |
| 2021/0299180 A1 | 9/2021 | Hett et al. |
| 2021/0299181 A1 | 9/2021 | Hett et al. |
| 2022/0143095 A1 | 5/2022 | Hett et al. |
| 2023/0174939 A1 | 6/2023 | Falb et al. |
| 2023/0183646 A1 | 6/2023 | Peters et al. |

FOREIGN PATENT DOCUMENTS

| | | | |
|---|---|---|---|
| WO | 2009137629 A2 | 11/2009 | |
| WO | 2009139177 A1 | 11/2009 | |
| WO | 2010099539 A1 | 9/2010 | |
| WO | 2012112690 A2 | 8/2012 | |
| WO | 2014100779 A1 | 6/2014 | |
| WO | 2014138485 A1 | 9/2014 | |
| WO | 2015179301 A1 | 11/2015 | |
| WO | 2016141137 A1 | 9/2016 | |
| WO | 2016160860 A1 | 10/2016 | |
| WO | 2017013262 A1 | 1/2017 | |
| WO | WO-2017070337 A1 * | 4/2017 | ............ C12N 15/85 |
| WO | 2017211906 A1 | 12/2017 | |
| WO | 2018053010 A1 | 3/2018 | |
| WO | 2018164040 A1 | 9/2018 | |
| WO | 2018165308 A1 | 9/2018 | |
| WO | 2008121027 A1 | 10/2018 | |
| WO | 2018227286 A1 | 12/2018 | |
| WO | 2019009364 A1 | 1/2019 | |
| WO | 2019028192 A1 | 2/2019 | |
| WO | 2019089826 A1 | 5/2019 | |
| WO | 2019094614 A1 | 5/2019 | |
| WO | 2019126818 A1 | 6/2019 | |
| WO | 2019136318 A2 | 7/2019 | |
| WO | 2019161192 A1 | 8/2019 | |
| WO | 2020006539 A1 | 1/2020 | |
| WO | 2020014175 A1 | 1/2020 | |
| WO | 2021195496 A2 | 9/2021 | |
| WO | 2021231990 A2 | 11/2021 | |

OTHER PUBLICATIONS

Preliminary Rejection Report (South Korea); Dated: Sep. 22, 2022.
Title: "Progress and challenges in large-scale expansion of human pluripotent stem cells"; By: Christina Kropp; Dated: Oct. 25, 2016.
Title: "Application of small molecule CHIR99021 leads to the loss of hemangioblast progenitor and increased hematopoiesis of human pluripotent stem cells"; By: Yekaterina Galat; Date: May 29, 2018.
Baigger et al., "Towards the Manufacture of Megakaryocytes and Platelets for Clinical Application" Transfus. Med. Hemother. vol. 44, pp. 165-173, 2017.
Borger et al., "Generation of HLA-Universal iPSC-Derived Megakaryocytes and Platelets for Survival under Refractoriness Conditions" Mol. Med. vol. 22, pp. 274-285, 2016.
Hirata et al., "Selective Inhibition of ADAM17 Efficiently Mediates Glycoprotein Ib[alpha] Retention During EXPERTECH Vivo Generation of Human Induced Pluripotent Stem Cell-Derived Platelets" Stem Cells Translational Medicine, vol. 6, No. 3, pp. 720-730, Mar. 1, 2017.
Kronke et al., "Lenalidomide Induces Ubiquitination and Degradation of CK1a in del(5q) MDS" Nature, vol. 523, No. 7559, pp. 183-188, Jul. 1, 2015.

(56) References Cited

OTHER PUBLICATIONS

Lambert et al., "Challenges and Promises for the Development of Donor-Independent Platelet Transfusions" Blood, American Society of Hematology, US, vol. 121, No. 17, pp. 3319-3324, Jan. 15, 2013.
Liu et al., "Efficient Generation of Megakaryocytes from Human Induced Pluripotent Stem Cells Using Food and Drug Administration-Approved Pharmacological Reagents" Stem Cells Translational Medicine, vol. 4, No. 4, pp. 309-319, Apr. 1, 2015.
Sarkar et al., "Drug Delivery Using Platelet Cancer Cell Interaction" Pharmaceutical Research, vol. 30, No. 11, pp. 2785-2794, Jun. 6, 2013.
Solomon et al., "Current Perspectives on the Use of Ancillary Materials for the Manufacture of Cellular Therapies" Cytotherapy, vol. 18, Iss. 1, pp. 1-12, Jan. 31, 2016.
Sullivan et al., "High-Level Transgene Expression in Induced Pluripotent Stem Cell-Derived Megakaryocytes: Correction of Glanzmann Thrombasthenia" Blood, vol. 123, No. 5, pp. 753-757, 2014.
Dege et al., "Directed Differentiation of Primitive and Definitive Hematopoietic Progenitors from Human Pluripotent Stem Cells", Journal of Visualized Experiments, Nov. 1, 2017, vol. 129, e55196.
Galat et al., "Cytokine-free directed differentiation of human pluripotent stem cells efficiently produces hemogenic endothelium with lymphoid potential", Stem Cell Research & Therapy, vol. 8, No. 1, Mar. 17, 2017.
Wang et al., "Scalable Production of Human Erythrocytes from Induced Pluripotent Stem Cells", bioRxiv, Apr. 23, 2016.
International Search Report in International Patent Application No. PCT/US2019/012437 mailed Apr. 23, 2019.
Fujimoto et al., "Production of functional platelets by differentiated embryonic stem (ES) cells in vitro," Blood, Dec. 1, 2003, vol. 102, No. 12, pp. 4044-4051.
Hong et al., "Transfection of Human Platelets with Short Interfering RNA," Clinical and Translational Science, Jun. 27, 2011, vol. 4, Iss. 3, pp. 180-182.
Khan, Kishwar Hayat, "Gene Transfer Technologies and their Applications: Roles in Human Diseases," Asian Journal of Experimental Biological Science, 2010, vol. 1, Iss. 1, pp. 208-218.
Mangin et al., "Thrombin overcomes the thrombosis defect associated with platelet GPVI/FcRy deficiency," Blood, Jun. 1, 2006, vol. 107, No. 11, pp. 4346-4353.
Ohmori et al., "Efficient expression of a transgene in platelets using simian immunodeficiency virus-based vector harboring glycoprotein Ibα promoter: in vivo model for platelet-targeting gene therapy," The FASEB Journal, 2006, vol. 20, pp. E769-E779.
Pascreau et al., "Elevated thrombin generation in patients with congenital disorder of glycosylation and combined coagulation factor deficiencies," Journal of Thrombosis and Haemostasis, Jul. 4, 2019, vol. 17, Iss. 11, pp. 1798-1807.
Tozawa et al., "Megakaryocytes and platelets from a novel human adipose tissue-derived mesenchymal stem cell line," Blood, Feb. 14, 2019, vol. 133, No. 7, pp. 633-643.
Wells, D. J., "Gene Therapy Progress and Prospects: Electroporation and other physical methods," Gene Therapy, Aug. 5, 2004, vol. 11, pp. 1363-1369.
Wilhelm et al., "Analysis of nanoparticle delivery to tumours," Nature Reviews Materials, May 2016, vol. 1, Article No. 16014, pp. 1-12.
Andrade et al., "Biotech-Educated Platelets: Beyond Tissue Regeneration 2.0," International Journal of Molecular Sciences, vol. 21, Iss. 17, Article No. 6061, pp. 1-14, Aug. 23, 2020.
Escolar et al., "Modifications in Accessibility of Membrane Glycoproteins, Binding of Specific Ligands and Coagulation Factor V During the Activation of Platelets in Blood Emerging from Bleeding Time Wounds", American Journal of Hematology, vol. 60, pp. 260-267 (1999).
Fujiyama et al., "Development of an Ex Vivo Xenogeneic Bone Environment Producing Human Platelet-Like Cells," PLoS ONE, vol. 15, No. 4, e0230507, pp. 1-12, Apr. 7, 2020.
Kailashiya et al., "Engineered Human Platelet-Derived Microparticles as Natural Vectors for Targeted Drug Delivery" Oncotarget, vol. 10, No. 56, pp. 5835-5846 (2019).
Pick et al., "Generation of Megakaryocytic Progenitors from Human Embryonic Stem Cells in a Feeder and Serum-Free Medium" PLOS One, vol. 8, No. 2, pp. 1-11, Feb. 2013.
Thon et al., "Platelet Bioreactor: Accelerated Evolution of Design and Manufacture" Platelets, vol. 28, No. 5, pp. 472-477.
Zaldivia et al., "Platelet-Derived Microvesicles in Cardiovascular Diseases" Frontiers in Cardiovascular Medicine, vol. 4, Article 74, pp. 1-13, Nov. 2017.
Amit et al., "Dynamic Suspension Culture for Scalable Expansion of Undifferentiated Human Pluripotent Stem Cells," Nature Protocols, vol. 6, No. 5., pp. 572-579, Apr. 2011.
Everts, "Autologous Platelet-Rich Plasma and Mesenchymal Stem Cells for the Treatment of Chronic Wounds" Wound Healing Current Perspectives, pp. 1-32 Nov. 5, 2018.
MaCauley et al., "Canonical Wnt Signaling in Megakaryocytes Regulates Proplatelet Formation," Blood, vol. 121, No. 1, pp. 188-196, Jan. 3, 2013.
Mariani et al., "Platelet Concentrates in Musculoskeletal Medicine," International Journal of Molecular Sciences, vol. 21, No. 4, pp. 1-43, Feb. 16, 2020.
Eisenstein et al., "Nature Biotechnology's Academic Spinouts of 2019", Nature Biotechnology, vol. 38, pp. 546-558, May 2020.
Aatonen et al., "Isolation and Characterization of Platelet-Derived Extracellular Vesicles", Journal of Extracellular Vesicles, vol. 3, No. 1, p. 24692, Jan. 1, 2013.
Alshehri et al., "Fibrin Activates GPVI in Human and Mouse Platelets", Blood, vol. 126, No. 13, pp. 1601-1608, Sep. 24, 2015.
Hansen et al., "Human-Induced Pluripotent Stem Cell-Derived Blood Products: State of the Art and Future Directions", FEBS Letters, vol. 593, pp. 3288-3303, 2019.
Ito et al., "Turbulence Activates Platelet Biogenesis to Enable Clinical Scale Ex Vivo Production", Cell, vol. 174, No. 3, pp. 636-648, Jul. 26, 2018.
Orban et al., "Functional Comparison of Induced Pluripotent Stem Cell- and Blood-Derived GPIIbIIIa Deficient Platelets", PLoS One, vol. 20, No. 1, p. e0115978, Jan. 21, 2015.
Sullenbarger et al., "Prolonged Continuos in Vitro Human Platelet Production Using Three-Dimensional Scaffolds", Experimental Hematology, vol. 37, No. 1, pp. 101-110, Jan. 1, 2009.
Baigger et al., "Large-Scale Production of Induced Pluripotent Stem Cells-Derived Megakaryocytes in Bioreactors" Transfus. Med. Hemother. vol. 44, Supplement 1, pp. 5-6, Article No. V03-2, 2017.

* cited by examiner

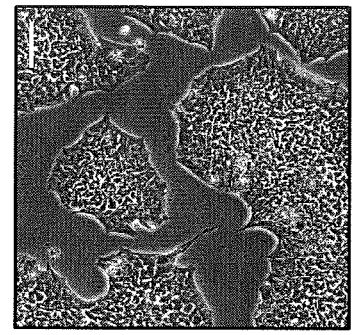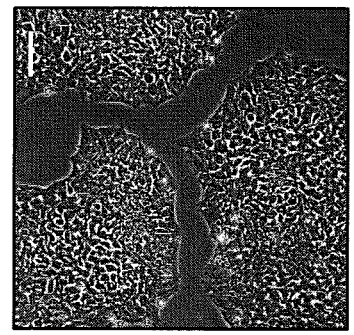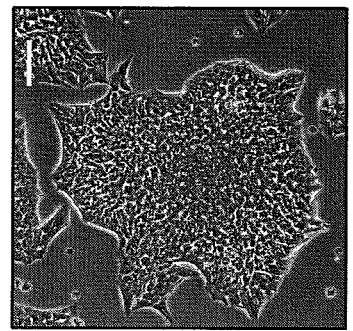
FIG. 3A
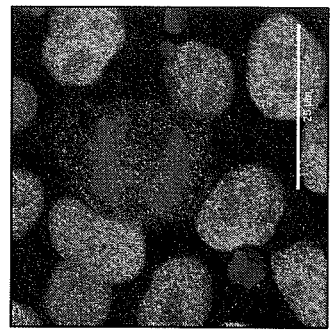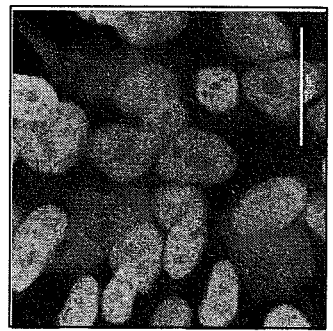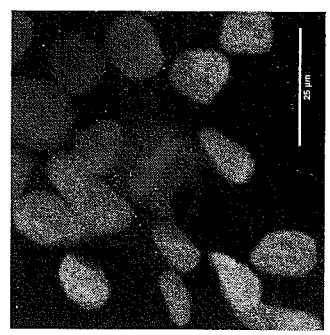
Oct4
Nanog
Nuclei
FIG. 3B FIG. 8A PBG1
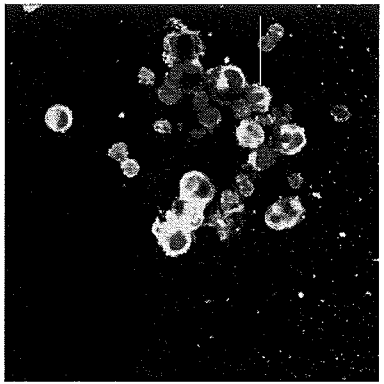 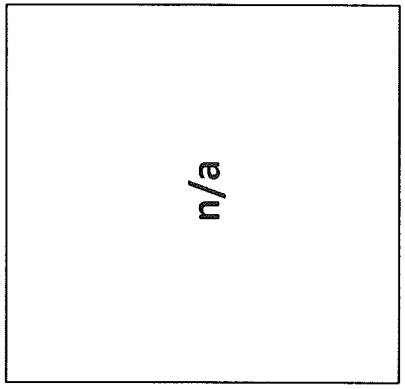
FIG. 8B PBG2
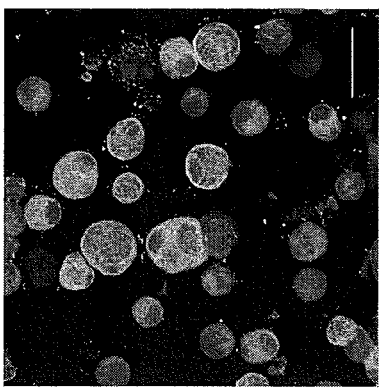 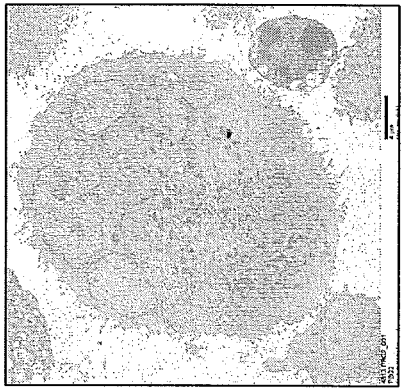
FIG. 8C PBG3
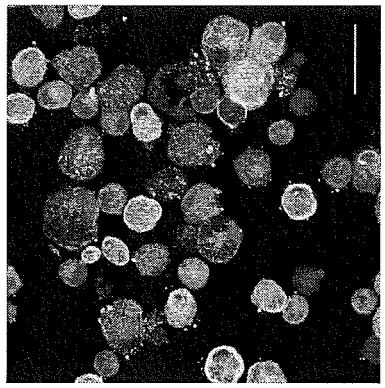 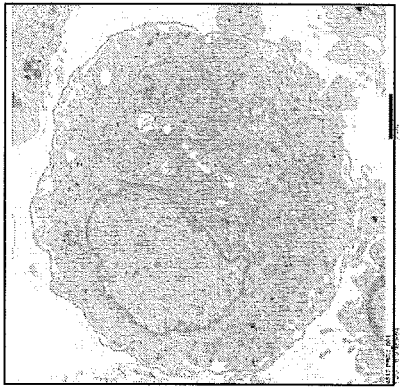

Essential 8
(Gibco A15170-01)

StemFlex
(Gibco A33494-01)

NutriStem hPSC XF
(Biological Industries)

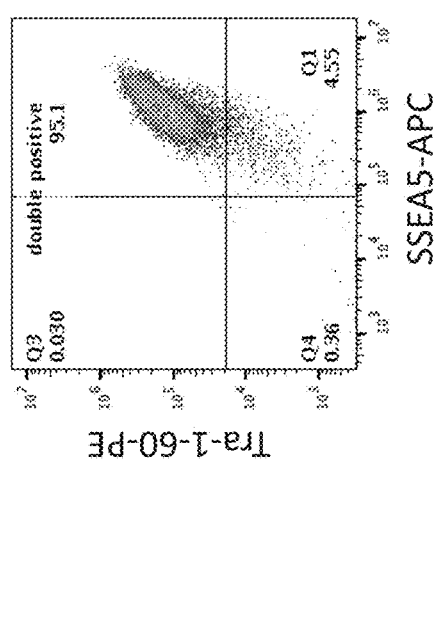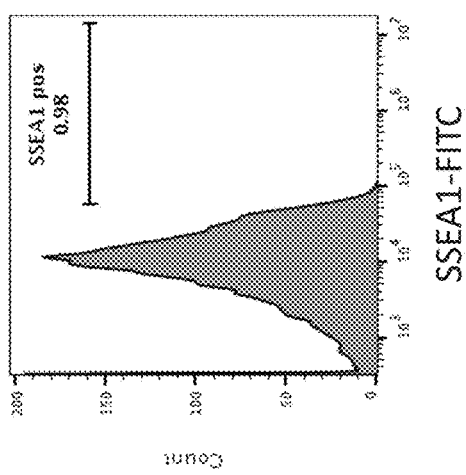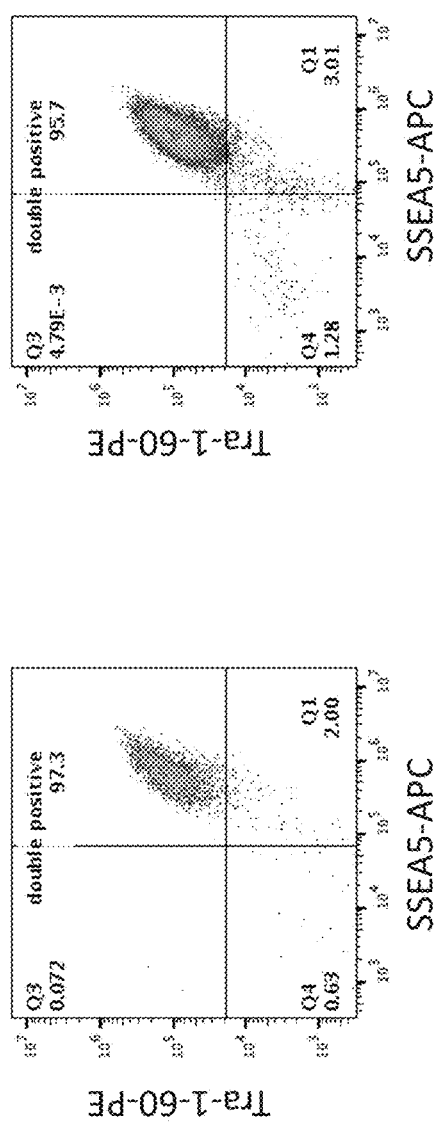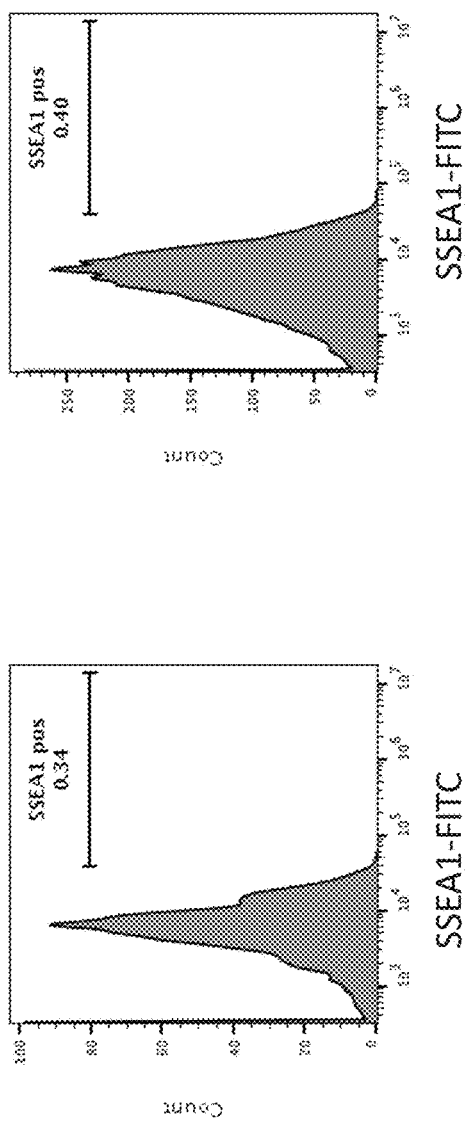
FIG. 10A Essential 8 (Gibco A15170-01)
FIG. 10B StemFlex (Gibco A33494-01)
FIG. 10C NutriStem hPSC XF (Biological Industries)

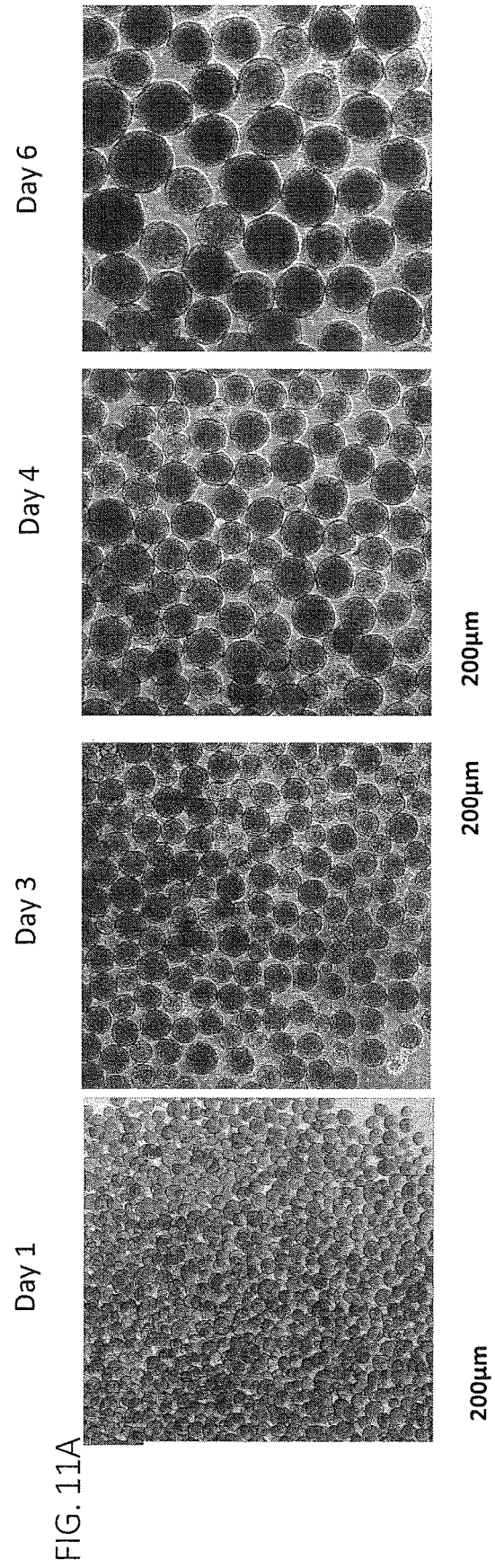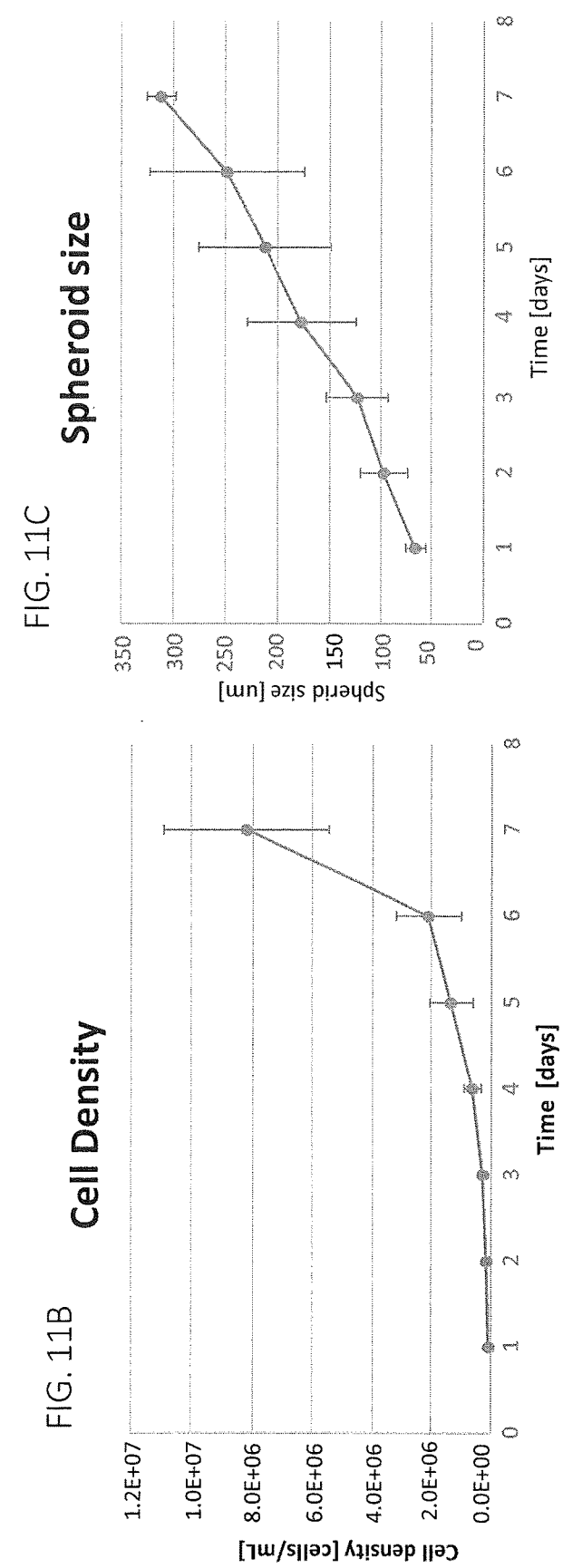
FIG. 11A
FIG. 11B
FIG. 11C

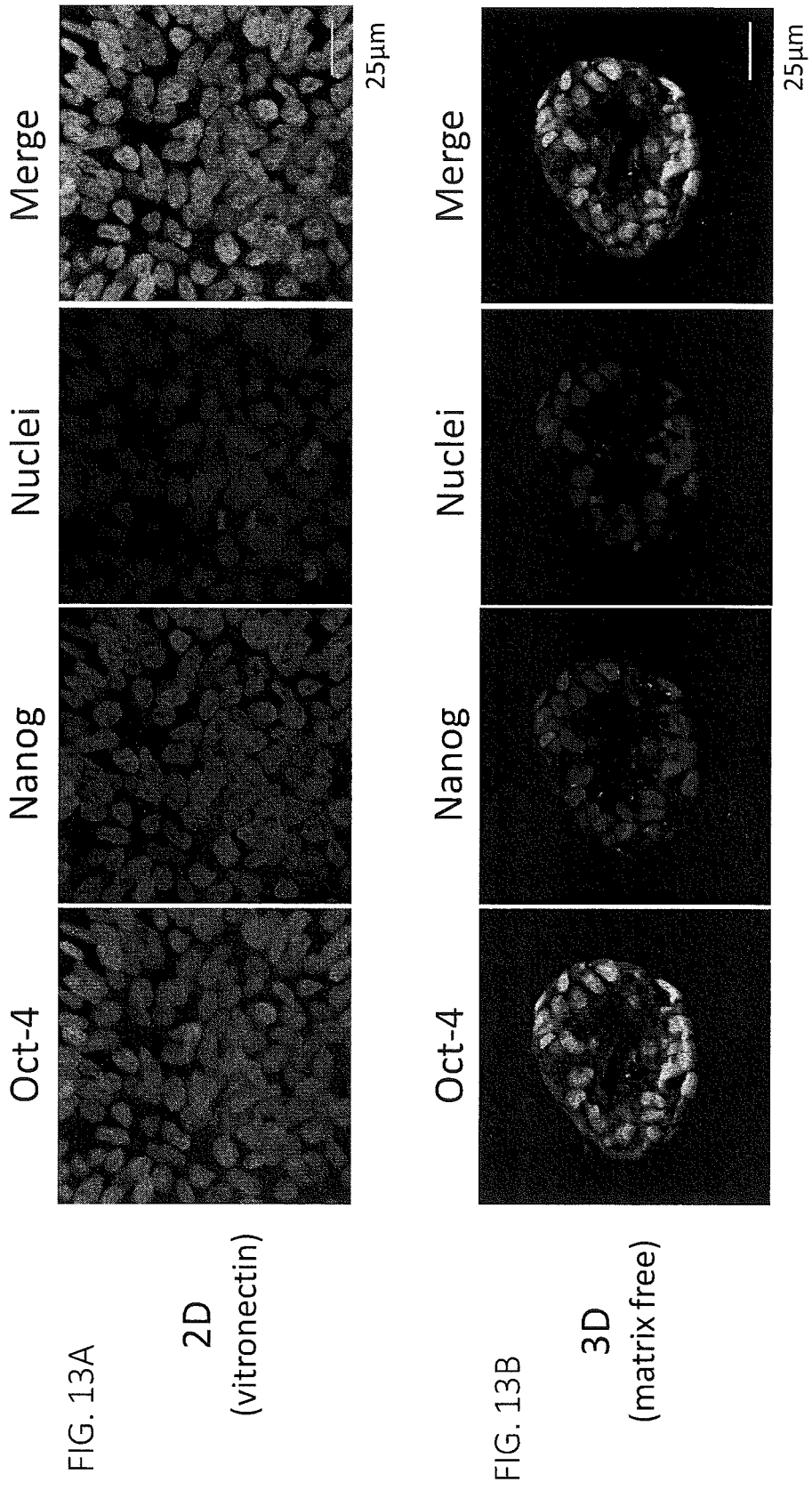
FIG. 13A 2D (vitronectin)
FIG. 13B 3D (matrix free)

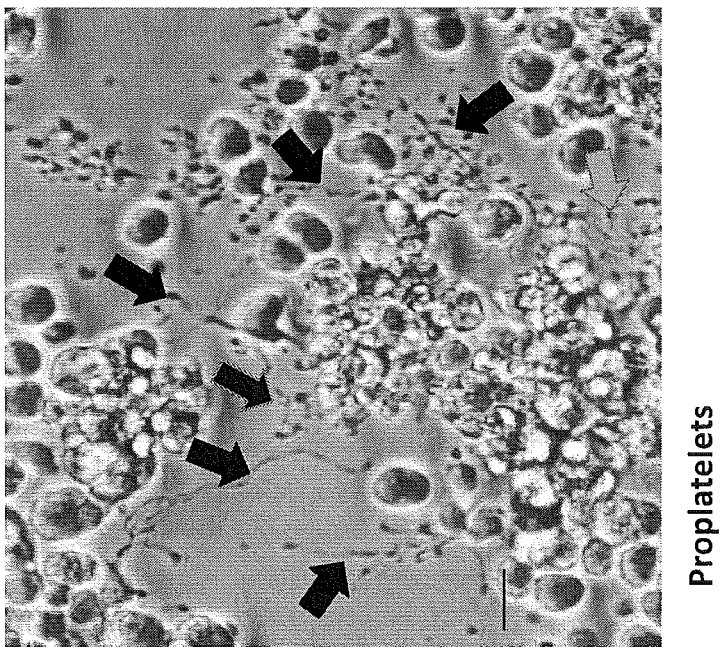
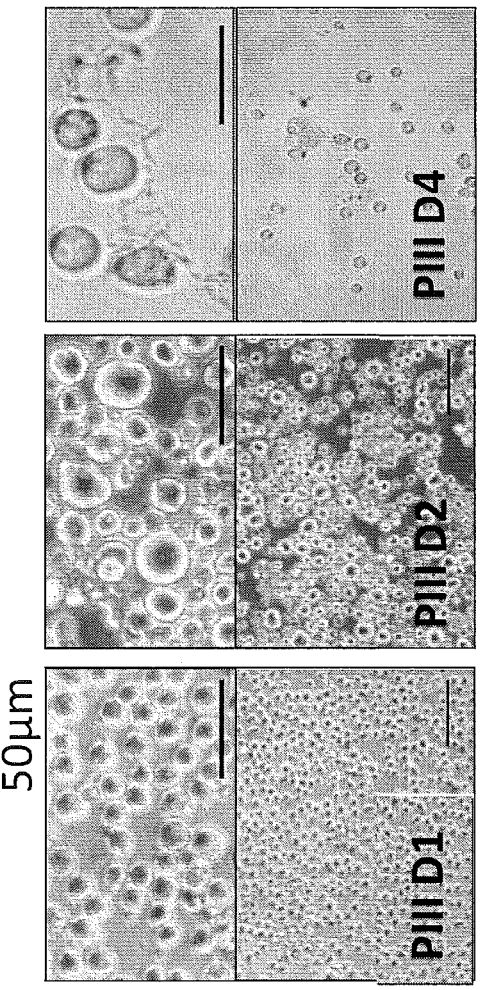

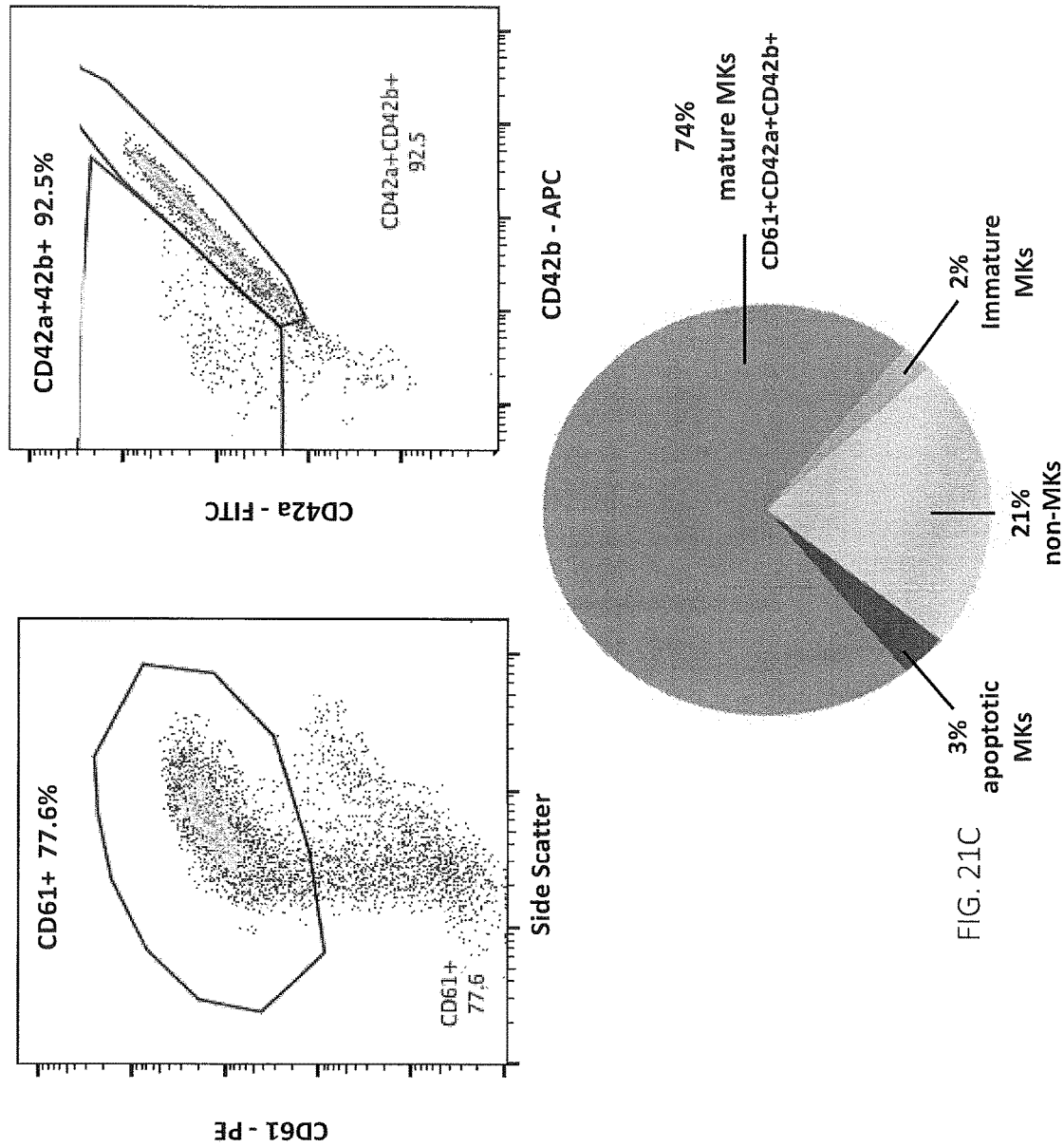

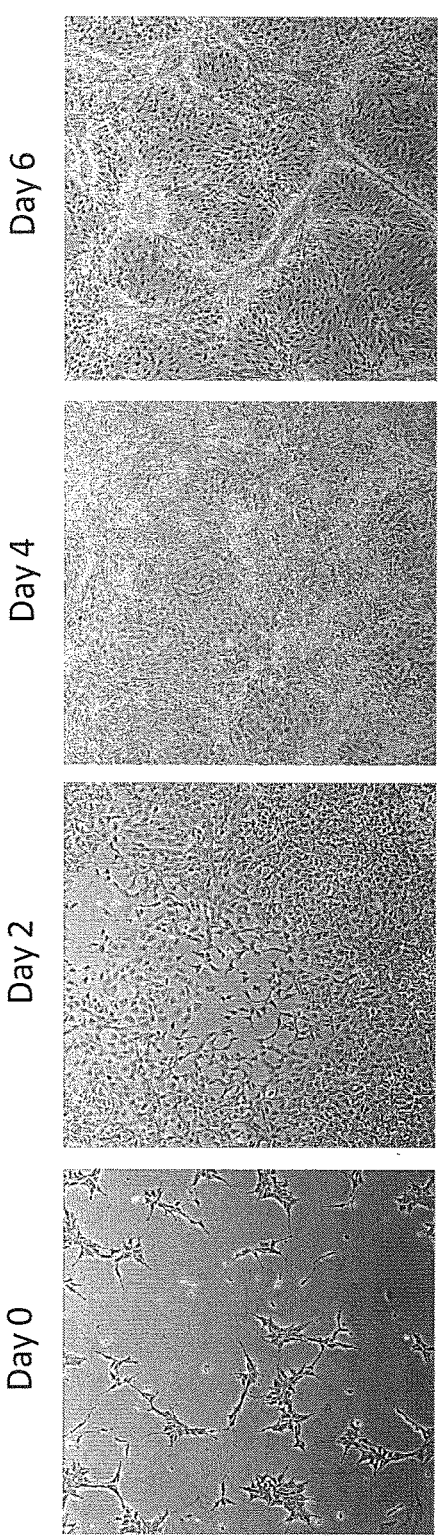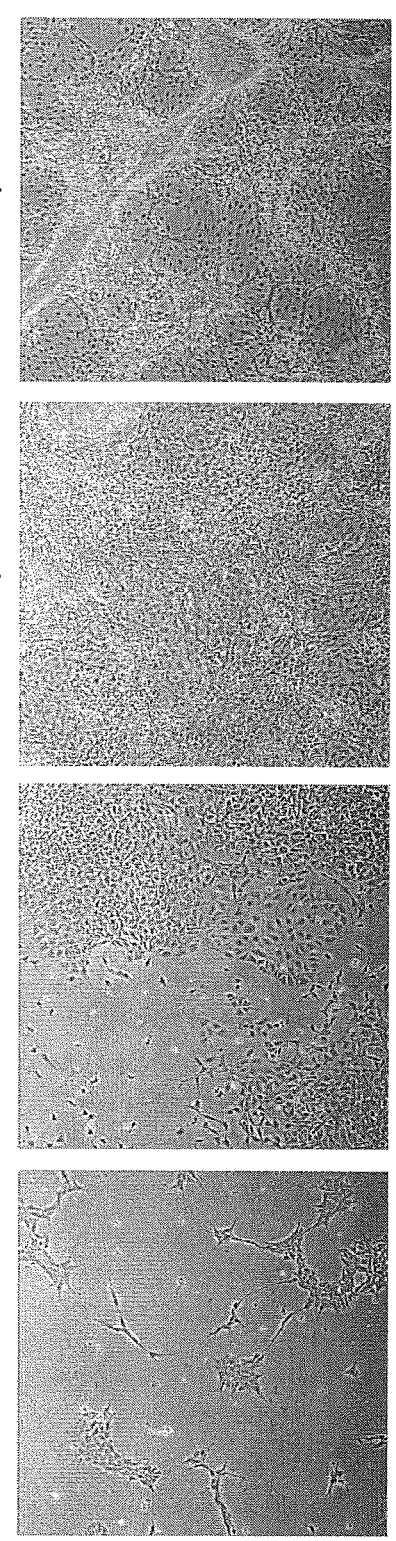

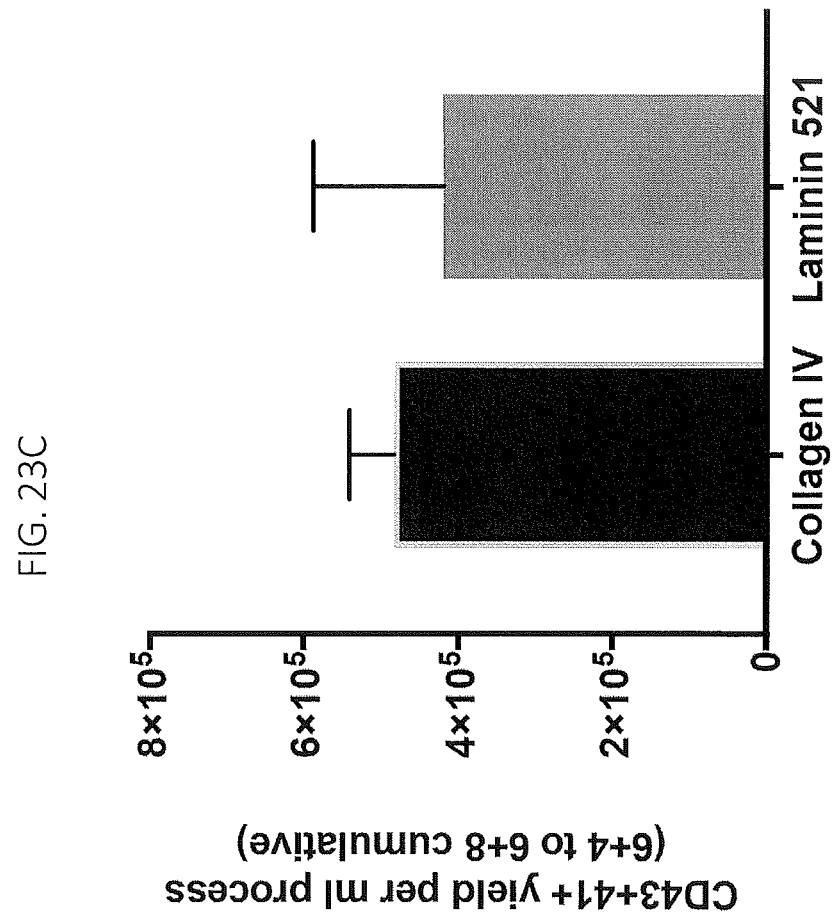

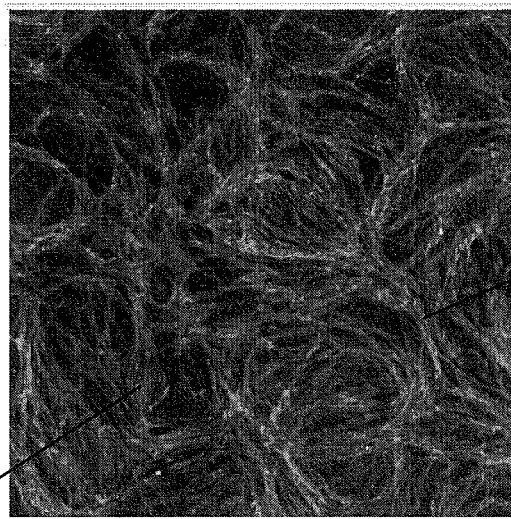
FIG. 26C CHIR99021
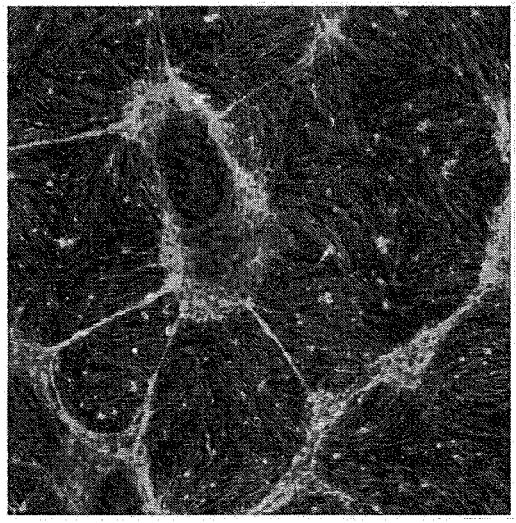
FIG. 26B CHIR98014
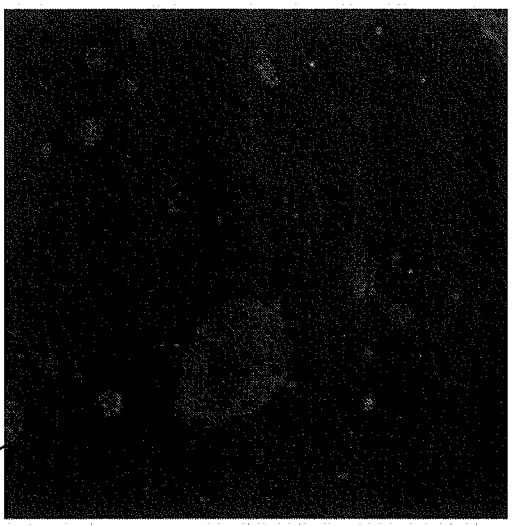
FIG. 26A Control
Nuclei CD34 CD31
Phase I – day 6

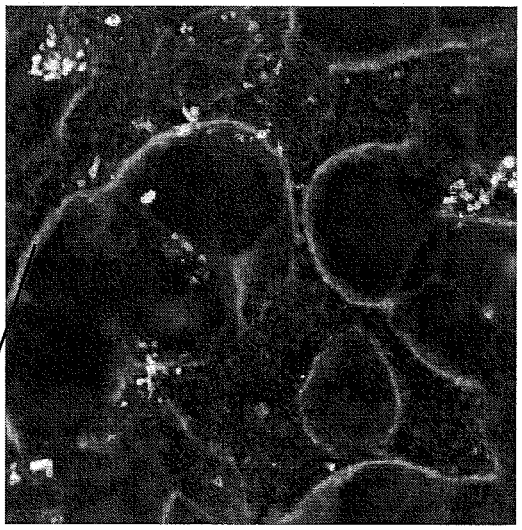
FIG. 27A Control
FIG. 27B CHIR98014
Nuclei CD41 CD43 CD14
Phase II – day 6+4

FIG 29

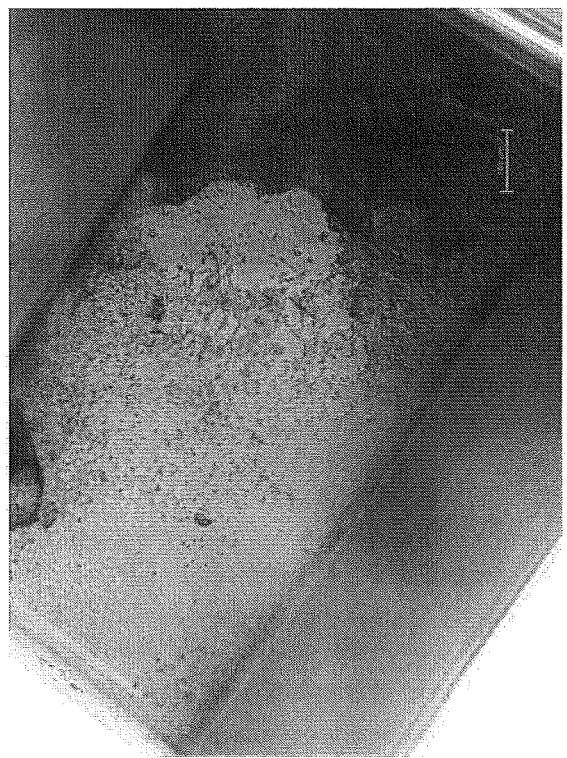
FIG. 30

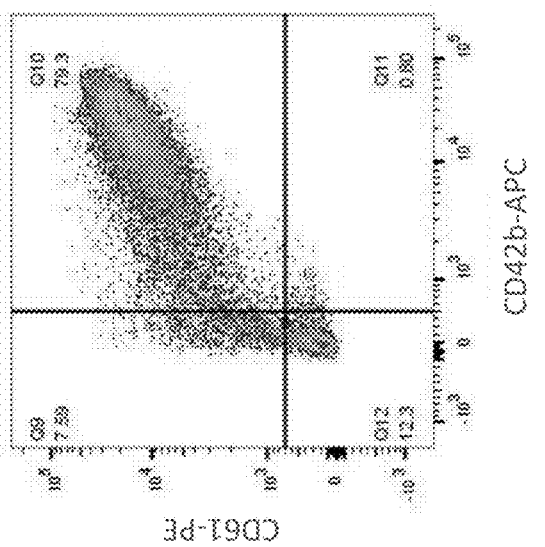
FIG. 31C Day 6+3+3 (Phase III)
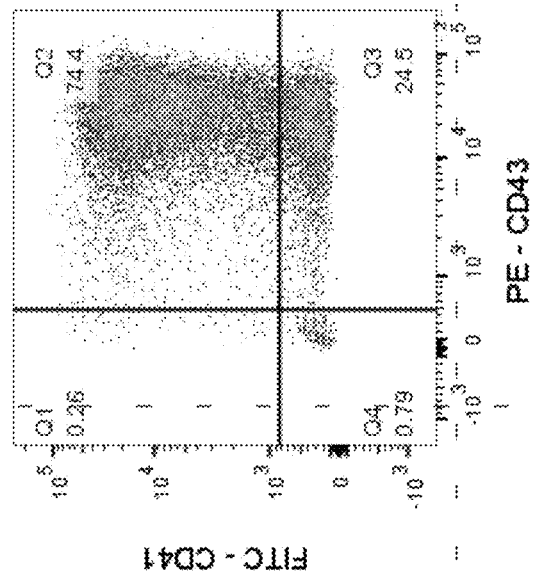
FIG. 31B Day 6+2 (Phase II)
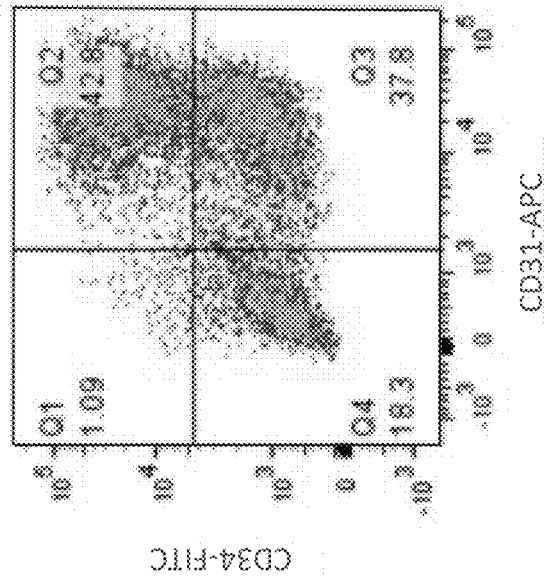
FIG. 31A Day 6 (Phase I)

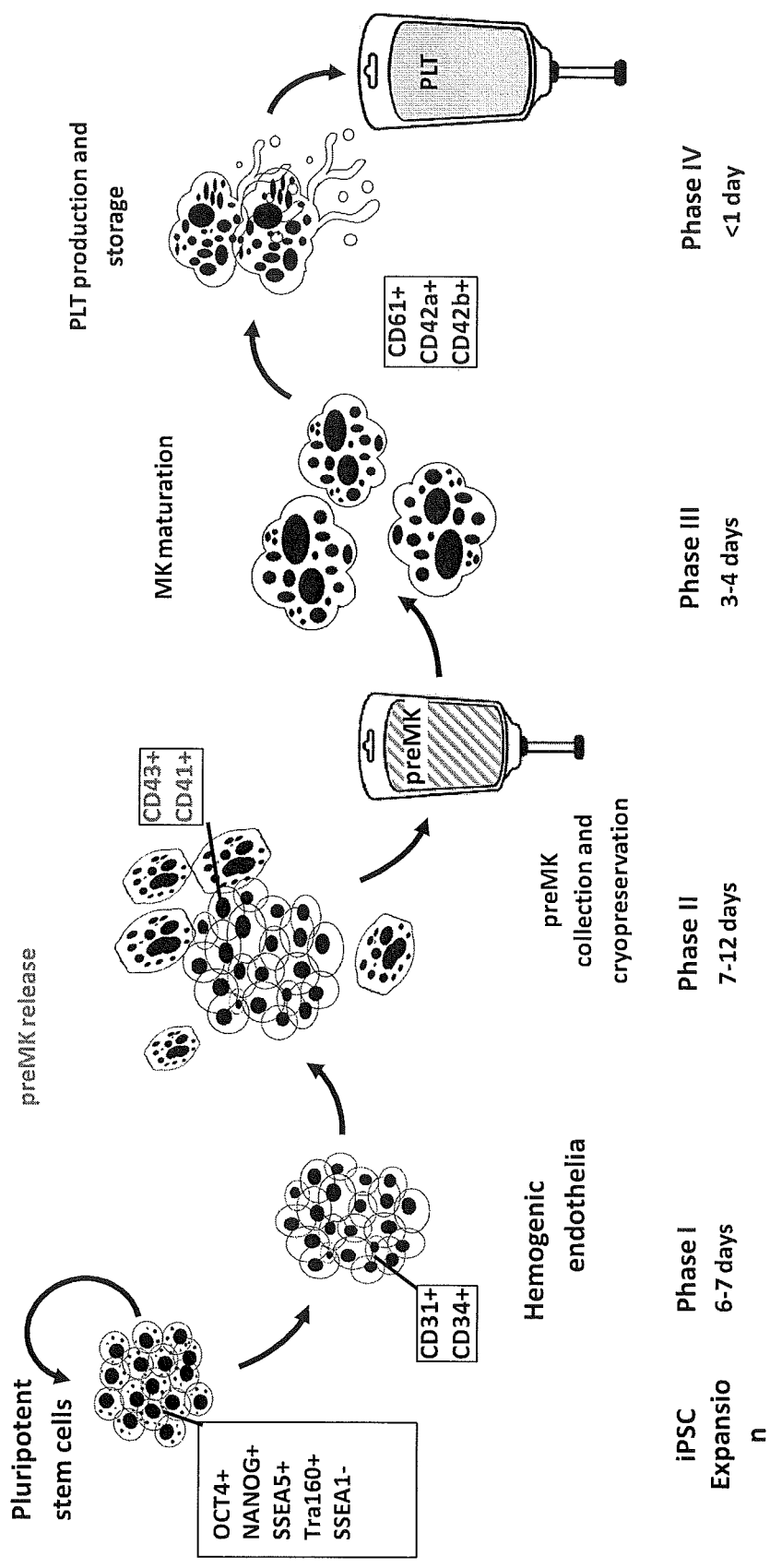

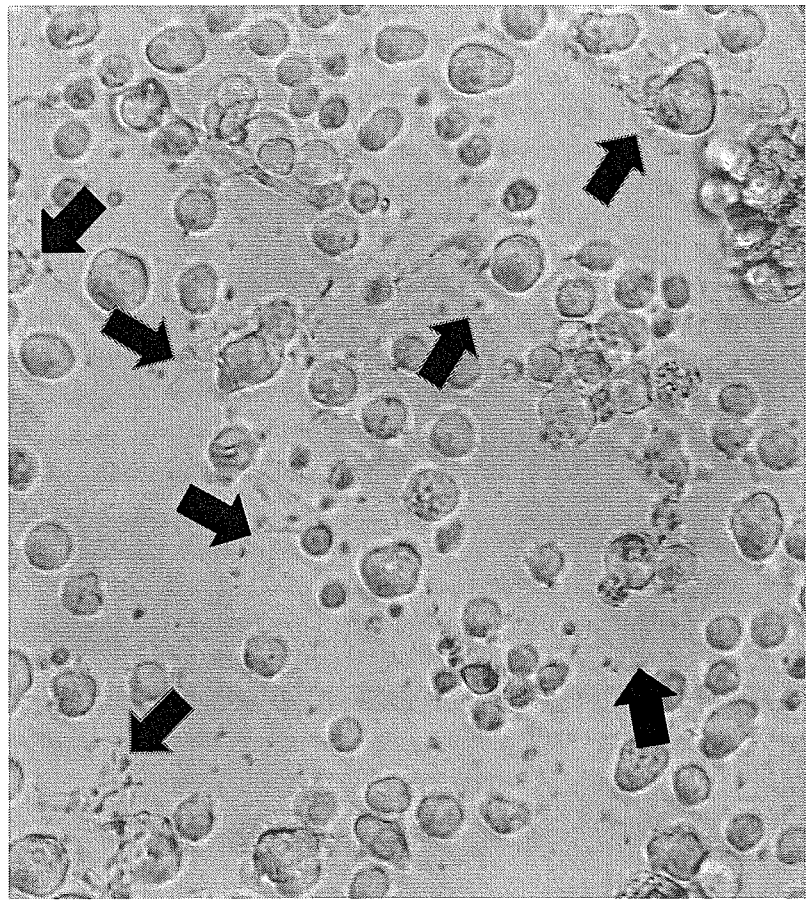
FIG 36 Proplatelets

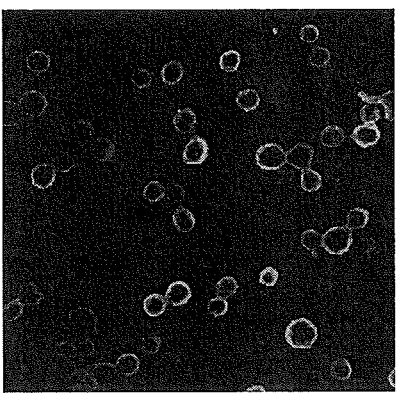
FIG. 38D CD61
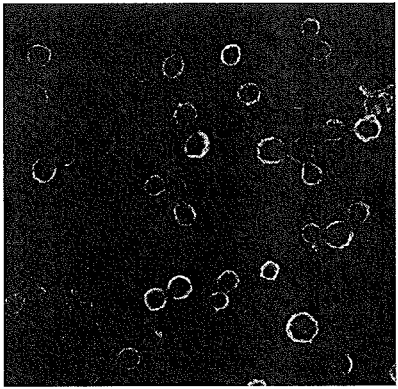
FIG. 38C VWF
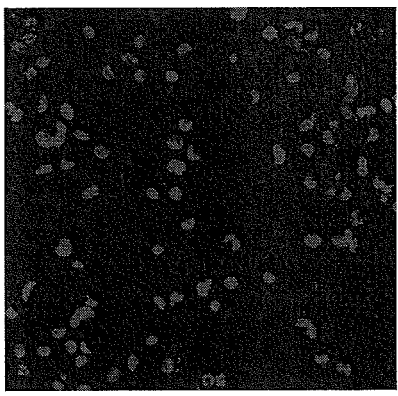
FIG. 38B Nuclei
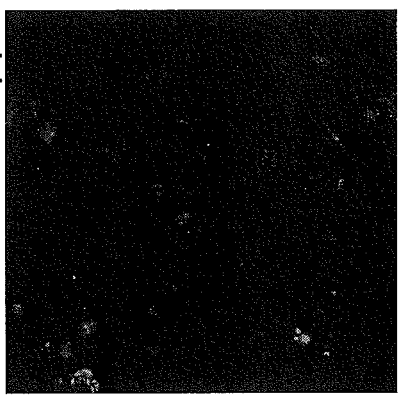
FIG. 38A PF
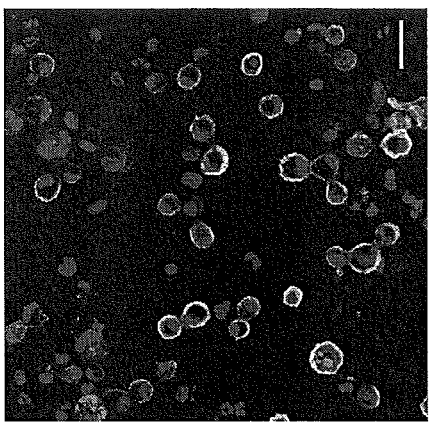
FIG. 38F
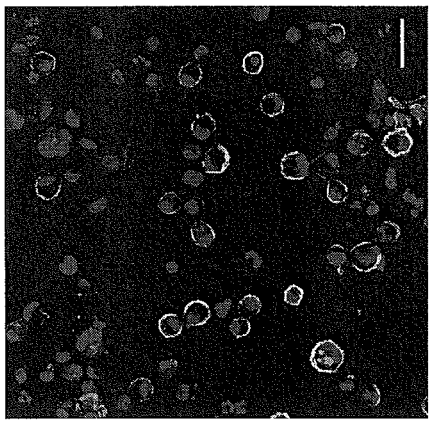
FIG. 38E
Scale bar = 25μm

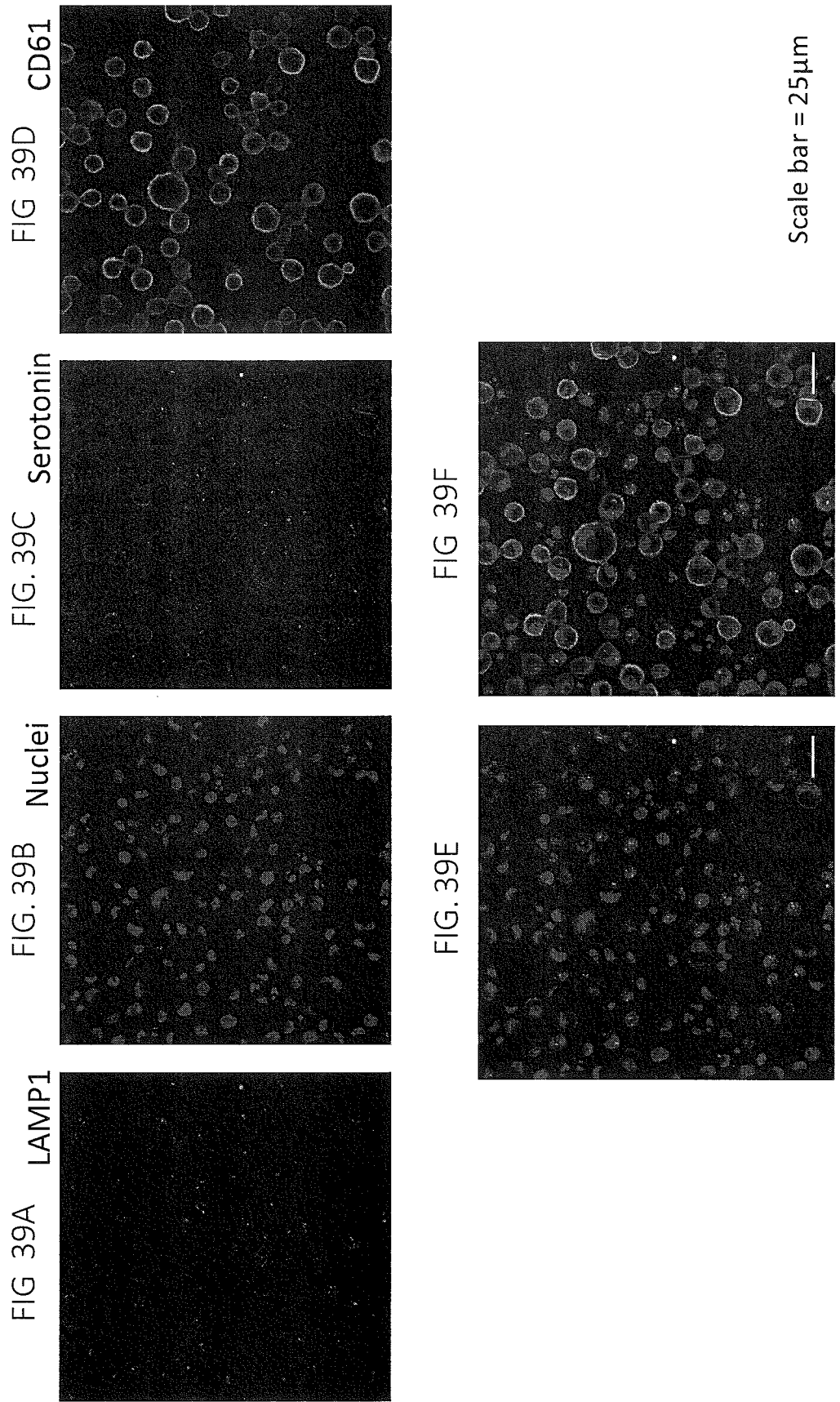

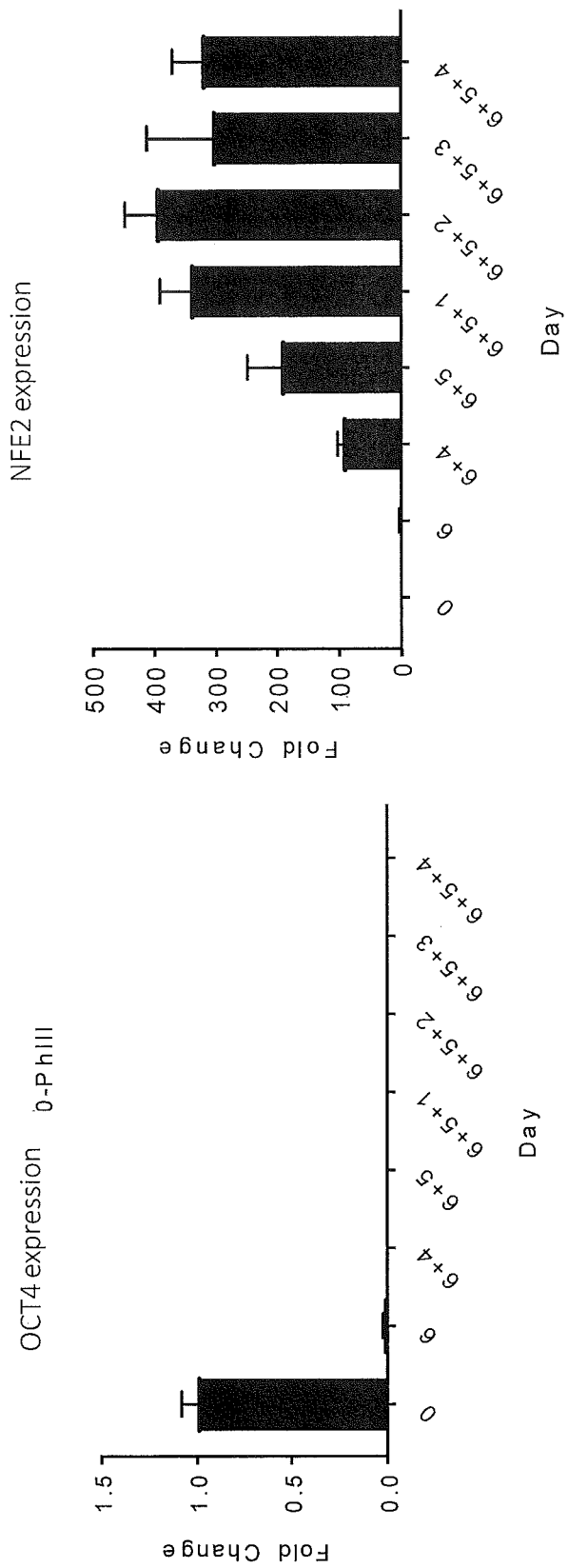

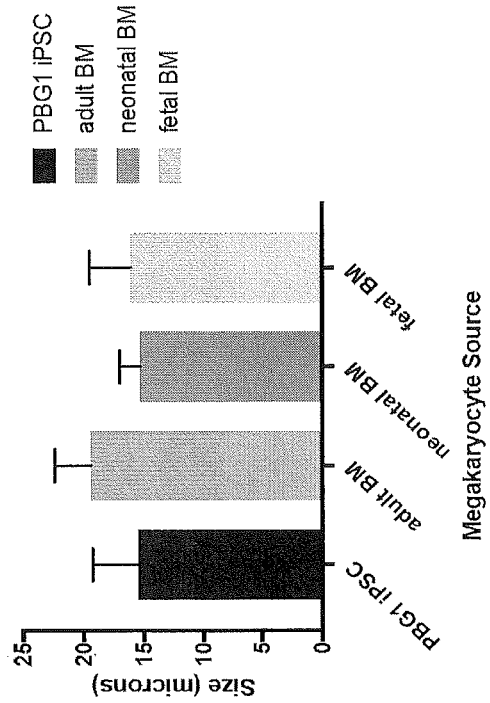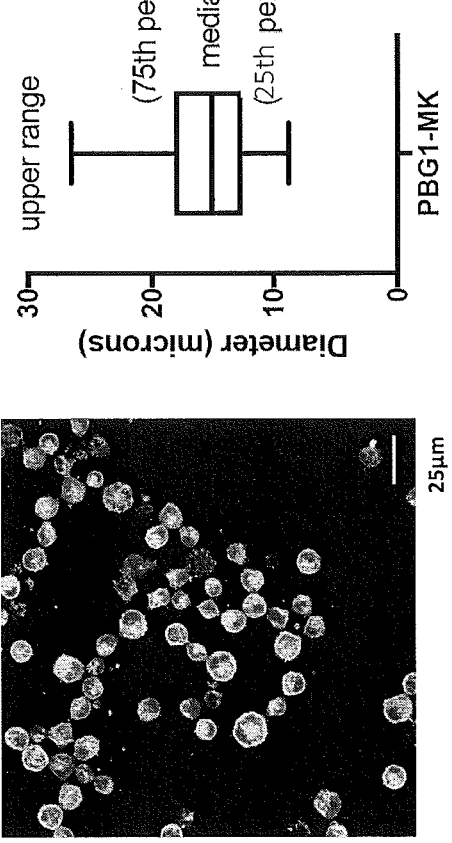
FIG. 42A
FIG. 42B Size distribution
FIG. 42C Comparison with other sources
*Sola-Visner et al., Pediatr Res. 2007 61:479-484
**Ma et al., Eur J Haematol. 1996. 57:121-127

Cumulative Yield of DNA⁻CD41⁺CD42⁺ Calcein AM⁺ platelets per well During Phase III

Platelets

COMPOSITIONS AND METHODS FOR PRODUCING MEGAKARYOCYTES

RELATED APPLICATIONS

This application is a U.S. national phase application of PCT International Patent Application No. PCT/US2019/012437, filed on Jan. 5, 2019, which claims the benefit of and priority to U.S. Provisional Patent Application No. 62/614,117, filed on Jan. 5, 2018, the entirety of each of which is hereby incorporated herein by reference.

STATEMENT OF GOVERNMENT SUPPORT

This work was supported by the following grant from the National Institutes of Health, Grant Nos: 1R44HL131050-01, 1R43AI125134-01A1, and 1SB1HL137591-01. The Government has certain rights in the invention.

FIELD

This disclosure relates to methods for production of megakaryocytic progenitors and megakaryocytes, compositions of megakaryocytic progenitors and megakaryocytes and uses thereof.

BACKGROUND

Platelets are blood cells responsible for clot formation and blood vessel repair at sites of active bleeding. Physiologically, platelets are produced in the bone marrow by parent cells called megakaryocytes (MKs), which comprise <0.1% of cells in the bone marrow. Mature MK sit outside sinusoidal blood vessels in the bone marrow and extend long structures called proplatelets into the circulation. Proplatelets function as the assembly lines for platelet production, and sequentially release platelets from their ends.

MK are produced through a multiple step differentiation process from hematopoietic stem cells in the bone marrow. Exposure to various cytokines, chemokines, and growth factors, including thrombopoietin, results in the differentiation of hematopoietic stem cells to multipotent progenitor cells then to a committed megakaryocytic progenitor cells, also known as pre-MKs. Upon further differentiation, including enlargement of the cells, increased DNA content, endomitosis, and granule formation, mature MKs are produced. MKs convert their cell mass into proplatelet extensions to produce/release anucleate platelets.

Low platelet counts are a significant consequence of various diseases and therapeutics, including cancer treatment, transplantation, and surgery, for which platelets are a critical first-line therapy to prevent mortality due to uncontrolled bleeding. Platelet units ($3\times10^{11}$ platelets per 200-400 mL) are derived exclusively from human volunteer donors and must be stored at room temperature to avoid irreversible activation. However, at this temperature there is a risk for bacterial growth, limiting the shelf life of a platelet unit to 5 days, 2 of which are consumed by pathogen screening and 1 by transport. Consequently, blood centers typically do not have more than 1.5 days of platelet inventory available for transfusion, which is rapidly depleted during emergencies. Donor shortages of platelets can occur, especially at critical times. Mounting demand in civilian use alone exceeds supply by ~20%, and stockpiles are rapidly depleted in emergencies. Furthermore, wide functional variability among units and donors leads to over-transfusion to ensure effective bleeding control. Accordingly, megakaryocytes, which provide a source of platelets, and new, improved methods of generating megakaryocytes are urgently required.

SUMMARY

The present disclosure provides methods for producing megakaryocytic progenitors (preMKs) and megakaryocytes (MKs) from stem cells. The present disclosure further provides compositions comprising preMKs and MKs and their lysates, and also methods of use of preMKs, MKs, their lysates and compositions thereof.

In some embodiments, the present disclosure provides a method for megakaryocyte production comprising: expanding pluripotent stem cells under low adherent or non-adherent conditions and under agitation wherein expanded pluripotent stem cells form self-aggregating spheroids; differentiating the pluripotent cells in a first culture medium into hemogenic endothelial cells; differentiating the hemogenic endothelial cells in a second culture medium into megakaryocytic progenitors. The differentiating of the pluripotent cells into hemogenic endothelial cells can be carried out under adherent conditions on a matrix. In some embodiments, the differentiating of the pluripotent cells into hemogenic endothelial cells is carried out under low-adherent or non-adherent conditions to enable the hemogenic endothelial cells to self-aggregate.

In some embodiments, the present disclosure provides a method for megakaryocyte production comprising: differentiating pluripotent cells in a first culture medium into hemogenic endothelial cells; and differentiating the hemogenic endothelial cells in a second culture medium into megakaryocytic progenitors, wherein at least one of the differentiating the pluripotent cells and the differentiating the hemogenic endothelial cells is carried out on a matrix coated 3-dimensional structure. The 3-dimensional structure can be a microcarrier or a microcarrier.

In some embodiments, the present disclosure provides a method for megakaryocyte production comprising: differentiating pluripotent cells in a first culture medium into hemogenic endothelial cells; and differentiating the hemogenic endothelial cells in a second culture medium into megakaryocytic progenitors, wherein at least one of the differentiating the pluripotent cells and the differentiating the hemogenic endothelial cells is carried out under low-adherent or non-adherent conditions to enable the cells to self-aggregate.

In some embodiments, the first culture medium comprises one or more of Bone morphogenic protein 4 (BMP4), Basic fibroblast growth factor (bFGF), and Vascular endothelial growth factor (VEGF). The first culture medium may further include a WNT modulator. In some embodiments, the second culture medium comprises one or more of Stem cell factor (SCF), Thrombopoietin (TPO), Fms-related tyrosine kinase 3 ligand (Flt3-L), Interleukin-3 (IL-3), Interleukin-6 (IL-6) and Heparin.

In some embodiments, the pluripotent stem cells are human induced pluripotent stem cells.

In some embodiments, the instant methods may further include a step of expanding the pluripotent stem cells on the matrix coated 3-dimensional structure.

In some embodiments, the instant methods may further include a step of differentiating the megakaryocytic progenitors in a third culture medium into megakaryocytes. The third medium can comprise one or more of Stem Cell Factor (SCF), Thrombopoietin (TPO), Interleukin-6 (IL-6), Interleukin-9 (IL-9) and Heparin. In some embodiments, the present disclosure provides compositions of megakaryocytic progenitors or lysates of megakaryocytic progenitors produced by the methods of the present disclosure.

In some embodiments, the present disclosure provides megakaryocytes or lysates of megakaryocytes produced the methods of the present disclosure. In some embodiments, such megakaryocytes are $CD42b^+$, $CD61^+$, and $DNA^+$.

Other features and advantages of the present disclosure will be apparent from the following description, and from the claims.

BRIEF DESCRIPTION OF THE DRAWINGS

The present disclosure will be described in the detailed description which follows, in reference to the noted plurality of drawings by way of non-limiting examples of exemplary embodiments, in which like reference numerals represent similar parts throughout the several views of the drawings, and wherein:

FIG. 3A and FIG. 3B depict the pluripotency of 3 exemplary clinical grade hiPSC lines (here referred to as PBG1, PBG2, PBG3). FIG. 3A depicts low magnification phase contrast images of PBG1, PBG2, and PBG3 iPSCs forming characteristic growth areas when cultured on Vitronectin matrix with Essential 8 media. FIG. 3B depicts higher magnification images of PBG1, PBG2, and PBG3 iPSCs immunostained for the pluripotency factors Oct4 and Nanog, and counterstained with a nuclear dye.

FIG. 4A depicts a general timeline schematic of the directed differentiation process. FIG. 4B shows actual images of PBG1 cultures during Phase 0 (day 0), Phase I (day 2 and day 5), Phase II (day 6+7), and Phase III (day+2 and +4). FIG. 4C shows actual images of PBG2 cultures during Phase 0 (day 0), Phase I (day 2 and day 5), Phase II (day 6+7), and Phase III (day+2 and +4). FIG. 4D shows actual images of PBG3 cultures during Phase 0 (day 0), Phase I (day 2 and day 5), Phase II (day 6+7), and Phase III (day+2 and +4).

FIG. 6A depicts representative CD41/CD43 flow cytometry data for suspension cells harvested from Phase II cultures at Day 6+6 (from left to right: PBG1 PBG2, PBG3). FIG. 6B is a graph showing daily output measurements of CD41+CD43+(megakaryocytic progenitor) cells released into suspension during representative Phase II differentiation cultures of PBG1, PBG2, and PBG3 iPSC lines. Production of $CD41^+CD43^+$ megakaryocytic progenitors in PBG1 and PBG2 differentiation cultures were measured out to Day 6+17, while production of $CD41^+$ $CD43^+$ cells in PBG3 differentiation cultures stopped at Day 6+8. FIG. 6C depicts the cumulative yield of CD41+CD43+ cells during Phase II differentiation cultures of grade hiPSC lines, shown as number of CD41+CD43+ cells/Well.

FIG. 7A depicts the maturation state of PBG1, PBG2, and PBG3 derived cells over time in Phase III cultures, as measured by the proportion of CD41+ megakaryocytic lineage cells that also express the mature megakaryocyte marker CD42b. FIGS. 6B and 6C depict light microscopy images of hiPSC-derived megakaryocytes at day 4 of Phase III that were differentiated from PBG1 and PBG2, respectively. Examples of proplatelet extensions are indicated with arrows.

FIG. 8A, FIG. 8B, FIG. 8C, FIG. 8D, and FIG. 8E depict characterization of mature megakaryocytes derived by differentiation of PBG1, PBG2, and PBG3 hiPSCs. FIG. 8A depicts Phase III cells derived from PBG1 that were immunostained for β1-tubulin, and nuclei were visualized by nucleic acid staining (top panel). Megakaryocytes derived from PBG1 were also analyzed by electron microscopy (bottom panel). FIG. 8B depict Phase III cells derived by differentiation of PBG2 hiPSCs. Megakaryocytes derived from PBG2 were immunostained for β1-tubulin, and nuclei were visualized by nucleic acid staining (top panel). Megakaryocytes derived from PBG2 were also analyzed by electron microscopy (bottom panel). FIG. 8C depict Phase III cells derived by differentiation of PBG3 hiPSCs. Megakaryocytes derived from PBG3 were immunostained for β1-tubulin, and nuclei were visualized by nucleic acid staining (top panel). Megakaryocytes derived from PBG3 were not analyzed by electron microscopy (bottom panel). FIG. 8D depicts the proportion of Phase III cells derived from PBG1, PBG2, and PBG3 iPSCs that stained positive for intracellular Von Willebrand Factor. FIG. 8E depicts the proportion of Phase III cell derived from PBG1, PBG2, and PBG3 iPSC lines that stained positive for intracellular Platelet Factor 4.

FIG. 9A shows PBG1 growth in Essential 8 media. FIG. 9B shows PBG1 growth in StemFlex media. FIG. 9C shows PBG1 growth in Nutristem XF media.

FIG. 10A, FIG. 10B, and FIG. 10C depict flow cytometry data assessing expression of the pluripotency markers Tra-1-60, SSEA5, and the differentiation marker SSEA1 on PBG1 cells expanded on recombinant vitronectin using various growth medias. FIG. 10A shows pluripotency marker data from PBG1 cells expanded in Essential 8 media. FIG. 10B shows pluripotency marker data from PBG1 cells expanded in StemFlex media. FIG. 10C shows pluripotency marker data from PBG1 cells expanded in Nutristem XF media.

FIG. 11A, FIG. 11B and FIG. 11C depict the expansion of PBG1 iPSCs in self-aggregating spheroid cultures in a 3D stir tank (matrix free). FIG. 11A shows microscope images of PBG1 spheroids over time in culture. FIG. 11B depicts the increase in cell density in PBG1 spheroid cultures over time. FIG. 11C depicts the average PBG1 spheroid size over time in 3D culture.

FIG. 12A shows pluripotency marker data for PBG1 cells after a single 7-day expansion in a 3D stir tank. FIG. 12B shows pluripotency data for PBG1 cells after 4 consecutive 6-7 days expansions in a 3D stir tank.

FIG. 13A and FIG. 13B depict PBG1 iPSCs immunostained for the pluripotency factors Oct 4 and Nanog, and counterstained with a nuclear dye. FIG. 13A depicts a portion of a 2D colony of PBG-1 iPSCs grown on vitronectin. FIG. 13B depicts a spheroid of PBG-1 iPSCs grown in 3D stirred conditions (matrix free).

FIG. 16A depicts representative flow cytometric analysis of PBG1-derived cells at day 6 of differentiation. Hemogenic endothelial cells are identified via cell surface expression of CD31 and CD34. FIG. 16B depicts the average and range of Phase I (day 6) differentiation efficiencies over 41 independent PBG1 directed differentiations.

FIG. 17A shows a Phase II culture at day 6+6, with the hemogenic endothelial (HE) monolayer in the background, and megakaryocytic progenitors (preMKs) being released from the monolayer into suspension. FIG. 17B shows flow cytometric analysis of Phase II suspension cells, identifying the CD43+ hematopoietic progenitor cells. FIG. 17C shows flow cytometric analysis of the CD43+ hematopoietic cells, identifying the CD43+CD41+CD14− megakaryocytic progenitors (preMKs). Contaminating CD43+CD14+ myeloid progenitors are also identified in this analysis.

FIG. 18A depicts the average daily purity (i.e. % CD41+CD43+CD14− of viable suspension cells) of released preMKs over 10 days of Phase II. FIG. 18B depicts the median, quartiles, and ranges of the contaminating myeloid progenitors (i.e. % CD43+CD14+ of viable suspension cells) over 10 days of Phase II. All cultures were initiated with PBG1 cells on Collagen IV matrix in a 2D vessel. Data represents 41 independent differentiations.

FIG. 19A depicts the average daily yields of released preMKs (i.e. viable CD41+CD43+CD14−) per 6-well equivalent (i.e. 2 ml of media, 9.5 cm$^2$ surface area) during Phase II directed differentiation cultures initated with PBG1 iPSCs. FIG. 19B depicts the cumulative yields of released preMKs (i.e. viable CD41+CD43+CD14−) per 6-well equivalent (i.e. 2 ml of media, 9.5 cm$^2$ surface area) between day 6+4 and 6+8 of Phase II directed differentiation cultures initiated with PBG1 iPSCs. Each dot represents an independent PBG1 directed differentiation culture on Collagen IV matrix in a 2D culture vessel.

FIG. 20A, FIG. 20B, FIG. 20C, and FIG. 20D depict MK differentiation and proplatelet production in Phase III. FIG. 20A depicts PBG1-derived megakaryocytic progenitors at Day 1 of Phase III (top panel: high magnification; bottom panel: low magnification). FIG. 20B depicts maturing megakaryocytes at Day 2 of Phase III (top panel: high magnification; bottom panel: low magnification). FIG. 20C depicts mature megakaryocytes at Day 4 of Phase III (top panel: high magnification; bottom panel: low magnification). FIG. 20D illustrates spontaneous proplatelet formation from mature PBG1-derived MKs after 4 days of Phase III culture.

FIG. 21A, FIG. 21B, and FIG. 21C depict representative flow cytometric analysis from Day 3 Phase III cultures initiated from PBG1 iPSCs. FIG. 21A identifies the CD61+ (megakaryocytic) fraction of Phase III cells. FIG. 21B shows flow cytometric analysis of the CD61+ megakaryocytic cells, identifying the CD42a+CD42b+ mature MKs. Apoptotic CD42a+CD42b−cells can also be identified in this analysis. FIG. 21C depicts the subset breakdown of a representative Phase III culture. Non-MKs are CD61−, immature MKs are CD61+CD42a−CD42b−, apoptotic MKs are CD61+CD42a+CD42b−, and mature MKs are CD61+CD42a+CD42b+.

FIG. 22A and FIG. 22B shows use of Laminin 521 and Collagen IV in Phase I of directed differentiation of PBG1 cells. FIG. 22A shows the progression of Phase I differentiation on 4.2 ug/cm$^2$ of human collagen IV. FIG. 22B shows the progression of Phase I differentiation on 0.13 ug/cm$^2$ of recombinant human laminin 521.

FIG. 23A, FIG. 23B, and FIG. 23C depict use of recombinant Laminin 521 to support production and release of megakaryocytic progenitors in Phase II of directed differentiation of PBG1 cells. FIG. 23A depicts representative flow cytometric data from Phase II of PBG1 differentiation cultures utilizing a supportive matrix of 4.2 ug/cm$^2$ human Collagen IV. FIG. 23B depicts representative flow cytometric data from Phase II of PBG1 differentiation cultures utilizing a supportive matrix of 0.13 ug/cm$^2$ recombinant human Laminin 521. FIG. 23C depicts the cumulative yields of released preMKs (i.e. viable CD41+CD43+CD14−) per 6-well equivalent (i.e. 2 ml of media, 9.5 cm$^2$ surface area) between day 6+4 and 6+8 of Phase II directed differentiation cultures initiated with PBG1 iPSCs, utilizing a supportive matrix of 4.2 ug/cm$^2$ human Collagen IV or 0.13 ug/cm$^2$ recombinant human Laminin 521.

FIG. 25A shows a flow cytometric subset breakdown of Phase III (Day 6+6+3) cultures initiated with preMKs from Collagen IV cultures. FIG. 25B shows a flow cytometric subset breakdown of Phase III (Day 6+6+3) cultures initiated with preMKs from recombinant Laminin 521 cultures. Non-MKs are CD61−, Immature MKs are CD61+CD42a−CD42b−, Apoptotic MKs are CD61+CD42a+CD42b−, and Mature MKs are CD61+CD42a+CD42b+.

FIG. 26A, FIG. 26B, and FIG. 26C depict immunofluorescence microscopy images of Day 6 Phase I cultures on Laminin 521. FIG. 26A depicts a control culture without WNT agonist. FIG. 26B depicts a culture where 0.6 uM of the WNT agonist CHIR98014 was added to the differentiation culture for the first 48 hours of Phase I. FIG. 26C depicts a culture where 6 uM of the WNT agonist CHIR99021 was added to the differentiation culture for the first 48 hours of Phase I.

FIG. 27A and FIG. 27B depict immunofluorescence microscopy images of Day 6+4 Phase II cultures on Laminin 521. FIG. 27A depicts a control culture without WNT agonist. FIG. 27B depicts a culture where 0.6 uM of the WNT agonist CHIR98014 was added to the first 48 hours of Phase I.

FIG. 29 depicts Phase I differentiation of PBG-1 iPSCs on Laminin521 coated Rachig rings at day 3 and day 6.

FIG. 30 depicts Phase II differentiation of PBG-1 iPSCs on Laminin521 coated Rachig rings at day 6+0 and day 6+4.

FIG. 31A, FIG. 31B, and FIG. 31C depict flow cytometric data from phases of PBG1 differentiation proceeding efficiently on Rachig ring substrate. FIG. 31A depicts Phase I at day 6, with flow cytometric staining for the hemogenic endothelial markers CD31 and CD34. FIG. 31B depicts Phase II at day 6+2, with flow cytometric staining for the megakaryocytic progenitor markers CD43 and CD41. FIG. 31C depicts Phase III at Day 6+3+3, with flow cytometric staining for CD61 and CD42b.

FIG. 32 is a schematic of an exemplary 3D, matrix independent method of directed differentiation using self-aggregating iPSC-derived spheroids in a stir tank.

FIG. 33A depicts a series of micrographs, starting with single cell dissociated PBG1 cells at day −1, self-aggregated PBG1 iPSC spheroids at day 0, partially differentiated spheroids at day 3, and fully differentiated spheroids containing hemogenic endothelial cells at day 6. FIG. 33B depicts day 6 flow cytometric data showing successful CD31+CD34+ hemogenic endothelial differentiation using this approach.

FIG. 34A depicts self-aggregated PBG1-derived spheroids at day 6+4 during Phase II of directed differentiation, with preMKs released from the spheroids into suspension. FIG. 34B depicts flow cytometric analysis of the harvested suspension cells, staining for the preMK markers CD41 and CD43. FIG. 34C depicts the preMK purity over time in Phase II, in 2 different 3D systems, an ultra-low adherent vessel on an orbital shaker, and a spinner flask. FIG. 34D depicts the preMK yields over time in Phase II in 2 different 3D systems, an ultra-low adherent vessel on an orbital shaker, and a spinner flask.

FIG. 35A depicts representative flow cytometric analysis from Day 3 Phase III cultures, identifying the CD61+(megakaryocytic) fraction of Phase III cells, followed by identification of the CD42a+CD42b+ mature MKs. Apoptotic CD42a+ CD42b− cells can also be identified in this analysis. FIG. 35B depicts the subset breakdown of a representative Phase III culture. Non-MKs are CD61−, immature MKs are CD61+CD42a-CD42b−, apoptotic MKs are CD61+CD42a+ CD42b−, and mature MKs are CD61+CD42a+CD42b+. FIG. 35C shows how the mature MK fraction within Phase III cultures at day 3 compares between 2D (matrix-dependent) and 3D (matrix-independent) approaches.

FIG. 36 depicts proplatelet extensions of mature MK harvested from 3D self-aggregating spheroid differentiation cultures. Examples of proplatelet extensions are indicated with arrows.

FIG. 38A, FIG. 38B, FIG. 38C, FIG. 38D, FIG. 38E and FIG. 38F depict PBG1-derived megakaryocytes immunostained for the α-granule specific proteins Platelet Factor 4 (PF4), Von Willebrand Factor (VWF), as well as for the megakaryocyte-specific cell surface marker CD61, and nuclei.

FIG. 39A, FIG. 39B, FIG. 39C, FIG. 39D FIG. 39E, and FIG. 39F depict PBG1-derived megakaryocytes immunostained for the Dense Granule specific proteins LAMP1 and serotonin, as well as for the megakaryocyte-specific cell surface marker CD61, and nuclei.

FIG. 40A is an electron microscopy image showing a PBG1-derived megakaryocyte producing microparticles (see arrows for examples). FIG. 40B is an electron microscopy image showing a PBG1-derived megakaryocyte and multivesicular bodies (arrows; magnified in inset). FIG. 40C is an electron microscopy image showing a PBG1-derived megakaryocyte, characterized by multi-lobed nuclei, glycogen granules, alpha-granules, and an invaginated membrane system. FIG. 40D is an electron microscopy image showing the endoplasmic reticulum and mitochondria of a PBG1-derived megakaryocyte.

FIG. 41A, FIG. 41B, and FIG. 41C illustrate characteristic gene expression changes that occur through the course of PBG1 directed differentiation to megakaryocytes. For all expression analyses, the expression in the pluripotent PBG1 cells was set at 1, and all other expression values are presented in relative terms. FIG. 41A illustrates the relative gene expression of Oct4, a pluripotency-associated gene, in pluripotent PBG1 cells, Day 6 cells (end of Phase I), Days 6+4 and 6+5 (Phase II), and Days 6+5+1 through 6+5+4 (Phase III). FIG. 41B illustrates the relative gene expression of NFE2, a transcription factor critical for megakaryocyte maturation, in pluripotent PBG1 cells, Day 6 cells (end of Phase I), Days 6+4 and 6+5 (Phase II), and Days 6+5+1 through 6+5+4 (Phase III). Similar analyses were performed on a panel of relevant genes, and the results of this analysis are summarized in the heat map shown in FIG. 41C, with genes OCT4, SOX2, NANOG, and ZFP42 being downregulated during differentiation, genes ZFPM1, NFE2, RUNX1, MEIS1, and GATA1 being upregulated during differentiation, and genes PBX1 and MYC remaining at a substantially consistent level.

FIG. 42A, FIG. 42B and FIG. 42C provide size distributions of PBG1 derived megakaryocytes. FIG. 42A depicts a representative example of β1-Tubulin staining of PBG1 derived megakaryocytes, which were utilized to collect size measurements of PBG1-MKs and compare with MKs from other sources. FIG. 42B depicts the size distribution of PBG1 derived megakaryocytes, including the median, quartiles, and range. FIG. 42C compares the size distribution data of PBG1 derived MKs with megakaryocytes from various bone marrow sources.

FIG. 43A depicts a representative example of DNA ploidy measurements performed on PBG1 derived megakaryocytes. FIG. 43B compares the DNA ploidy measurements of PBG1-MKs with MKs from other sources.

FIG. 45A depicts flow cytometric analysis of anucleate and nucleated cells (upper, left). Nucleated cells contained a large number of CD41$^+$CD42$^+$ megakaryocytes (upper, right). Anucleate cells positive for CD41$^+$, CD42$^+$, and Calcein AM were assessed using flow cytometry and platelets were gated by size (1-5 microns). FIG. 45B shows examples of platelets harvested from megakaryocyte culture assessed by electron microscopy. FIG. 45C is a graph depicting cumulative yield of CD41$^+$CD42$^+$ Calcein AM$^+$ platelet-sized particles per well during Phase III of the directed differentiation protocol described herein.

Figure 1:
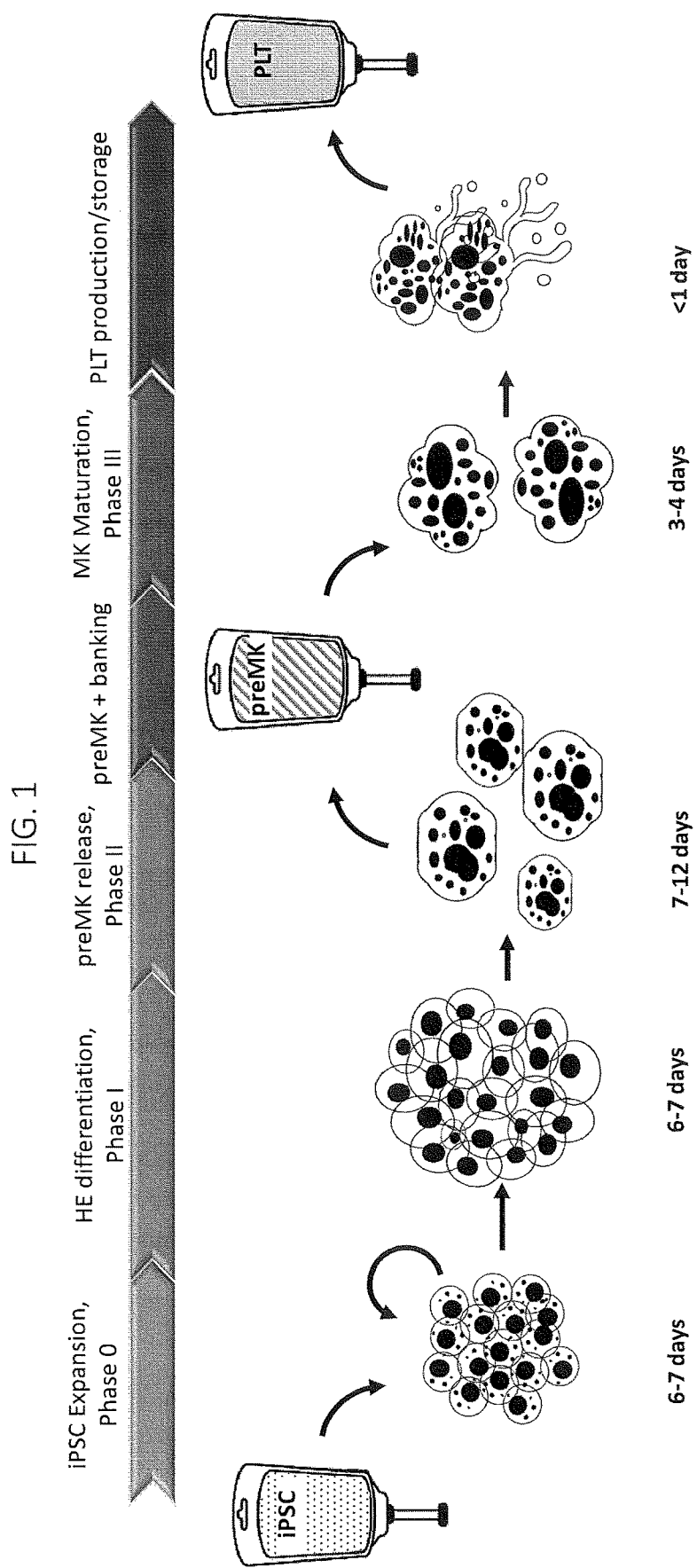
FIG. 1 shows an overall schematic for scalable differentiation of megakaryocytic progenitors (preMKs), megakaryocytes (MK), and platelets (PLT) from a iPSC line.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The present disclosure is directed to compositions and methods for producing megakaryocytic progenitors (preMKs) and megakaryocytes (MKs) from stem cells, such as, pluripotent stem cells, for example, clinical-grade human induced pluripotent stem cells. The methods enable the continued production of preMKs from hemogenic endothelial cells for extended time frames (up to 8 days or more), which can then be subsequently differentiated into mature MKs. The preMKs and MKs derived by the instant methods can be distinguished by one or more of the following: their size range, ploidy profile, biomarker expression, gene expression, granule composition, and growth factor, cytokine and chemokine composition or combinations thereof. The present disclosure further provides compositions comprising preMKs and MKs and their lysates, and also methods of use of preMKs and MKs and their lysates and compositions thereof.

Definitions

Unless defined otherwise, all technical and scientific terms used herein have the meaning commonly understood by a person skilled in the art to which the present disclosure belongs. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant any small molecule chemical compound, antibody, nucleic acid molecule, or polypeptide, or fragments thereof.

The term "antibody," as used herein, refers to an immunoglobulin molecule which specifically binds with an antigen. The term "antibody fragment" refers to a portion of an intact antibody and refers to the antigenic determining variable regions of an intact antibody.

By "alteration" or "change" is meant an increase or decrease. An alteration may be by as little as 1%, 2%, 3%, 4%, 5%, 10%, 20%, 30%, or by 40%, 50%, 60%, or even by as much as 70%, 75%, 80%, 90%, or 100%.

By "biologic sample" is meant any tissue, cell, fluid, or other material derived from an organism.

By "capture reagent" is meant a reagent that specifically binds a nucleic acid molecule or polypeptide to select or isolate the nucleic acid molecule or polypeptide.

By "cellular composition" is meant any composition comprising one or more isolated cells.

By "cell survival" is meant cell viability.

As used herein, "clinical grade" is meant to refer to a cell or cell line derived or obtained using current Good Manufacturing Practice (GMP), which permits its clinical use in humans. GMP is a quality assurance system used in the pharmaceutical industry to ensure that the end product meets preset specifications. GMP covers both manufacturing and testing of the final product. It requires traceability of raw materials and also that production follows validated standard operating procedures (SOPs).

By "detectable levels" is meant that the amount of an analyte is sufficient for detection using methods routinely used to carry out such an analysis.

"Detect" refers to identifying the presence, absence or amount of the object to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ. Examples of diseases include any disease or injury that results in a reduction in cell number or biological function, including ischemic injury, such as stroke, myocardial infarction, or any other ischemic event that causes tissue damage, peripheral vascular disease, wounds, burns, fractures, blunt trauma, arthritis, and inflammatory diseases.

By "effective amount" is meant the amount of an agent required to produce an intended effect.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high-performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the disclosure is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the disclosure that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the disclosure. An isolated polypeptide of the disclosure may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

The term "hemogenic endothelial cell" as used herein refers to cells capable of differentiating to give rise to hematopoietic cell types or endothelial cell types, and which may optionally be derived from pluripotent stem cells. Hemogenic endothelial cells are normally adherent to extracellular matrix protein and/or to other hemogenic endothelial cells, and can be characterized, in some embodiments, by the expression of the markers CD31 and CD34.

By "marker" is meant any protein or other epitope having an alteration in expression level or activity that is associated with a characteristic or condition.

The term "megakaryocyte" (MK) as used herein refers to a large (e.g., diameter ≥10 μm), polyploid hematopoietic cell with the propensity to generate proplatelets and/or platelets. One morphological characteristic of mature MKs is the development of a large, multi-lobed nucleus. Mature MKs can stop proliferating, but continue to increase their DNA content through endomitosis, with a parallel increase in cell size.

The term "megakaryocytic progenitor" (preMK), as used herein, refers to a mononuclear hematopoietic cell that is committed to the megakaryocyte lineage and is a precursor to mature megakaryocytes. Megakaryocytic progenitors are normally found in (but not limited to) bone marrow and other hematopoietic locations, but can also be generated from pluripotent stem cells, such as by further differentiation of hemogenic endothelial cells that were themselves derived from pluripotent stem cells.

The term "microparticle" refers to a very small (<1 micron) phospholipid vesicle shed from a megakaryocyte or other cell. Microparticles may contain genetic material such as RNA, and express extracellular markers of their parental cells. Megakaryocyte- and platelet-derived microparticles may have a role in multiple pathways, including; hemostasis and inflammation.

The term "platelet" (PLT) refers to a cell with a diameter of 1-3 microns with no nucleus but does contain RNA. Platelets can express CD41, CD42b, and CD61 on its cell surface. Internally, it contains alpha and dense granules, which contain such factors as P-selectin and serotonin, respectively. Platelets also have an open canalicular system, which refer to channels that are a pathway for the transport of extracellular material into the cell and the release of material from granules to the extracellular environment. They primarily function in the regulation of hemostasis by participating in blood clotting but also have been shown to have a role in inflammation.

The term "preplatelet" refers to a cell with a diameter of 3-10 microns with no nucleus but with RNA. Preplatelets are otherwise morphologically and ultra-structurally similar to platelets and constitute an intermediate cell stage produced by megakaryocytes that break apart through cytoskeletal rearrangement to form individual platelets.

The term "proplatelet" refers to cytosolic extensions from megakaryocytes or just released from megakaryocytes. Proplatelets break apart through cytoskeletal rearrangement to form individual preplatelets and platelets.

The term "pluripotent stem cell" includes embryonic stem cells, embryo-derived stem cells, and induced pluripotent stem cells and other stem cells having the capacity to form cells from all three germ layers of the body, regardless of the method by which the pluripotent stem cells are derived. Pluripotent stem cells are defined functionally as stem cells that can have one or more of the following characteristics: (a) be capable of inducing teratomas when transplanted in immunodeficient (SCID) mice; (b) be capable of differentiating to cell types of all three germ layers (e.g., can differentiate to ectodermal, mesodermal, and endodermal cell types); or (c) express one or more markers of embryonic stem cells (e.g., express Oct 4, alkaline phosphatase. SSEA-3 surface antigen, SSEA-4 surface antigen, SSEA-5 surface antigen, Nanog, TRA-1-60, TRA-1-81, SOX2, REX1, etc.).

The term "induced pluripotent stem cells" (iPS cells or iPSCs) refers to a type of pluripotent stem cell generated by reprogramming a somatic cell by expressing a combination of reprogramming factors. The iPSCs can be generated using fetal, postnatal, newborn, juvenile, or adult somatic cells. Factors that can be used to reprogram somatic cells to pluripotent stem cells include, for example, a combination of Oct 4 (sometimes referred to as Oct 3/4), Sox2, c-Myc, and Klf4. In other embodiments, factors that can be used to reprogram somatic cells to pluripotent stem cells include, for example, a combination of Oct 4, Sox2, Nanog, and Lin28. In certain embodiments, at least two, three, or four reprogramming factors are expressed in a somatic cell to reprogram the somatic cell.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

By "reduces" is meant a negative alteration of at least 10%, 25%, 50%, 75%, or 100%.

By "reducing cell death" is meant reducing the propensity or probability that a cell will die. Cell death can be apoptotic, necrotic, or by any other means.

By "reduced level" is meant that the amount of an analyte in a sample is lower than the amount of the analyte in a corresponding control sample.

By "reference" is meant a standard or control condition.

By "specifically binds" is meant a compound or antibody that recognizes and binds a polypeptide of the disclosure, but which does not substantially recognize and bind other molecules in a sample, for example, a biological sample, which naturally includes a polypeptide of the disclosure.

The term "subject" or "patient" refers to an animal which is the object of treatment, observation, or experiment. By way of example only, a subject includes, but is not limited to, a mammal, including, but not limited to, a human or a non-human mammal, such as a non-human primate, murine, bovine, equine, canine, ovine, or feline.

As used herein, the terms "treat," treating," "treatment," and the like refer to reducing or ameliorating a disorder or symptoms associated therewith. It will be appreciated that, although not precluded, treating a disorder or condition does not require that the disorder, condition or symptoms associated therewith be completely eliminated.

By, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Megakaryocytes

In the human body, megakaryocytes are derived from $CD34^+$ hematopoietic stem cells that mainly reside in the bone marrow, but are also found in the yolk sac, fetal liver, and spleen during early development. During MK differentiation, MK precursors undergo a period of endomitosis, whereby MKs become polyploid through multiple cycles of DNA replication without cell division, yielding a polylobulated nucleus with up to 128n copies of DNA. As MKs increase in size they also refine their transcriptional and proteomic profiles, acquire a number of highly specialized granules including α-granules and dense-granules, and develop a highly invaginated membrane system, which are hallmarks of MK maturation and development.

To produce platelets, MKs migrate adjacent to blood vessels in the bone marrow through which they extend long structures called proplatelets into the circulation. Proplatelets function as the assembly lines for platelet production, and sequentially release multiple anucleate platelets from their ends.

While platelets are primarily responsible for clot formation at sites of active hemorrhage, it is becoming increasingly apparent that they also play significant roles in wound healing, angiogenesis, and innate immunity. Among the stem cell-based therapeutic landscape, platelets are an ideal early entrant because they: 1) are in high clinical demand due to their short inventory shelf-life; 2) are anucleate and can be safely irradiated to kill any contaminating nucleated cells, thereby reducing the risk of teratoma development; 3) do not require HLA or blood type matching for the majority (>90%) of platelet transfusions, which will facilitate large-scale manufacture of allogeneic human pluripotent stem cells (hPSCs) for off-the-shelf therapy; 4) are short-lived and well characterized, which will simplify projected clinical trials; 5) are easily transplanted; and 6) would benefit tremendously from sterile manufacture, as current donor-based platelet transfusions are inherently susceptible to bacterial and viral contamination.

Current platelet demand exceeds supply by ~20%, and unmet demand is expected to more than double by 2022 due to a growing and aging population requiring more platelet-based procedures, new medications that reduce platelet counts, and the expansion of existing uses of platelet transfusions to improve healing time. In the United States, the blood market effectively operates as an oligopoly, with the American Red Cross and America's Blood Centers each controlling a little less than half of the market and HemeXcel as the third major blood provider.

There are numerous other potential markets for preMKs and MKs and their growth factors. For example, preMKs, MKs and their lysates can be used for cell culture, tissue regeneration, wound healing, drug delivery, and in the cosmetics industry for skin rejuvenation. As megakaryocytes produced by the methods described herein contained many growth factors they can be a source of therapeutic compositions and/or used for many therapeutic purposes. The present disclosure addresses these needs by establishing a scalable, current good manufacturing practice (cGMP)-compliant commercial platform to make human iPSC-derived human megakaryocytes and products thereof.

Outside the body, MKs can reasonably be derived from various major stem cell sources, for example pluripotent stem cells, hematopoietic stem cells, or other stem cell types.

In some embodiments, MKs can be derived from pluripotent stem cells, including but not limited to, embryonic stem cells (ESCs) (e.g. human embryonic stem cells) and induced pluripotent stem cell (iPSCs) (e.g. human induced pluripotent stem cells). ESCs are pluripotent stem cells derived from the inner cell mass of an early-stage preimplantation embryo called a blastocyst. iPSCs are a type of pluripotent stem cell that can be generated from adult cells by inducing timed expression of particular transcription factors. iPSCs can be expanded and maintained in culture indefinitely and engineered to produce MKs.

In some embodiments, MKs can be derived from hematopoietic stem cells, including but not limited, to $CD34^+$ umbilical cord blood stem cells (UCB cells) (e.g. human $CD34^+$ umbilical cord blood stem cells), $CD34^+$ mobilized peripheral blood cells (MPB cells) (e.g. $CD34^+$ human mobilized peripheral blood), or CD34+ bone marrow cells. UCB cells are multipotent stem cells derived from blood that remains in the placenta and the attached umbilical cord after childbirth. MPB cells are multipotent stem cells derived from volunteers whose stem cells are mobilized into the bloodstream by administration of G-CSF or similar agent.

In some embodiments, MKs can be derived from other stem cell types, including but not limited to mesenchymal stem cells (MSC) (such as, adipose-derived mesenchymal stem cells (AdMSC)) or mesenchymal stem from other sources.

AdMSCs are derived from white adipose tissue, which is derived from the mesoderm during embryonic development and is present in every mammalian species, located throughout the body. Due to their wide availability and ability to differentiate into other tissue types of the mesoderm-including bone, cartilage, muscle, and adipose-ASCs may serve a wide variety of applications.

In the present disclosure, the stem cell cultures are maintained independently of embryonic fibroblast feeder cells and/or animal serum that can potentially be contaminated with xenogeneic pathogens and increase the risk for an immunogenic reaction in humans. Therefore, serum-free, feeder-cell free alternatives are utilized in the instant methods to avoid the introduction of animal products into the preMKs and MKs derived according to the instant methods to ensure safe and animal product-free conditions and products.

Methods of Production

FIG. 1 shows an overall schematic for scalable differentiation of megakaryocytic progenitors (preMKs), megakaryocytes (MK), and platelets (PLT) from one or more pluripotent stem cells. However, it should be noted that while the instant processes are described in connection with pluripotent stem cells, in various embodiments, pluripotent stem cells may be substituted or supplemented with other types of stem cells.

Phase 0: Expansion of Human Induced Pluripotent Stem Cells and Preparation for Differentiation Matrix-Dependent Expansion Cultures For matrix-dependent expansion cultures, clinical grade pluripotent stem cells (PSCs) can be expanded as colonies by culturing without feeder cells on a supportive matrix in a pluripotent stem cell culture medium. The supportive matrix can be a 2 dimensional surface or a 3 dimensional structure. In some embodiments, the clinical grade human induced pluripotent stem cells can be human induced pluripotent stem cells (iPSCs) such as PBG1, PBG2, or PBG3, but other types of pluripotent stem cells, such as embryonic stem cells, or other stem cells can be used.

In some embodiments, the supportive matrix can be, by way of a non-limiting example, recombinant vitronectin, recombinant laminin, Matrigel or any combinations of the foregoing. In some embodiments, the pluripotent stem cell culture medium can be, for example, but not limited to, Essential 8 medium (ThermoFisher), StemFlex medium (Thermofisher), NutriStem medium (Biological Industries), or other medium able to support the maintenance and growth of pluripotent cells known in the art. In some embodiments, the cells can be cultured to reach confluency. In some embodiments, the cells can be cultured to reach from 30% to 90% % confluency. In some embodiments, the cells are cultured to reach up to 60%, up to 65%, up to 70%, up to 75% confluency. For example, the cells are cultured to reach about 70% confluency. Upon reaching a predetermined maximum percent confluency, the cells are harvested. In some embodiments, the cells can be harvested as clumps by dissociation using from 0.1 mM to 5 mM EDTA or similar chelating agent or reagent. For example, the cells can be harvested using about 0.5 mM EDTA. In some embodiments, the cells can be harvested as single cells, such as, for example, by dissociation with proteolytic enzymes, collagenolytic enzymes, or combinations thereof. For example, the cells can be harvested as single cells by dissociation with, for example, recombinant trypsin such as TrypLE™, or Accutase™. For maintenance/expansion of PSCs, the harvested cells can be resuspended in pluripotent stem cell culture medium.

Matrix-Independent 3D Expansion Cultures

For matrix-independent 3D expansion cultures, clinical grade PSCs can be expanded as self-aggregating spheroids. In some embodiments, this can be achieved by seeding single cells at a density from about 0.1 to about 1.5 million per ml. For example, in some embodiments, single cells can be seeded at 0.5 million per ml.

The cells can be subjected to continuous motion by slow stirring or gentle shaking in low-adherent or non-adherent conditions in a pluripotent stem cell culture medium. In some embodiments, feeder free, serum free medium can be used. The pluripotent stem cell culture medium can be, for example, but not limited to, Essential 8 medium (ThermoFisher), StemFlex medium (Thermofisher), NutriStem medium (Biological Industries), or other similar medium able to support the maintenance and growth of pluripotent cells known in the art. In some embodiments, the PSC spheroids are cultured until reaching an overall cell density of from about 3 to about 10 million cells/ml and/or attain a median spheroid size of about 150 to about 350 μm, for approximately 5-7 days. In some embodiments, the PSC spheroids are cultured until reaching an overall cell density of 5 million cells/ml. In some embodiments, the PSC spheroids are cultured until the cells attain a median spheroid size of about 250 μm. The culturing step may last for 4, 5, 6, 7, or 8 days. When applicable, PSCs can be harvested as single cells by dissociation with proteolytic enzymes, collagenolytic enzymes, or combinations thereof. For example, the cells can be harvested as single cells by dissociation with, but not limited to trypsin, recombinant trypsin such as TrypLE™, Accutase™, or similar reagent known in the art. In some embodiments, the single cells are used to initiate another 3D expansion culture and/or directed differentiation culture.

Preparation for Differentiation

In some embodiments, to prepare for differentiation, PSC aggregates can be generated by partial dissociation of PSC colonies from matrix-dependent 2D cultures, by partial dissociation of PSC spheroids from matrix-independent 3D cultures, or by self-aggregation of single PSCs generated by any method known in the art. In some embodiments, prior to initiation of differentiation, these aggregates can be resuspended and cultured in a pluripotent stem cell culture medium, for example, but not limited to, Essential 8 medium (ThermoFisher), StemFlex medium (Thermofisher), or NutriStem medium (Biological Industries). In some embodiments, the medium may include an ROCK inhibitor, such as, for example, but not limited to, Y27632, H1152, or combination thereof. In some embodiments, the cells can be cultured for between 0 and 72 hours at 37° C., 5% CO2, 20% O2 prior to initiation of differentiation.

For matrix-dependent cultures, the aggregates can be allowed to attach to a surface. In some embodiments, the step of attachment may be allowed to proceed for about 24 hours, although any time between 1 hour and 24 hours or longer may be used. In some embodiments, the surface can be pre-coated with collagen, laminin, or any other extracellular matrix protein. In some embodiments, human collagen IV can be used for coating the surface. In some embodiments, the matrix-coated surface can be 2D (for example, the bottom of a plastic dish or flask). In some embodiments, the matrix-coated surface can be 3D (for example, smooth or textured spherical microcarriers, macrocarriers, such as, Rauchig rings). The cells on the 3D matrix coated surfaces can then be cultured with or without continuous motion. For example, the cells can be cultured under ultra-low-adherent static conditions, in roller bottles, spinner flasks, stir tank bioreactors, vertical wheel bioreactors, packed bed bioreactors, or fluidized bed systems.

For matrix-independent cultures, the aggregates can be subjected to continuous motion by slow stirring or gentle shaking in a low-adherent vessel. The cells can be transitioned into Phase I of differentiation after between 0 and 72 hours, for example after about 24 hours.

Phase I. Generation of Hemogenic Endothelial Cells

In Phase I, prepared PSCs can be differentiated into hemogenic endothelial cells. Briefly, the pluripotent stem cell culture medium is removed and replaced with Phase I differentiation medium. In some embodiments, the Phase I differentiation medium can be an animal-component free medium (ACF) comprising StemSpan™-ACF (STEMCELL Technologies, Cat. No. 09855) as basal medium, supplemented with one or more growth factors, including, for example, bone morphogenic protein 4 (BMP4), basic fibroblast growth factor (bFGF), and vascular endothelial growth factor (VEGF). In some embodiments, the basal medium is supplemented with between 1 and 200 ng/ml of one or more each of BMP4 (for example, at 50 ng/ml), bFGF (for example, at 50 ng/ml), and VEGF (for example, at 50 ng/ml) Cells can be incubated for between 2 and 6 days in low oxygen conditions (for example, 37° C., 5% $CO_2$, 5% $O_2$), followed by between 2 and 6 days in normoxia (37° C., 5% $CO_2$, 20% $O_2$). In some embodiments, WNT modulators such as, for example, WNT agonists or antagonists can be added for the initial period of differentiation. In some embodiments, GSK3 inhibitors can be added for the initial period of differentiation. In some embodiments, the GSK3 inhibitors or WNT agonists, such as, for example, CHIR9998014, CHIR99021 or a combination thereof, can be added for the initial period of differentiation, such as for between 1 and 2 days. In some embodiments, WNT modulators can replace one or more of the growth factors for at least a portion of Phase I. For example, in some embodiments, while WNT modulators are present, BMP4 can be added for the first 48 hours and can be dispensable for the remainder of Phase I. In some embodiments, VEGF and bFGF can be dispensable for the first 48 hours while WNT modulators are present. In some embodiments, daily full media exchanges can be performed throughout Phase I by removal of spent media and replacement with fresh Phase I media. In some embodiments, partial media exchanges can be performed, with 10-95% of the spent media removed and replaced with equivalent volumes of fresh Phase I media. In some embodiments, additional volumes of fresh media can be added with the net effect of increasing the total volume of the culture. In some embodiments, specific media components are spiked into the culture in lieu of replacement or addition of fresh Phase I media.

Figures 4A, 4B, 4C, 4D:
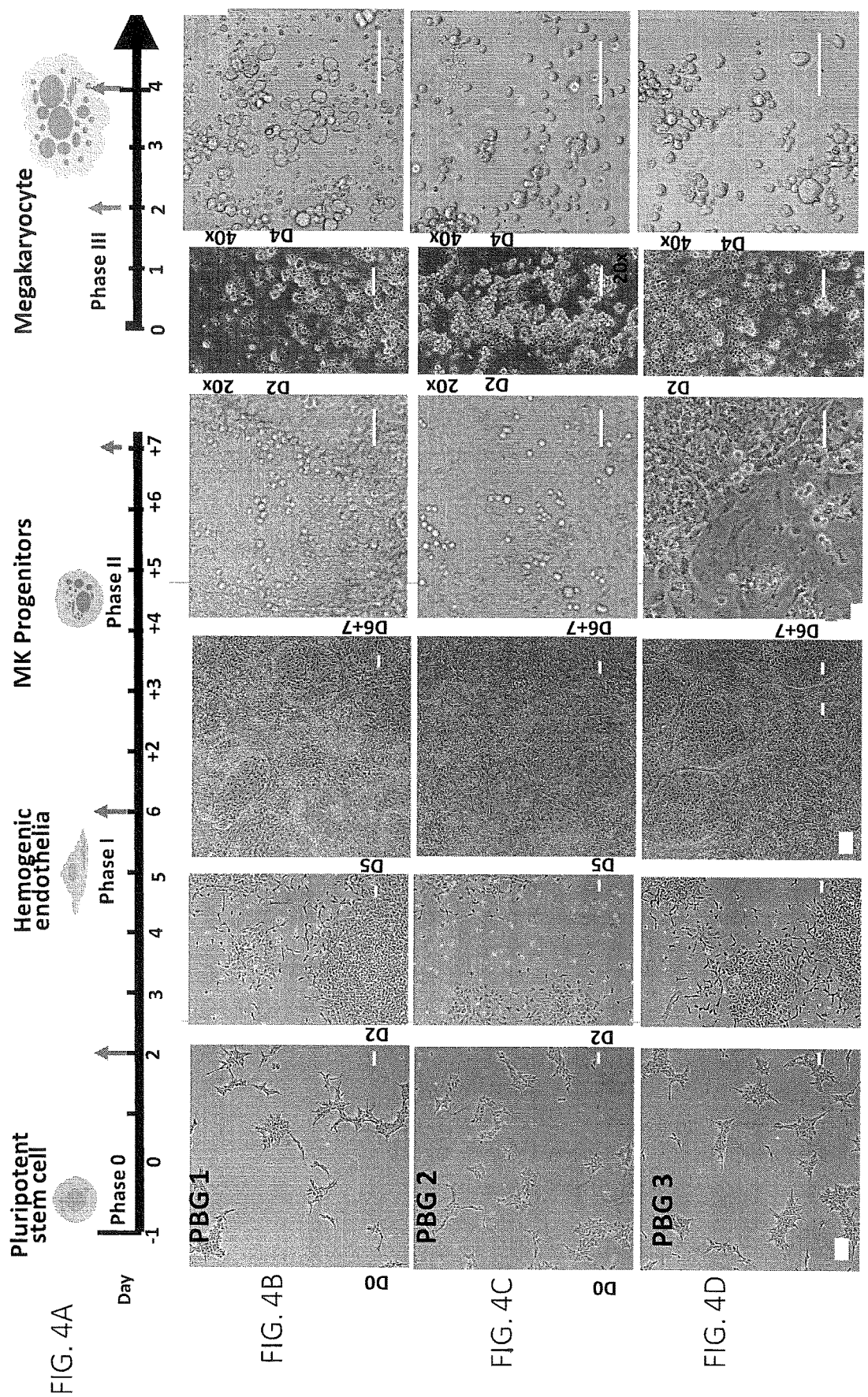
FIG. 4A, FIG. 4B, FIG. 4C, and FIG. 4D depict cultures of PBG1, PBG2, and PBG3 iPSCs progressing through phases of directed differentiation from pluripotent stem cells to mature megakaryocytes.
Figure 15:
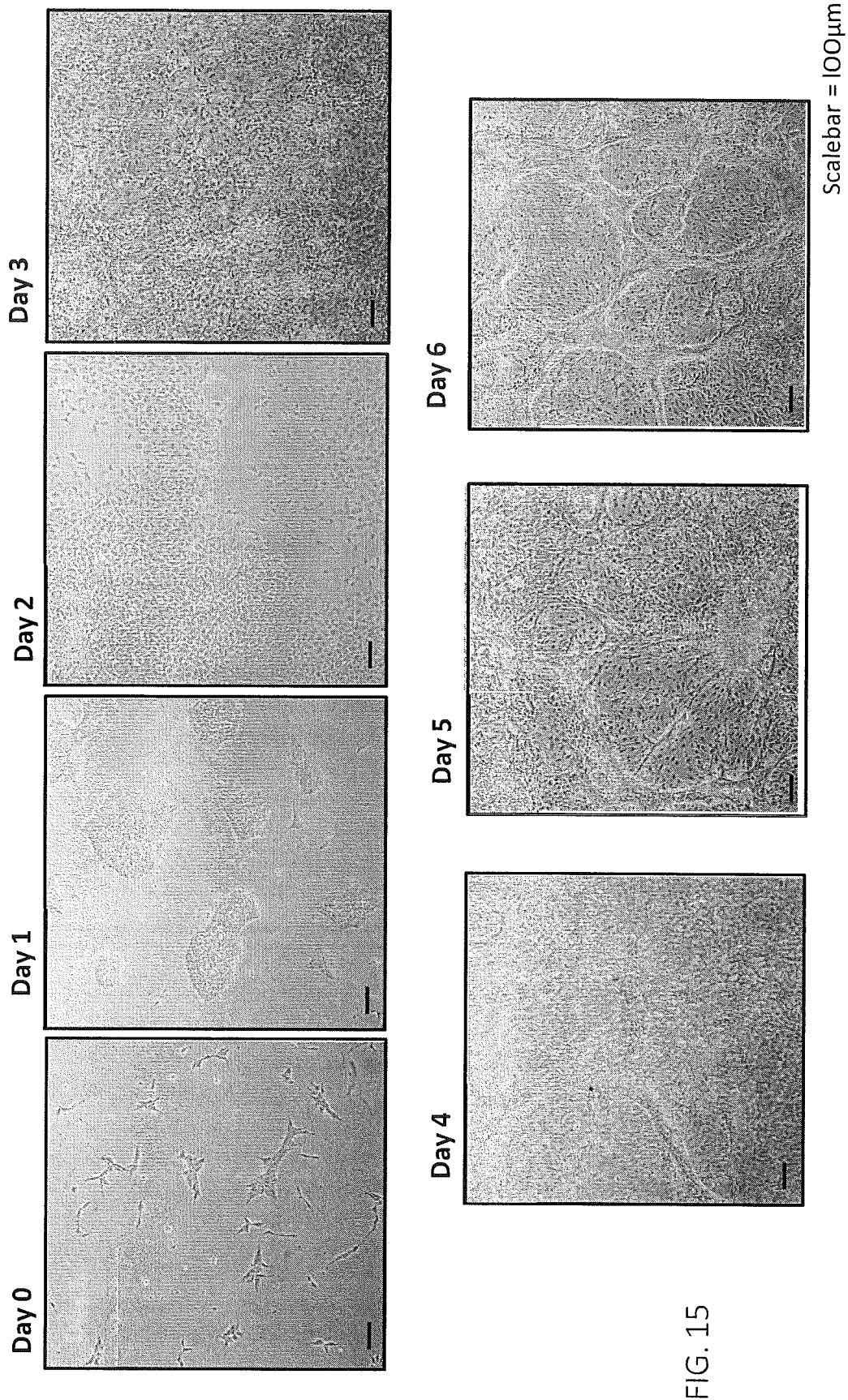
FIG. 15 depicts the morphological changes that occur over 6 days of Phase I differentiation of PBG1 iPSC to hemogenic endothelium on Collagen IV matrix in a 2D culture vessel.
Figures 33A, 33B:
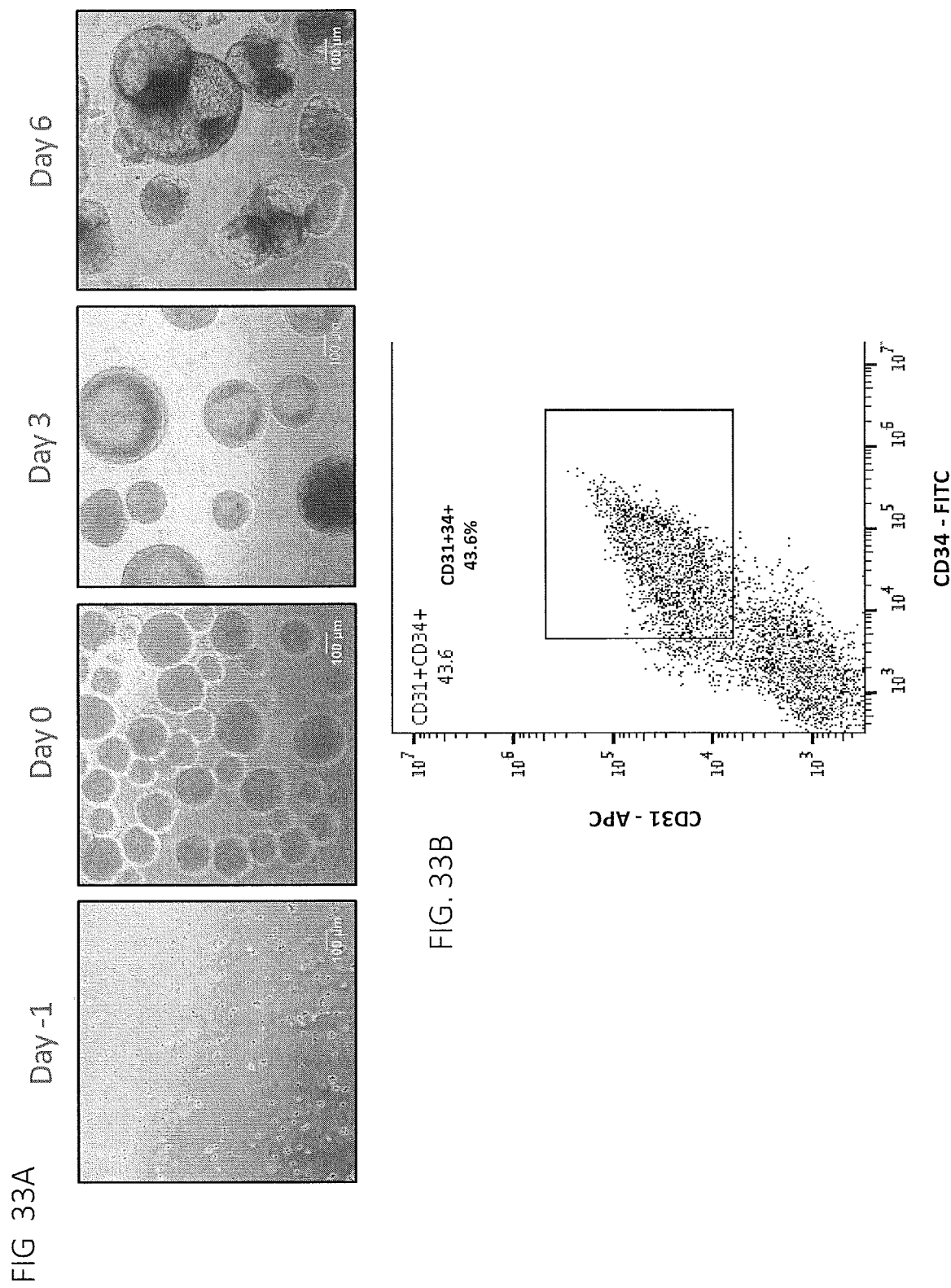
FIG. 33A and FIG. 33B depict Phase 0 and Phase I differentiation initiated with self-aggregating spheroids of PBG1 iPSCs.

In 2D matrix-dependent cultures, by day 2, the morphology of the colonies changes to scattered elongated cell clusters (FIG. 15). By day 5-6, a confluent adherent layer of hemogenic endothelial cells is observed, with some three-dimensional structure within the adherent cell layer (FIG. 15). In matrix-independent 3D cultures, the spheroids grow larger, darker, and less uniform as Phase I progresses (FIG. 33A). Approximately 6 days after initiation of Phase I differentiation, differentiation to hemogenic endothelium is complete. In some embodiments, differentiation can be deemed complete when a confluent adherent layer of hemogenic endothelial cells is observed, with some three-dimensional structure within the adherent cell layer (FIG. 4). To confirm successful Phase I differentiation, a portion of the cells can be harvested as single cells using proteolytic enzymes, collagenolytic enzymes, or combinations thereof such as Accutase® (STEMCELL Technologies, Cat. No. 07920), TrypLE Select™ (Thermo Fisher Scientific, Cat. No. 12563029), or similar reagent known in the art, followed by flow cytometric analysis for the hemogenic endothelium-specific markers CD31 and CD34. In some embodiments, the hemogenic endothelial cells can also express CD309 and CD144 or CD309, CD144, CD140a and CD235a. In some embodiments, the Phase I can be carried out in a stir tank bioreactor to form self-aggregating spheroids.

Phase II. Generation of DetachedMegakaryocytic Progenitors (preMKs) from Hemogenic Endothelial Cells In some embodiments, initiation of megakaryocytic progenitor (Phase II) differentiation can be performed following between 4 and 8 days of Phase I. Briefly, Phase I medium is removed and replaced with an equivalent volume of Phase II medium, such as, for example, STEMdiff™ APEL™2 basal medium (STEMCELL Technologies, Cat. No. 05275). Such Phase II medium can be supplemented with 1 and 200 ng/ml of each of one or more of Stem Cell Factor (SCF) (for example, at 25 ng/ml), Thrombopoietin (TPO) (for example, at 25 ng/ml), Fms-related tyrosine kinase 3 ligand (Flt3-L) (for example, at 25 ng/ml), Interleukin-3 (IL-3) (for example, at 10 ng/ml), Interleukin-6 (IL-6) (for example, at 10 ng/ml), and Heparin (for example, at 5 Units/ml). In some embodiments, the Phase II medium can be further supplemented with UM171, UM729, SR-1, SU6656, or any combinations thereof.

Cells are then incubated for at least 7 and up to 12 or more days at 37° C., 5% $CO_2$, 20% $O_2$. For example, the cells can be incubated for 7, 8, 9, 10, 11, 12, 13, 14, 15, 16, 17 days. In some embodiments, daily partial media exchanges can be performed, with 10-95% of the spent media removed and replaced with equivalent volumes of fresh Phase II media. In some embodiments, additional volumes of fresh media can be added with the net effect of increasing the total volume of the culture. In some embodiments, specific media components can be spiked into the culture in lieu of replacement or addition of fresh Phase I media.

Figure 17A:
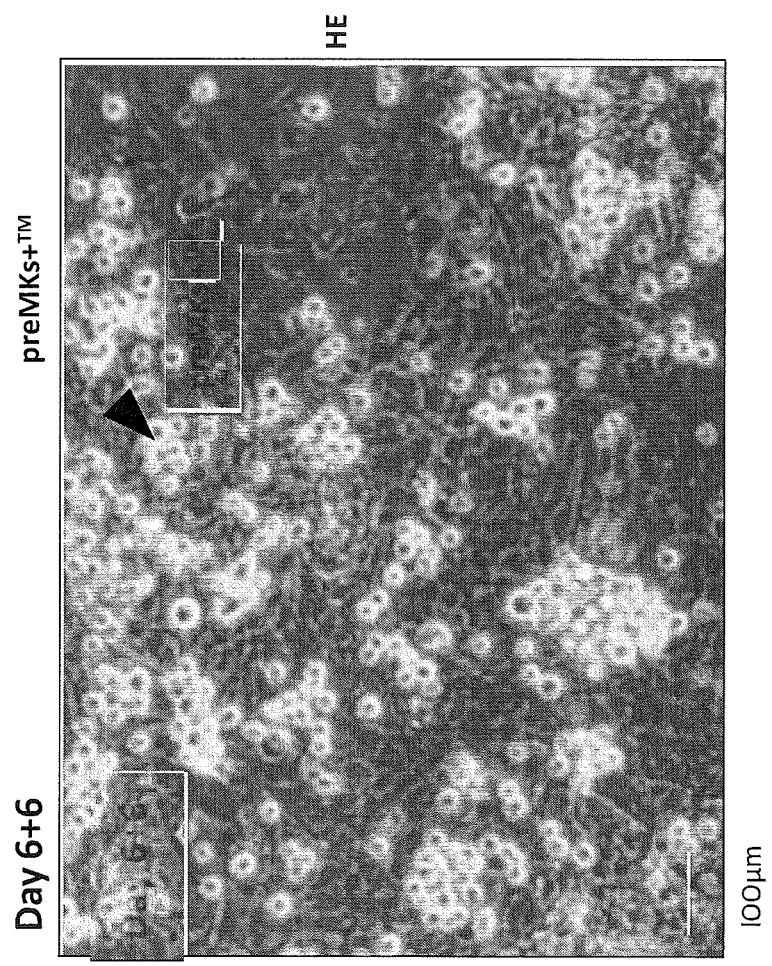
FIG. 17A, FIG. 17B and FIG. 17C depict representative Phase II data from PBG1 differentiation cultures.

Within 2-3 days after initiation of Phase II, small, round, refractile cells appear within the adherent hemogenic endothelial cells and are eventually released into the supernatant (FIG. 17A). These released cells can contain preMKs, as defined by cell surface expression of CD43 and CD41 and lacking expression of CD14. In 2D cultures, floating and weakly attached Phase II cells that appear on top of the adherent cell layer can be harvested daily by gentle rinsing and collection of the medium into conical tubes. A half-media change can be initiated by adding half the original volume of fresh Phase II medium on top of the rinsed adherent cell layer. An aliquot of the collected cells in medium can be removed for viable cell enumeration and biomarker analysis by flow cytometry. The remainder of the cells can then be centrifuged at 200×g for 5 minutes. Following centrifugation, a media change can be completed by adding back half the original volume of supernatant to the adherent cell layer. In matrix-independent 3D cultures, released cells can be harvested by pausing agitation to allow the spheroids to settle to the bottom of the vessel, then collecting up to 90% of the media, along with the suspension cells, into tubes (e.g. conical tubes) for centrifugation. Half the original volume of fresh media can then be added to the vessel, and topped up with conditioned media from the supernatant of the centrifuged cells. In some embodiments, additional volumes of fresh media can be added with the net effect of increasing the total volume of the culture. In some embodiments, specific media components can be spiked into the culture in lieu of replacement or addition of fresh Phase II media. The remainder of the supernatant is discarded and the preMK-containing cell pellet can be stored at −180° C. in Cryostor 10 cryopreservation media, or transitioned directly into Phase III. Megakaryocytic progenitors collected during Phase II are small, round, refractile cells that express CD43 and CD41 and lack the expression of CD14.

Phase III. Generation of Mature Megakaryocytes (MK) from Megakaryocytic Progenitors In some embodiments, differentiation of mature megakaryocytes can be initiated using PSC-derived preMKs, generated as described above. Fresh or thawed megakaryocytic progenitors can be seeded onto a non-adherent surface in Phase III medium, comprising, for example, StemSpan™-ACF. Non-adherent surfaces refer to surfaces such that the majority of cells are not intended to stick or cling to such surfaces, but instead remain mostly in suspension. For example, such surface can be made of "ultra-low adherence plastic" or may not be coated with extracellular matrix proteins to prevent or minimize adhesion of cells to the surface. In some embodiments the Phase III medium can be supplemented with between 0 and 200 ng/ml each of one or more of TPO (for example, at 25 ng/ml), SCF (for example, at 25 ng/ml), IL-6 (for example, at 10 ng/ml), IL-9 (for example, at 10 ng/ml), and Heparin (for example, at 5 units/ml). In some embodiments, the Phase III medium can also be supplemented with UM171, UM729, SR-1, SU6656, or any combinations thereof.

Cells can then be incubated at between 37° C. and 40° C. (for example, 39° C.), between 5 and 20% $CO_2$ (for example, 7%-10%), and between 5 and 20% $O_2$ for up to 5 days. In some embodiments, partial daily media exchanges are performed, with 10-95% of the spent media removed and replaced with equivalent volumes of fresh Phase III media. In some embodiments, the non-adherent surface is a 6-well ultra-low-adherent plate. In some embodiments, the non-adherent surface is a gas permeable membrane (such as the G-Rex C)). In some embodiments, the non-adherent surface is a cell culture bag or vessel with gentle agitation.

In some embodiments, during Phase III, the megakaryocytic progenitors can differentiate into mature MKs within several days. In some embodiments, cells that are initially uniformly small, round, and refractile (FIG. 21) begin to increase in size and ploidy by day 2-4 (FIG. 20). Simultaneously, proplatelet-producing MKs can be readily observed (FIG. 20). By 3-4 days of Phase III, the proportion of $CD61^+$ (megakaryocytic lineage) cells co-expressing the mature MK markers CD42a and CD42b increases dramatically and can reach levels as high as 80-90%, depending on the starting hi SPC cell line (FIG. 21). By day 4-5 of Phase III, platelets are released by mature MKs into the culture medium. These platelets can be collected, quantified, and assessed by flow cytometry and electron microscopy, confirming their identity as bona fide platelets (FIG. 45).

3D Systems

Packed Bed Bioreactor

In some embodiments, a 3D scalable packed-bed bioreactor may be used for the production of one or more of preMKs, megakaryocytes, platelets, or megakaryocytes and platelets. In some embodiments, the packed bed bioreactor can be used for the Phase I and Phase II culture. For example, the packed-bed reactor can be used for differentiation of PSCs to hemogenic endothelium cells, followed by the production of preMKs. The packed-bed reactor carriers may be either micro-sized or macro-sized and can be formed from biocompatible plastics, metals, glass, or natural materials, such as alginate. In some embodiments, the carriers are formed from PTFE in the shape of Raschig rings, for example 1 mm Raschig rings. In some embodiments, the carriers can be coated with a matrix as described above. In some embodiments, the carriers may be coated with Laminin, such as a recombinant human protein Laminin 521. In some embodiments, pluripotent cells can be seeded as clumps onto the carriers. In some embodiments, media can be removed and replaced with Phase I media, with daily media exchanges. In some embodiments, during Phase I, the pluripotent cells can exhibit growth areas on the inside of the carriers in the packed bed reactor. In some embodiments, initial differentiation of pluripotent cells to hemogenic endothelium (i.e. Phase I of directed differentiation), as well as the further differentiation and release of preMKs (i.e. Phase II of directed differentiation) can occur in the same vessel. For example, a packed-bed bioreactor can comprise Laminin-521 coated macrocarriers seeded with pluripotent cells, for example PBG-1 iPSCs. The packed-bed can then be exposed to a continuous flow of media to enable Phase I differentiation to hemogenic endothelium. After percolating through the packed-bed, the media can be circulated through a conditioning chamber, where fresh media components can be added, and oxygen/$CO_2$ concentrations can be adjusted via sparging or other means before the media can be recirculated to the cells.

At the completion of Phase I, the media can be switched to allow Phase II differentiation and production and release of preMKs. Appropriately sized and shaped carriers such as the 1mm Raschig rings can enable sufficient media flow and channel width to enable the released cells to percolate through the packed bed and out of the reactor for collection and cryostorage. In some embodiments, this design can decrease the shear forces experienced by the cells, can allow for efficient media usage due to its perfusion based design, and can enable the continuous collection of preMKs as they are released.

Self Aggregating Spheroids in Stir Tank Bioreactor

In some embodiments, certain process steps may be carried out using a scalable 3D solution, which can involve performing differentiations using self-aggregating spheroids suspended in stirred or shaken vessels. (FIG. 32). In some embodiments, such vessels can include low-adherent surfaces or non-adherent surfaces, that is, surfaces coated with hydrophilic or neutrally charged coatings to inhibit specific and nonspecific cell immobilization on the surface, forcing cells into a suspended state. Pluripotent cells can be dissociated into single cells and resuspended in pluripotency maintenance media. In some embodiments, the maintenance medium can be supplemented with a Rock Inhibitor, such as, H1152 or other ROCK inhibitor. The pluripotent cells can then be incubated in a low adherent or non-adherent vessel and subjected to agitation in standard culture conditions (for example, 37 C, 5% CO2, 20% O2). In some embodiments to provide agitation, the incubation vessel can be placed on an orbital shaker, or a shaker flask or spinner flask with constant agitation, or a controlled stir tank bioreactor can be used.

Within 24 hours, the pluripotent cells can self-aggregate to form spheroids approximately 50-150 um in diameter. As agitation is paused, the spheroids can settle to the bottom of the vessel.

Media can then be exchanged with Phase I differentiation media to promote the differentiation towards hemogenic endothelium, and agitation can be resumed, with incubation in hypoxic conditions (for example, 37° C., 5% CO2, 5% O2). Media exchanges can be performed on a regular basis (for example, daily) during which time the spheroids can grow larger and develop characteristic structure and shape. For example, as shown in FIG. 33A, the spheroids can be cultured for a total of 6 days (4 days in 37° C., 5% CO2, 5% O2, followed by 2 days in 37° C., 5% CO2, 20% O2). As shown in FIG. 33A, at day 6 the spheroids are larger, darker and have an irregular surface.

To transition to Phase II, agitation can be paused and the spheroids can be allowed settle to the bottom of the vessel. Media can then be exchanged with Phase II differentiation media to promote the differentiation and release of suspension cells. On a regular basis thereafter (for example, daily), suspension cells can be collected and a partial media exchange can be performed. The media can be collected, and centrifuged. Approximately half the working volume of fresh Phase II differentiation media can be added to the spheroids, along with a sufficient volume of conditioned media (i.e. supernatant post-centrifugation) to restore the original working volume. The cell pellets can be cryopreserved or transferred to Phase III for maturation to mature MKs.

Upon transition to static Phase III cultures, preMKs from 3D self-aggregating spheroid cultures can generate similar MK purities as preMKs from 2D culture systems. Furthermore, Phase III differentiation cultures generated from 3D self-aggregating spheroid cultures can contain cells that increased dramatically in size and are able to generate proplatelets, consistent with their identity as bona fide megakaryocytes.

Transition to Scalable System for Phase III

In some embodiments, as noted above, fresh or thawed megakaryocytic preMKs can be seeded onto a low-adherent or non-adherent surface in Phase III medium. In some embodiments, such non-adherent surface can be a gas permeable membrane (such as the G-Rex®). In some embodiments, the low-adherent or non-adherent surface is a cell culture bag or vessel with gentle agitation. In either case, preMKs (either freshly harvested from Phase II culture, or thawed from cryopreserved stocks) are suspended in Phase III media at a density of 0.5-10 million per ml, and introduced into the vessel. For example, the preMKs can be at density of 1 to 1.5 million per ml, of 1 to 2 million per ml, of 1 to 3 million per ml, of 1 to 4 million per ml, of 2 to 5 million per ml, of 2 to 6 million per ml, of 3 to 7 million per ml, of 3 to 8 million per ml, of 5 to 9 million per ml, or of 8 to 10 million per ml. The cells are cultured for a total of 1-5 days (for example, 3 days) to enable differentiation into mature MKs. In some embodiments, daily half media exchanges are performed, with 10-95% of the spent media removed and replaced with equivalent volumes of fresh Phase III media. At the end of the Phase III cultures, the resulting cells are increased in size and ploidy, and exhibit a host of features indicative of mature megakaryocytes (as for example, shown in FIGS. 34 to 42 and described below).

Megakaryocytes and Products Thereof

In some embodiments, the present disclosure provides a megakaryocytic progenitor, a megakaryocyte, preplatelet, proplatelet or a platelet derived in vitro from a PSC cell or cell line. According to aspects of the present disclosure, the megakaryocytic progenitor, a megakaryocyte, preplatelet, proplatelets or a platelet derived from a PSC cell or cell line are produced using the method of U.S. Pat. No. 9,763,984 or the bioreactor as disclosed in International Application No. PCT/US2018/021354, which are incorporated herein by reference in their entireties.

In some embodiments, the present disclosure provides an isolated population of cells comprising the megakaryocyte or megakaryocytic progenitor.

In some embodiments, the present disclosure provides a composition containing a megakaryocyte or megakaryocytic. In some embodiments of the present disclosure, the composition comprising megakaryocyte, megakaryocytic progenitor or products thereof is disclosed.

According to some embodiments of the present disclosure, the megakaryocyte, megakaryocytic progenitor or products thereof are homogenous in shape, size and/or phenotype. It should be appreciated that the megakaryocyte, megakaryocytic progenitor or products thereof of the present disclosure may comprise a variability in biomarker expression, size, ploidy, number and purity that is characteristically different than the variability in corresponding human cells. In some embodiments, such variability can be significantly lower. In some embodiments, the cell populations may be created to have a desired variability, which may be lower or higher than that of the naturally-occurring cells.

In some embodiments, megakaryocytic progenitors (pre-MKs) are characterized by the expression of the markers CD43 and CD41, and the lack of CD14 (i.e. CD14$^-$, CD41$^+$, CD43$^+$). Additional expression of CD42b may indicate that the megakaryocytic progenitor is in the process of final maturation towards mature megakaryocytes. In certain embodiments, megakaryocytic progenitors generated in differentiation cultures are non-adherent and may float freely in the culture medium.

In some embodiments, the instant megakaryocytes are one or more of CD42a$^+$, CD42b$^+$, CD41$^+$, CD61$^+$, GPVI+, and DNA$^+$. In some embodiments, the instant megakaryocytes are one or more CD42a$^+$, CD42b$^+$, CD41$^+$, CD61$^+$, and DNA$^+$. In some embodiments, the instant megakaryocytes are one or more of CD42b$^+$, CD61$^+$, and DNA$^+$.

In some embodiments, the instant megakaryocytes are one or more of CD42a$^+$, CD61$^+$, and DNA$^+$. In some embodiments, the instant megakaryocytes are one or more of CD42a$^+$, CD41$^+$, and DNA$^+$. In some embodiments, the instant megakaryocytes are one or more of CD42b$^+$, CD41$^+$, CD61$^+$, and DNA$^+$. In some embodiments, the instant megakaryocytes are one or more of CD42b$^+$, CD42a$^+$, CD61$^+$, and DNA$^+$. In some embodiments, the instant megakaryocytes are one or more of CD42b$^+$, CD42a$^+$, CD41$^+$, and DNA$^+$. In some embodiments, the megakaryocyte is CD41$^+$CD61$^+$CD42b$^+$ GPVt. In some embodiments, the megakaryocyte is CD41$^+$CD61$^+$CD42a$^+$ GPVt.

In some embodiments, the instant megakaryocyte is CD61$^+$ and DNA$^+$ and has a diameter of about 10-50 µm. In some embodiments, the megakaryocytes produced by the methods described herein have an average size between 10 and 20 µm, between 11 and 19 µm, between 12 and 18 µm, between 13 and 17 µm, between 14 and 16 µm, between 14 and 15 µm. In some embodiments, the megakaryocytes produced by the methods described herein have an average size of 14.5 µm. In some embodiments, the instant megakaryocyte has a diameter of about 10-20 µm. In some embodiments, the instant megakaryocyte has a diameter of about 10-30 µm. In some embodiments, the instant megakaryocyte has a diameter of about 10-40 µm. In some embodiments, the instant megakaryocyte has a diameter of about 10-50 µm. In some embodiments, the instant megakaryocyte has a diameter of about 20-40 µm. In some embodiments, the instant megakaryocyte has a diameter of about 25-40 µm.

In some embodiments, the instant megakaryocytes produced by the methods described herein have a ploidy of 2N-16N. In some embodiments, the instant megakaryocyte has a ploidy of at least 4N, 8N, or 16N. In some embodiments, instant megakaryocytes have ploidy 4N-16N. In some embodiments, the instant megakaryocytes produced by the methods described herein are 16%+/−11.4% of CD61±cells at 72 hours of Phase 111 culture with higher than 4N DNA.

In some embodiments, at least 50% of the megakaryocyte population produced by the methods described herein is $CD61^+$ and $DNA^+$, and has a ploidy of 2N to 16N. For example, the megakaryocytes (i.e. beta-1-tubulin positive Phase III cells) from a representative PBG1 differentiation culture ranged in size from about 9 ┌m to about 27 ┌m, with a median of 15 ┌m. This average size compares similarly with 'normal' megakaryocytes from various bone marrow sources (FIG. 41).

In some embodiments, the isolated population of cells or the composition contains at least 50% of $CD42b^+CD61^+DNA^+$ cells. In some embodiments, the isolated population of cells or the composition contains at least 55% of $CD42b^+CD61^+DNA^+$ cells. In some embodiments, the isolated population of cells or the composition contains at least 65% of $CD42b^+CD61^+DNA^+$ cells. In some embodiments, the isolated population of cells or the composition contains at least 60% of $CD42b^+CD61^+DNA^+$ cells. In some embodiments, the isolated population of cells or the composition contains at least 70% of $CD42b^+CD61^+DNA^+$ cells. In some embodiments, the isolated population of cells or the composition contains at least 75% of $CD42b^+CD61^+DNA^+$ cells. In some embodiments, the isolated population of cells or the composition contains at least 80% of $CD42b^+CD61^+DNA^+$ cells. In some embodiments, the isolated population of cells or the composition contains at least 85% of $CD42b^+CD61^+DNA^+$ cells. In some embodiments, the isolated population of cells or the composition contains at least 90% of $CD42b^+CD61^+DNA^+$ cells. In some embodiments, the isolated population of cells or the composition contains at least 95% of $CD42b^+CD61^+DNA^+$ cells. In some embodiments, the isolated population of cells or the composition contains at least 98% of $CD42b^+CD61^+DNA^+$ cells.

In some embodiments, the isolated population of cells or the composition contains at least 50% of $CD42b^+CD41^+CD61^+DNA^+$ cells. In some embodiments, the isolated population of cells or the composition contains at least 55% of $CD42b^+CD41^+CD61^+DNA^+$ cells. In some embodiments, the isolated population of cells or the composition contains at least 65% of $CD42b^+CD41^+CD61^+DNA^+$ cells. In some embodiments, the isolated population of cells or the composition contains at least 60% of $CD42b^+CD41^+CD61^+DNA^+$ cells. In some embodiments, the isolated population of cells or the composition contains at least 70% of $CD42b^+CD41^+CD61^+DNA^+$ cells. In some embodiments, the isolated population of cells or the composition contains at least 75% of $CD42b^+CD41^+CD61^+$ cells. In some embodiments, the isolated population of cells or the composition contains at least 80% of $CD42b^+CD41^+CD61^+DNA^+$ cells. In some embodiments, the isolated population of cells or the composition contains at least 85% of $CD42b^+CD41^+CD61^+DNA^+$ cells. In some embodiments, the isolated population of cells or the composition contains at least 90% of $CD42b^+$ $CD41^+CD61^+DNA^+$ cells. In some embodiments, the isolated population of cells or the composition contains at least 95% of $CD42b^+CD41^+CD61^+DNA^+$ cells. In some embodiments, the isolated population of cells or the composition contains at least 98% of $CD42b^+CD41^+CD61^+DNA^+$ cells.

In some embodiments, the isolated population of cells or the composition contains at least 50% of $CD42b^+CD42a^+CD61^+DNA^+$ cells. In some embodiments, the isolated population of cells or the composition contains at least 55% of $CD42b^+CD42a^+CD61^+DNA^+$ cells. In some embodiments, the isolated population of cells or the composition contains at least 65% of $CD42b^+CD42a^+CD61^+DNA^+$ cells. In some embodiments, the isolated population of cells or the composition contains at least 60% of $CD42b^+CD42a^+CD61^+DNA^+$ cells. In some embodiments, the isolated population of cells or the composition contains at least 70% of $CD42b^+CD42a^+CD61^+DNA^+$ cells. In some embodiments, the isolated population of cells or the composition contains at least 75% of $CD42b^+CD42a^+CD61^+DNA^+$ cells. In some embodiments, the isolated population of cells or the composition contains at least 80% of $CD42b^+CD42a^+CD61^+DNA^+$ cells. In some embodiments, the isolated population of cells or the composition contains at least 85% of $CD42b^+CD42a^+CD61^+DNA^+$ cells. In some embodiments, the isolated population of cells or the composition contains at least 90% of $CD42b^+CD42a^+CD61^+DNA^+$ cells. In some embodiments, the isolated population of cells or the composition contains at least 95% of $CD42b^+CD42a^+CD61^+DNA^+$ cells. In some embodiments, the isolated population of cells or the composition contains at least 98% of $CD42b^+CD41^+CD61^+DNA^+$ cells.

In some embodiments, the isolated population of cells or the composition contains at least 50% megakaryocytes having ploidy of 4N or greater. In some embodiments, at least 50% megakaryocytes have ploidy 4N-16N. In some embodiments, at least 60% megakaryocytes have ploidy 4N-16N. In some embodiments, at least 70% megakaryocytes have ploidy 4N-16N. In some embodiments, at least 80% megakaryocytes have ploidy 4N-16N. In some embodiments, at least 90% megakaryocytes have ploidy 4N-16N. In some embodiments, the isolated population of cells or composition contains megakaryocytes having a mean ploidy of 4N.

In some embodiments, the isolated population of cells or the composition contains a proplatelet, preplatelet or platelet generated from a megakaryocyte of the present disclosure. In some embodiments, the proplatelet, preplatelet or platelet is a $CD42b^+CD61^+DNA^-$ cell. In some embodiments, the megakaryocyte is produced in vitro by differentiation of hiPSC cell or cell line.

In some embodiments, the megakaryocytes produced by the methods described herein comprise one or more of the following: (a) content of MK granules by immunofluorescence microscopy: PF4 and VFW for alpha-granules, LAMP-1 and serotonin for dense-granules; (b) gene expression data: Oct4−, Nanog−, Sox2−, Zfp42−, Zfpm1+, Nfe2+, Runx1+, Meis1+, Gata1+; (c) have low/no fibrinogen, serotonin, and LDL, and (d) can uptake fibrinogen, serotonin, and LDL when incubated with plasma.

Figure 44:
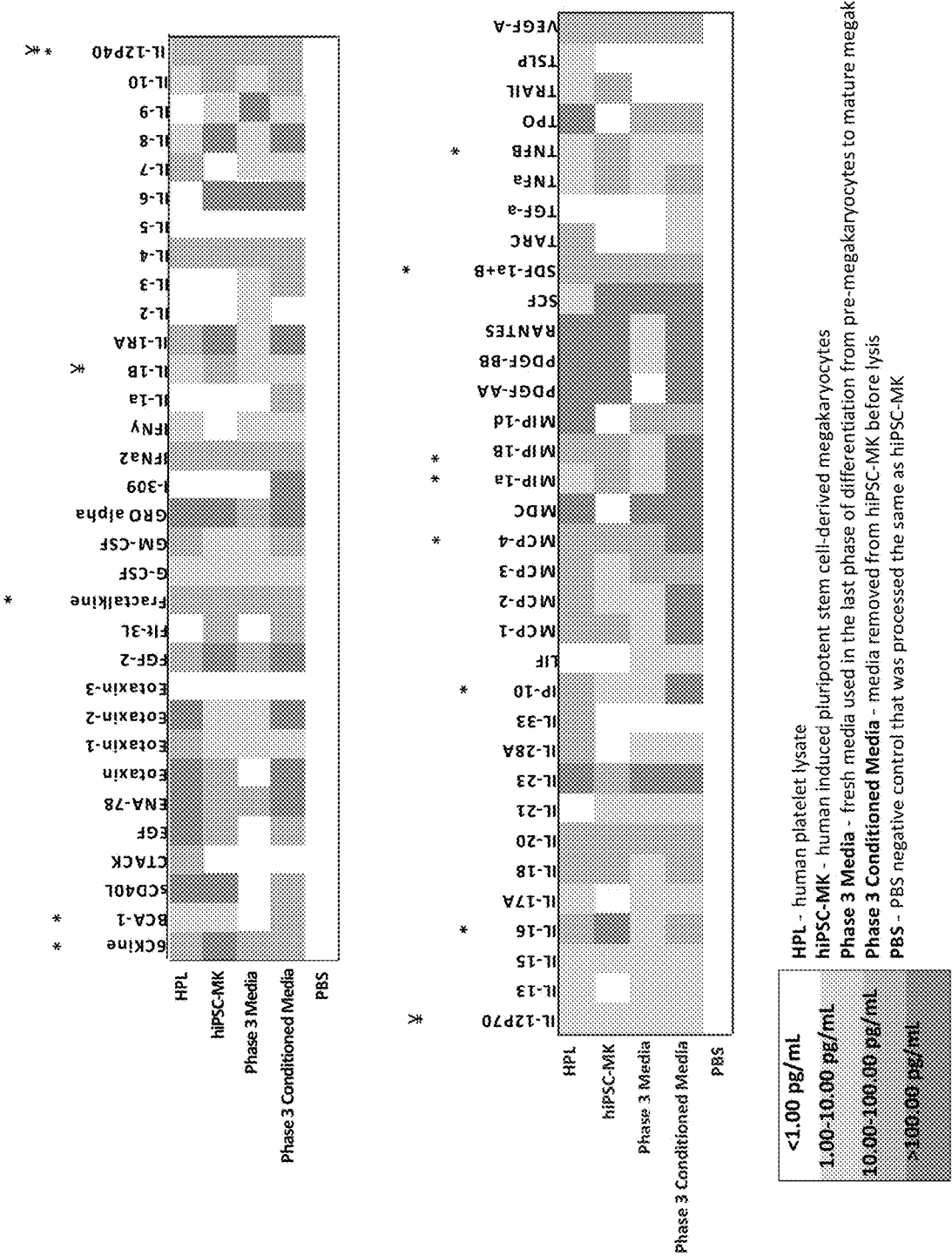
FIG. 44 provides a comparison of presence or absence and concentration range of various factors in hiPSC-MK lysate of megakaryocytes derived by a method of the present disclosure and certain controls.

In some embodiments, the megakaryocytes produced by the methods described herein have a characteristic expression profile of growth factors, cytokines, chemokines, and related factors (FIG. 44). In some embodiments, the present disclosure provides a composition or pharmaceutical composition comprising the instant megakaryocytes that can include factors such as platelet derived growth factor isoforms PDGF-AA or PDGF-BB, vascular endothelial growth factor (VEGF), epidermal growth factor (EGF), basic fibroblast growth factor (FGF-2), hematopoietic growth factors Flt3L, G-CSF, GM-CSF, interleukins (IL-1RA, IL-8, or IL-16), CXC chemokine family members CXCL1 (GRO alpha) or CXCL12 (SDF-1), TNF superfamily members sCD40L or TRAIL, or CC chemokine family members CCL5 (RANTES), CCL11 (Eotaxin-1), CCL21 (6CKine) or CCL24 (Eotaxin-2). In some embodiments, the present disclosure provides a composition or pharmaceutical composition comprising a lysate of instant megakaryocytes. Such lysates can be prepared by any methods known in the art, such as by breaking down of the membrane of preMKs or MKs by viral, enz*vinie*, or osmotic mechanisms that compromise its integrity. The lysates, in some embodiments, may include additional agents or be prepared in different compositions (liquid, paste etc.) depending on the needs of specific applications. In some embodiments, such compositions can include factors such as platelet derived growth factor isoforms PDGF-AA or PDGF-BB, vascular endothelial growth factor (VEGF), epidermal growth factor (EGF), basic fibroblast growth factor (FGF-2), hematopoietic growth factors Flt3L, G-CSF, GM-CSF, interleukins (IL-1RA, IL-8, or IL-16), CXC chemokine family members CXCL1 (GRO alpha) or CXCL12 (SDF-1), TNF superfamily members sCD40L or TRAIL, or CC chemokine family members CCL5 (RANTES), CCL11 (Eotaxin-1), CCL21 (6CKine) or CCL24 (Eotaxin-2).

Methods of Use

In some embodiments, the instant preMKs and MKs and their components can be a source of growth factors, such as human growth factors. In some embodiments, such growth factor can be can be used for cell culture, tissue regeneration, wound healing, bone regeneration, cosmeceuticals, and hemostatic bandages. In some embodiments, the instant megakaryocytes or their lysate or compositions thereof can be used in cell culture. In some embodiments, the instant megakaryocytes or their lysate or compositions thereof can be used as a cosmeceutical. In some embodiments, the instant megakaryocytes or their lysate or compositions thereof can be used as a therapeutic agent. For example, the instant megakaryocytes or their lysate or compositions thereof can be used increase the expansion of cells ex vivo, improves bone marrow regeneration in vivo, increase tissue regeneration and vascularization and increases the survival rates of animals in radiation studies.

In some embodiments, the instant preMKs and MKs can be used for generating platelets to support current transfusions needs (e.g. Surgery, chemotherapy, pregnancy/birth, trauma). National defense and security initiatives are a high priority within the United States and represent a large potential market for MK and resulting products, as a radiation countermeasure. Radiation exposure, such as would occur following a nuclear accident or attack, inhibits platelet production. A large radiological event would trigger an immediate demand for platelets that would deplete existing local inventory to treat emergency trauma, followed by a sustained demand for platelets in survivors 6+ days post-exposure. National strategic stockpiles of platelets will become very important as our military's preparedness gap shifts from the front lines to the 24-48 hours post-incident when affected populations become thrombocytopenic. The United States does not maintain an inventory of platelets in the Strategic National Stockpile and there are no licensed therapeutics that immediately increase platelet counts. The pre-MK and Mks according to some embodiments, can be used for on-demand platelet production. The ability to bank pre-MKs for an extended period of time and develop on-demand hiPSC-platelet production capabilities will enable the establishment of a strategic national stockpile of hiPSC-platelets that will be critical to meeting this projected need.

Autologous platelet-rich plasma (PRP) supplemented medium has been shown to nurture microvascular endothelial cells to improve preservation of vascular integrity in organs perfused for transplantation. Platelets store bioactive factors in secretory granules, which they acquire from megakaryocytes. Contents include various chemokines and growth factors, such as platelet derived growth factor isoforms (PDGF-AA, -AB and -BB), transforming growth factor-b (TGF-b), insulin-like growth factor-1 (IGF-1), brain derived neurotrophic factor (BDNF), vascular endothelial growth factor (VEGF), epidermal growth factor (EGF), basic fibroblast growth factor (bFGF or FGF-2), hepatocyte growth factor (HGF), connective tissue growth factor (CTGF) and bone morphogenetic protein 2, -4 and -6 (BMP-2, -4, -6). Human platelet lysate dramatically increases the expansion of cells ex vivo, improves bone marrow regeneration in vivo, and increases the survival rates of animals in radiation studies. In some embodiments, the present disclosure provides a composition or pharmaceutical composition comprising a lysate of a proplatelet, preplatelet or platelet generated from the instant megakaryocytes, wherein such compositions can include factors such as platelet derived growth factor isoforms PDGF-AA or PDGF-BB, vascular endothelial growth factor (VEGF), epidermal growth factor (EGF), basic fibroblast growth factor (FGF-2), hematopoietic growth factors Flt3L, G-CSF, GM-CSF, interleukins (IL-1RA, IL-8, or IL-16), CXC chemokine family members CXCL1 (GRO alpha) or CXCL12 (SDF-1), TNF superfamily members sCD40L or TRAIL, or CC chemokine family members CCL5 (RANTES), CCL11 (Eotaxin-1), CCL21 (6CKine) or CCL24 (Eotaxin-2).

Kits

The disclosure provides kits comprising a megakaryocyte or differentiated cell of the disclosure. In one embodiment, the kit includes a composition comprising an isolated megakaryocyte. In particular embodiments, the disclosure provides kits for differentiating, culturing, and/or isolating a megakaryocyte of the disclosure or precursor thereof. In certain embodiments, the disclosure provides kits for producing platelets.

In some embodiments, the kit comprises a sterile container which contains a cellular composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired, the kit is provided together with instructions for generating the megakaryocyte. The instructions will generally include information about the conditions and factors required differentiating, culturing, and/or isolating megakaryocytes or precursors thereof. In some embodiments, instructions for producing platelets are included. The instructions may be printed directly on the container (when present), or as a label applied to the container, or as a separate sheet, pamphlet, card, or folder supplied in or with the container.

The practice of the present disclosure employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the disclosure, and, as such, may be considered in making and practicing the disclosure. Particularly useful techniques for particular embodiments will be discussed in the sections that follow.

The following examples are put forth so as to provide those of ordinary skill in the art with a complete disclosure and description of how to make and use the assay, screening, and therapeutic methods of the disclosure, and are not intended to limit the scope of what the inventors regard as their disclosure.

EXAMPLES

Figure 2:
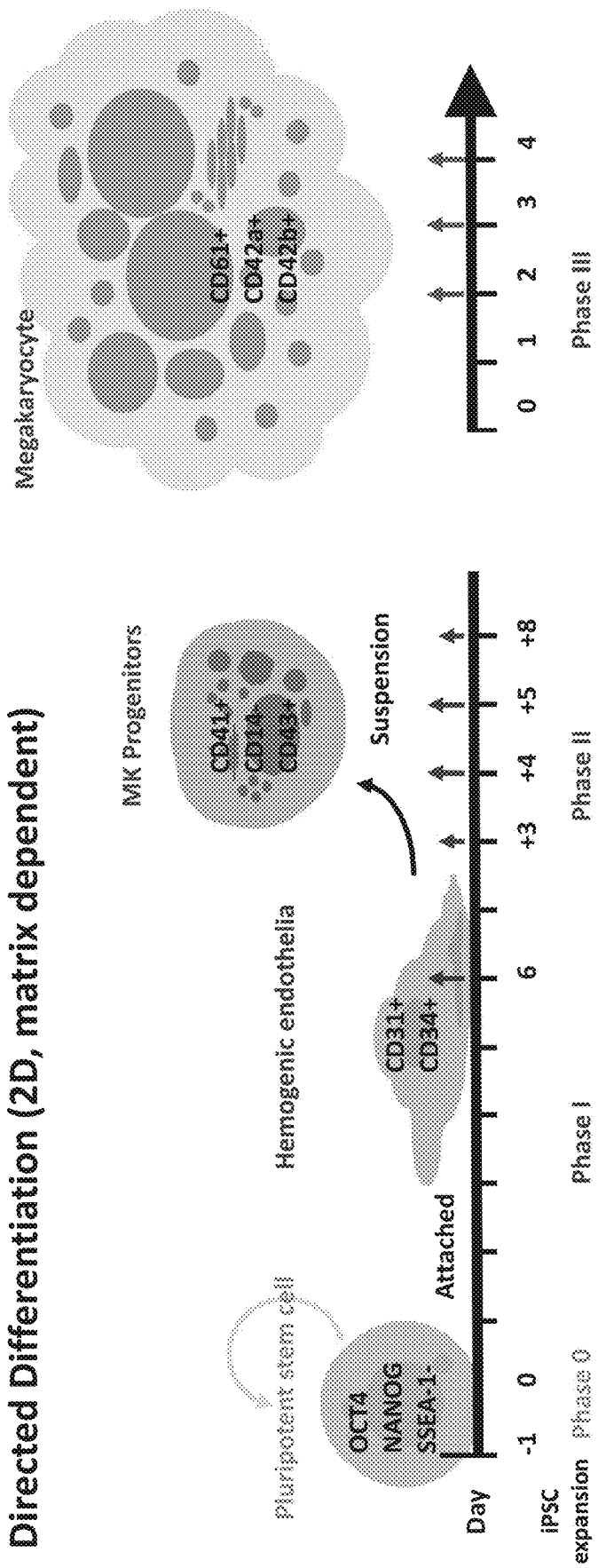
FIG. 2 depicts exemplary directed differentiation protocol of a pluripotent stem cell into a megakaryocyte in a 2D, matrix-dependent system such as a cell culture plate or flask.

Example 1. Extended Production of Megakaryocytic Progenitors, Megakaryocytes and Platelets from Clinical Grade hiPSC Cell Lines Clinical grade hiPSC cell lines were studied for their potential to differentiate into megakaryocytes using the directed differentiation protocol in FIG. 2, which is a schematic showing the time course of differentiation of pluripotent stem cells into megakaryocytes, with each phase of differentiation (Phase 0, I, II, III) indicated. Cell types and cell markers in Phases 0-III are depicted above the timeline. Culture conditions, including media composition, matrix, temperature and gas conditions, are shown below the timeline.

Different iPSC lines are functionally distinct and in order to truly optimize a differentiation protocol it is important to identify the optimal clinical grade cell line for the process. Three clinical grade hiPSC cell lines, termed PBG1, PBG2, and PBG3, were obtained. PBG1 was obtained from the NINDS Human Cell and Data Repository (NHCDR) depository at NINDS(National Institute of Neurological Disorders and Stroke)/NIH(National Institutes of Health). PBG1 (NINDS ID: LiPSC-Gr1.1) was derived from male $CD34^+$ cord blood (Lonza). PBG2 and PBG3 were obtained from Fujifilm-Cellular Dynamics International (F-CDI). PBG2 and PBG-3 were derived, respectively, from male and female adult blood cells (F-CDI MyCells iPSC ID numbers: 21525 and 21526).

Figure 5:
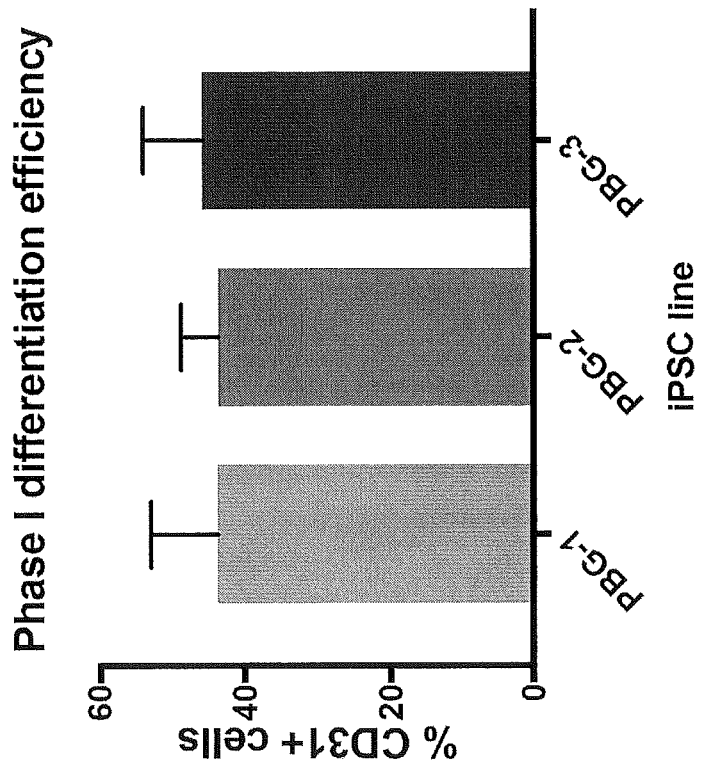
FIG. 5 is a graph depicting the average CD31+ differentiation efficiency at the end of Phase I for directed differentiation of PBG1, PBG2, and PBG3 iPSC lines.
Figure 6A:
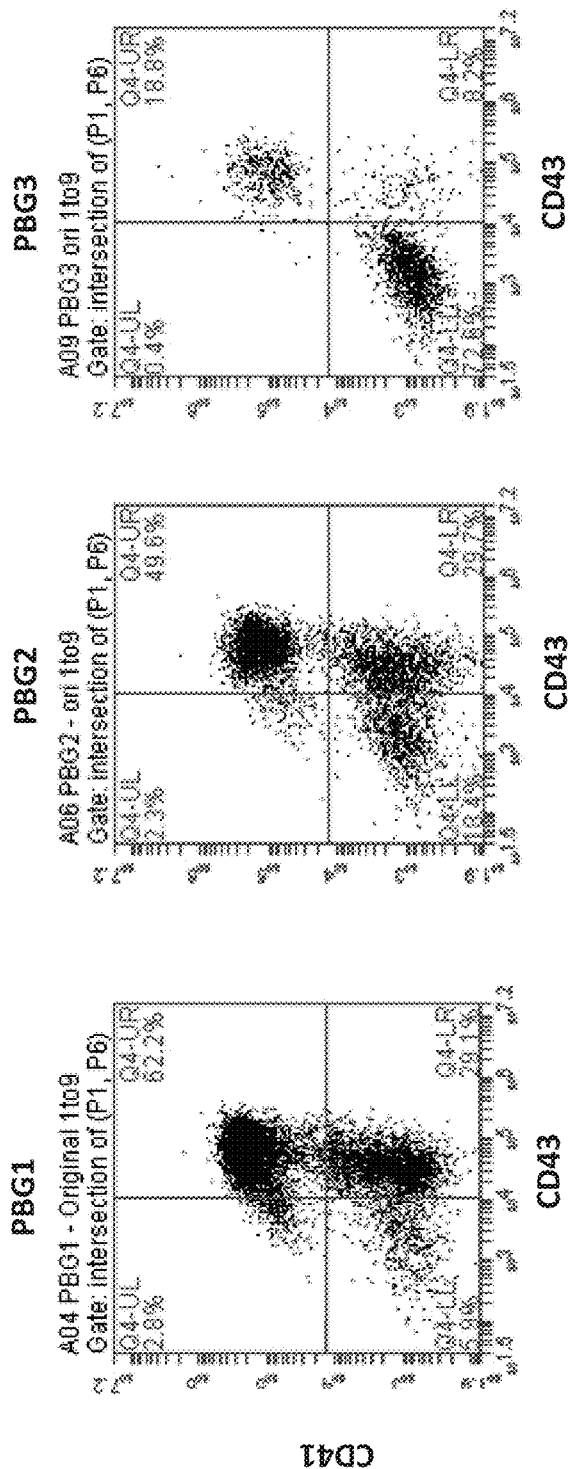
FIG. 6A, FIG. 6B, and FIG. 6C show the purity and yields of megakaryocytic progenitors (CD43+CD41+) generated during Phase II of directed differentiation of PBG1, PBG2, and PBG3 iPSC lines.
Figure 6B:
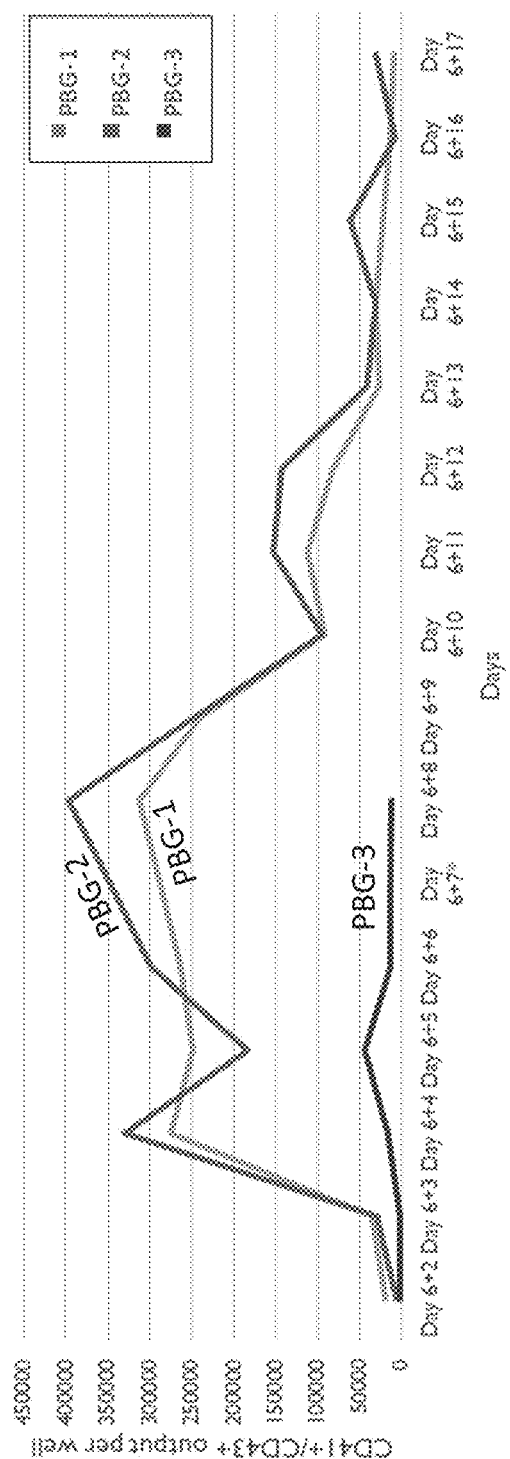
Figure 6C:
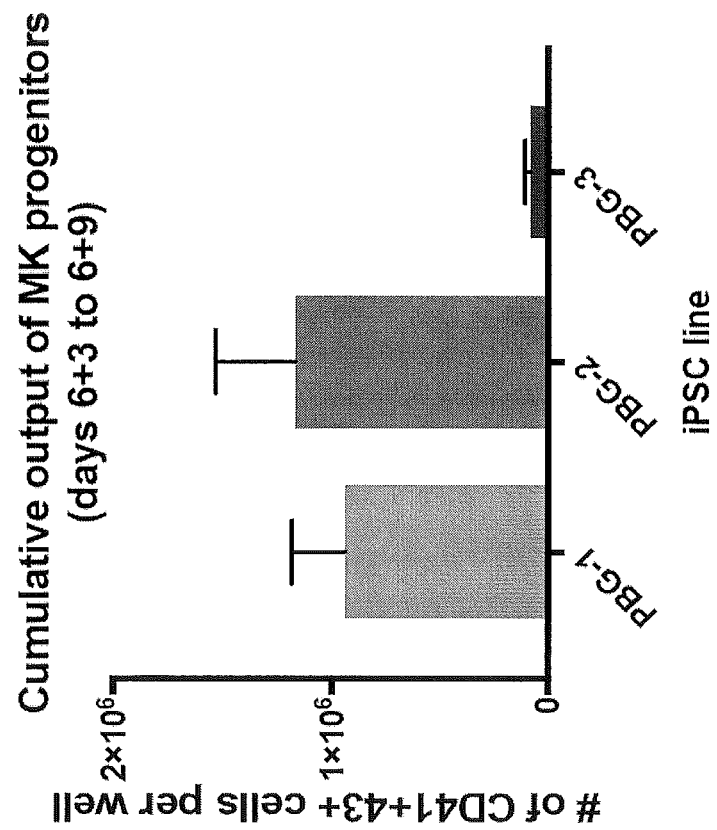
Figure 7B:
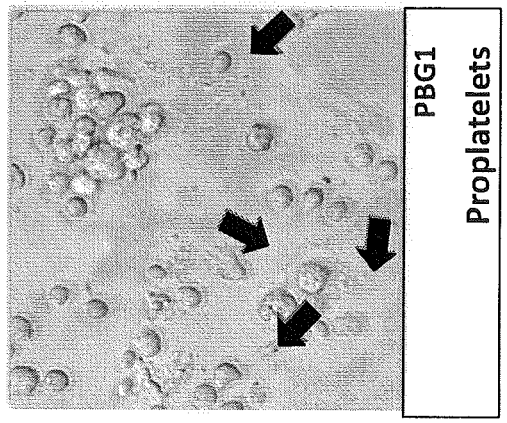
FIG. 7A, FIG. 7B, and FIG. 7C depict Phase III, the final phase of the directed differentiation protocol, that ultimately generates mature megakaryocytes.
Figure 7C:
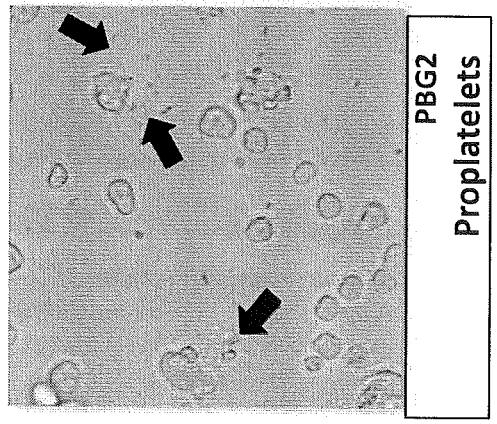
Figure 7A:
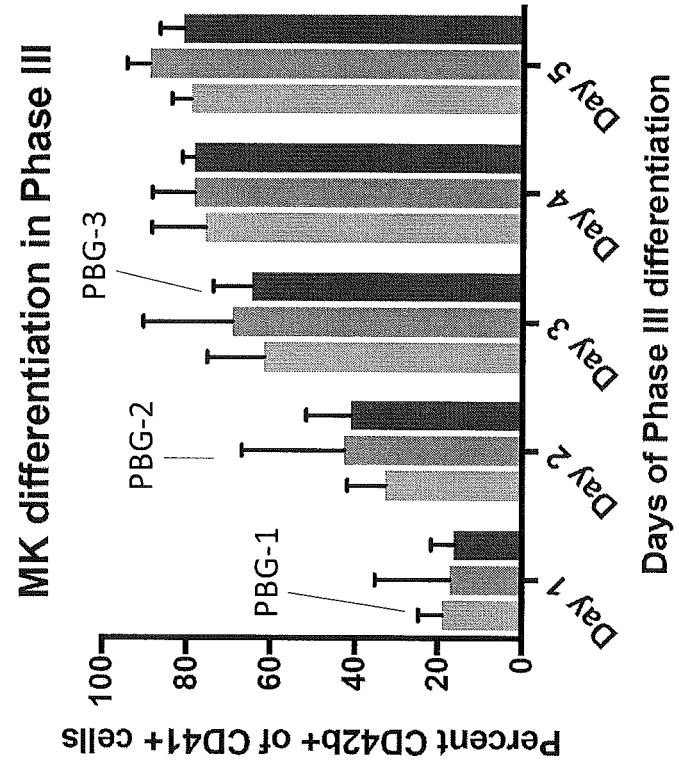
Figure 8E:
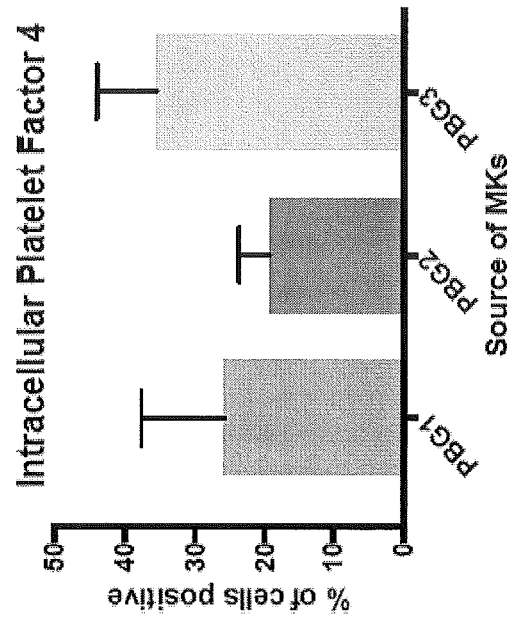
Figure 8D:
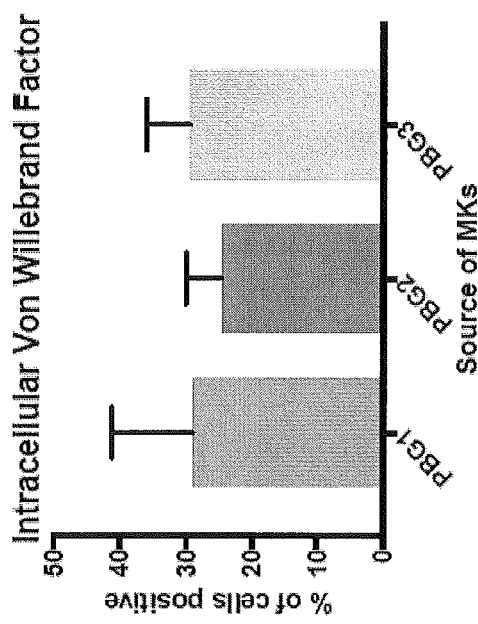
Figure 9A:
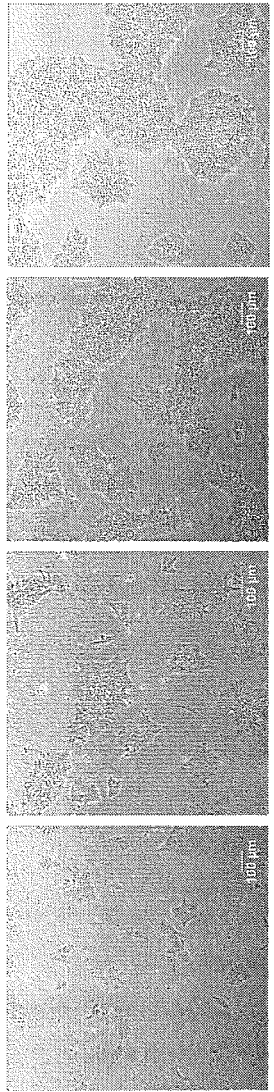
FIG. 9A, FIG. 9B, and FIG. 9C depict expansion of pluripotent PBG1 cells on recombinant vitronectin using various growth medias.
Figure 9B:
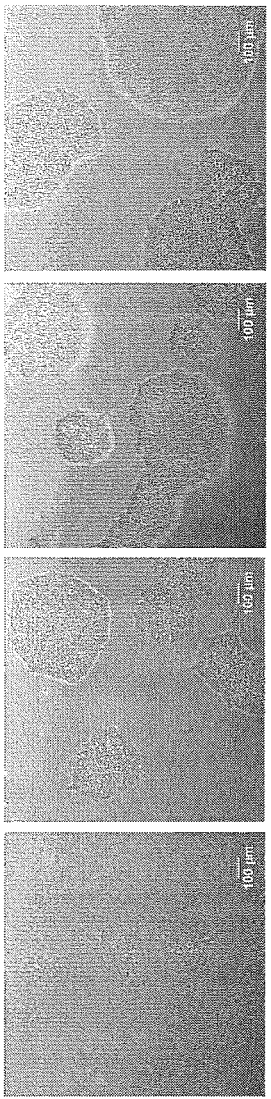
Figure 9C:
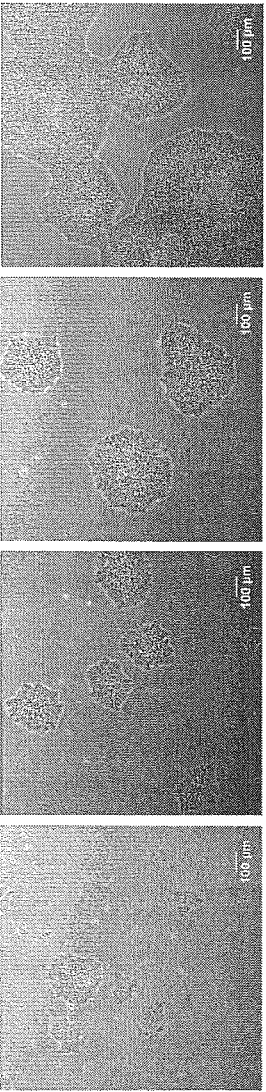

Prior to initiation of differentiation, all three hiPSC lines formed characteristic colonies when grown on Vitronectin with Essential 8 media (FIG. 3A) and showed expression of the pluripotency biomarkers OCT4 and NANOG (FIG. 3B, FIG. 13A). The three clinical grade hiPSC cell lines were directed to differentiate to megakaryocytes using a multi-phase protocol summarized in FIG. 2. The cells were observed at various time points during directed differentiation (FIGS. 4A-4D). Differentiation efficiency during Phase I was initially observed by monitoring expression of $CD31^+$, a marker of hemogenic endothelium (FIG. 5). Differentiation efficiency was similar for 3 hiPSC cell lines during Phase I. Without being bound by theory, differences seen in megakaryocyte output/quality later during differentiation process did not always correlate with differentiation efficiency in Phase I. In Phase II, further differentiation towards megakaryocytic progenitors was observed by monitoring the production of $CD41^+CD43^+$ cells (FIG. 6A). Notably, for some of the clinical grade cell lines, the production of megakaryocytic progenitors during Phase II extended longer (up to 17 days) compared to previous methods using different hiPSC cell lines (FIG. 6B). Cumulative yields were especially robust for PBG-1 and PBG-2 iPSCs and showed some variability between independent differentiations (FIG. 6C). When the cells were transitioned to Phase III of the directed differentiation protocol, expression of $CD42b^+$ increased over Days 1-5 and at Day 4-5 the percentage of $CD41^+$ cells expressing $CD42b^+$ was at least about 80% (FIG. 7A). Phase III cells obtained from the 3 clinical grade iPSC lines were analyzed by light microscopy, immunofluorescence microscopy, and electron microscopy, which revealed that PBG1 and PBG2 exhibited features consistent with that of mature megakaryocytes, including size, morphology, proplatelet extensions, megakaryocyte-specific protein expression, and ultrastructure (FIGS. 7B-7C, FIGS. 8A-8E).

Example 2. Large-Scale Expansion of Pluripotent PBG-1 Cells

Figure 12A:
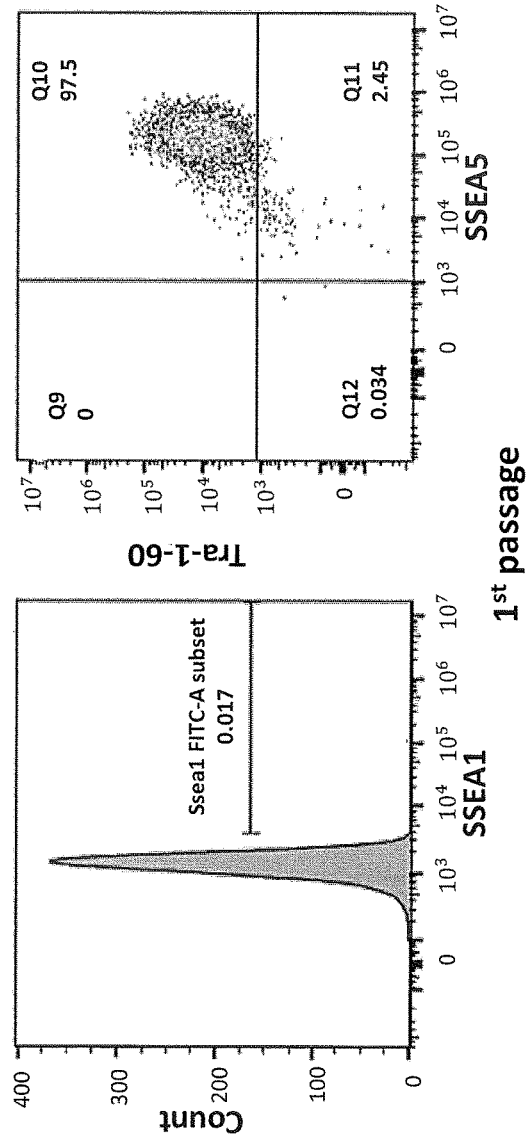
FIG. 12A and FIG. 12B depict flow cytometry data assessing expression of the pluripotency markers Tra-1-60, SSEA5, and the differentiation marker SSEA1 on PBG1 cells expanded in self-aggregating spheroid cultures in a 3D stir tank (matrix free).
Figure 12B:
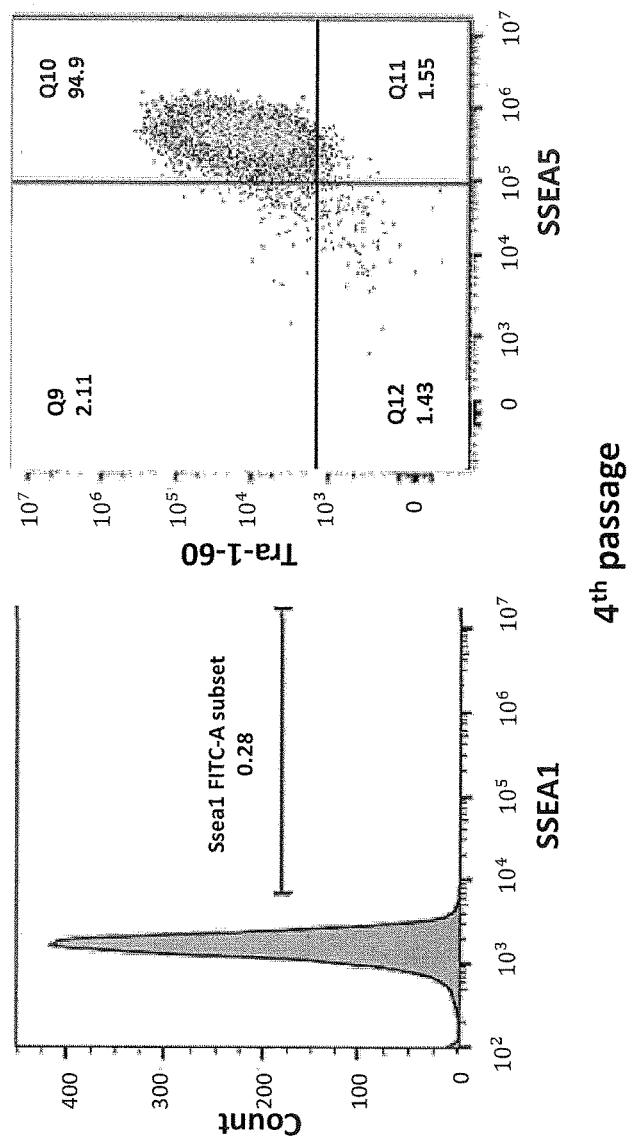
Figure 14:
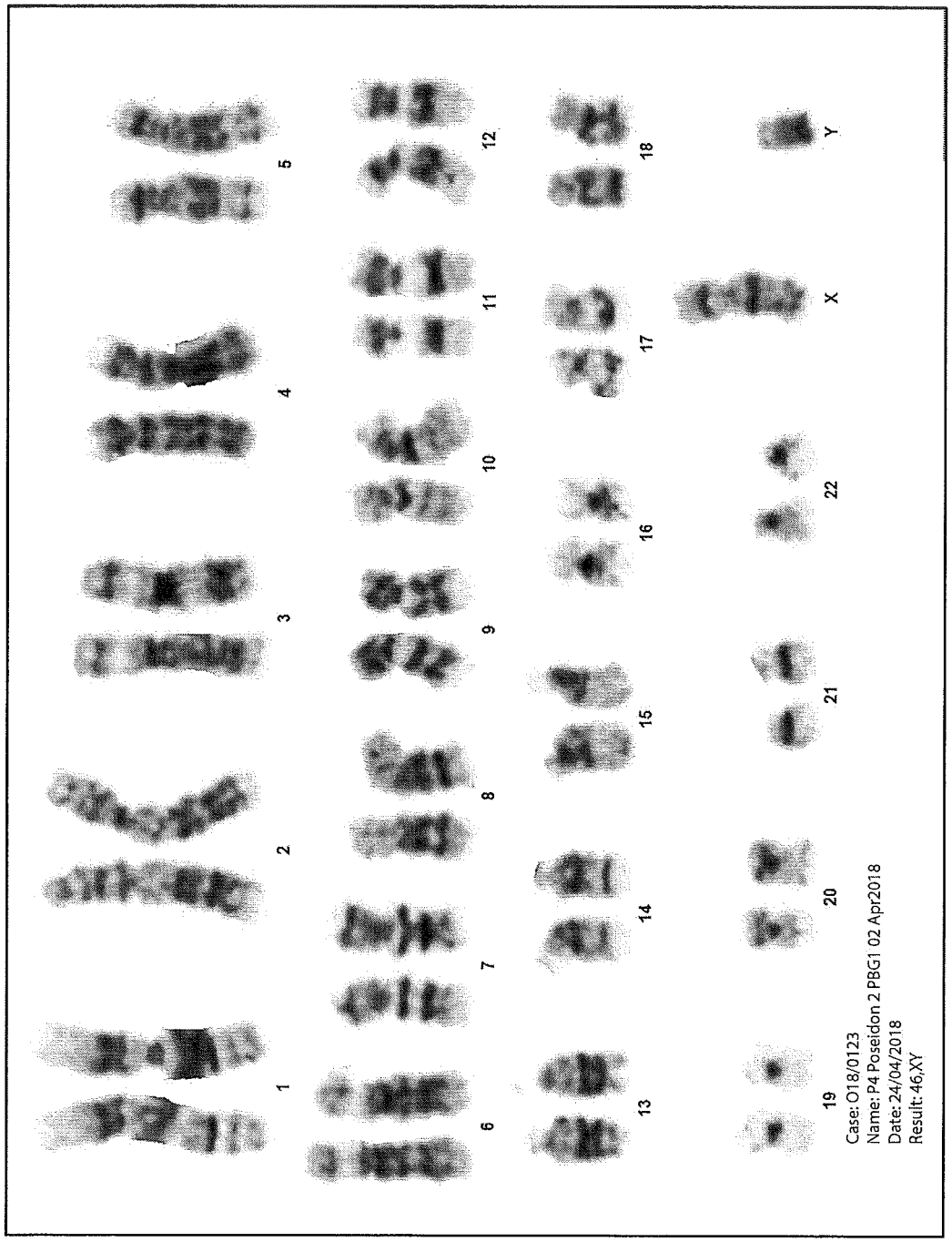
FIG. 14 depicts karyotype analysis of a metaphase chromosome spread from PBG1 iPSCs grown for 4 consecutive 6-7 days expansions in a 3D stir tank, demonstrating normal karyotype after 4 rounds of 3D passaging.

Prior to differentiation, pluripotent PBG-1 expansion is required to produce the large number of cells required for a high-density seed bank, as well as generate sufficient cell numbers to initiate differentiation at an appropriate scale for clinical production. PBG-1 can be maintained and expanded in 2D cultures using recombinant vitronectin (VTN), plus animal component free (ACF), cGMP compatible reagents such as Essential 8, NutriStem, or StemFlex. Characteristic colony growth and maintenance of pluripotency markers were observed for all three growth conditions (FIGS. 9A-9C, FIGS. 10A-10C). To enable large-scale expansion, PBG-1 cells were harvested from 2D cultures as single cells using TrypLE and allowed to self-aggregate in stirred 3D vessels, in this case a 300 ml DasBOX mini bioreactor system. For the first 24 hours, ROCK inhibitor such as Y27632 was added to the cells to promote cell survival during initial aggregation Over 6-7 days in a stir tank, the resulting spheroids increased their diameter from 50 to 250 microns and the overall cell density increased up to 40-fold within that period of time (FIGS. 11A-11C). PBG-1 cells grown in this manner could be passaged repeatedly, and maintained their pluripotency for at least 4 consecutive rounds of expansion (FIGS. 12A-12B, FIG. 13B), and maintained a normal karyotype (FIG. 14).

Figure 16A:
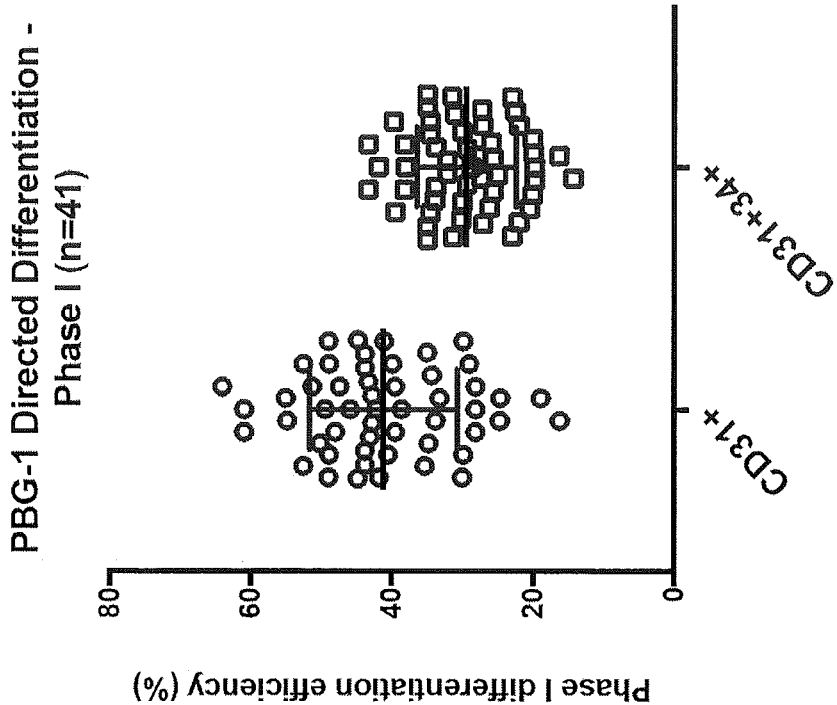
FIG. 16A and FIG. 16B depict representative Phase I differentiation data for PBG1-derived cells.
Figure 16B:
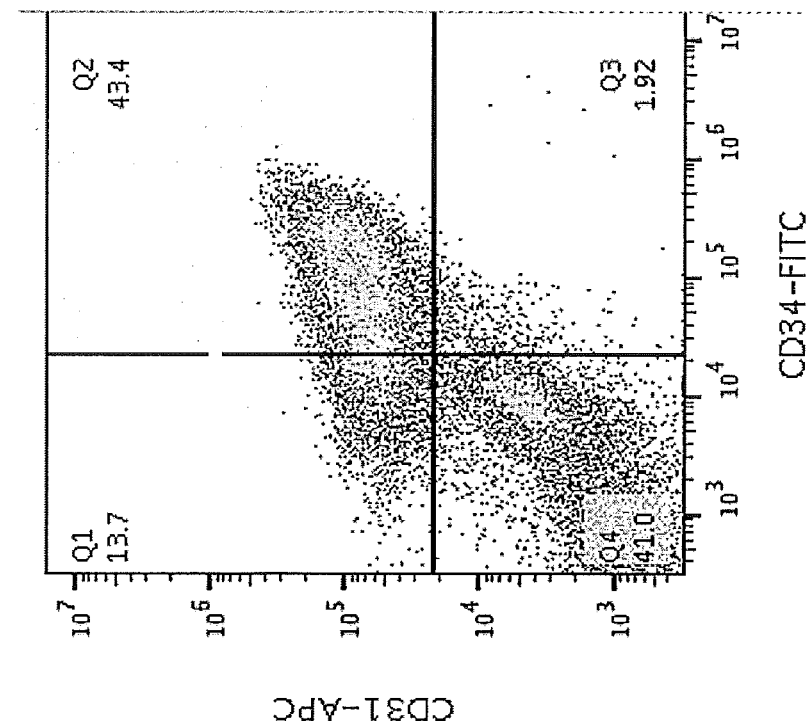

Example 3. In-Depth Characterization of PBG-1 Directed Differentiation to preMKs and MKs Using Collagen IV Matrix in 2D Culture Vessels When harvested with 0.5 mM EDTA and plated as small clumps onto 4.2 ug/cm$^2$ human Collagen IV, PBG-1 cells exhibit a characteristic set of morphological changes through the course of 6 days of Phase I differentiation (FIG. 15). At the end of Phase I, a representative well is harvested as single cells using Accutase and assessed by flow cytometry for the hemogenic endothelial markers CD31 and CD34 (FIG. 16A). Over multiple independent PBG-1 differentiations (n=41), the average day 6 differentiation efficiency was determined to be approximately 40% CD31+(range: ~20-60%) and approximately 30% CD31+CD34+(range ~15%-45%) (FIG. 16B).

Figures 17B, 17C:
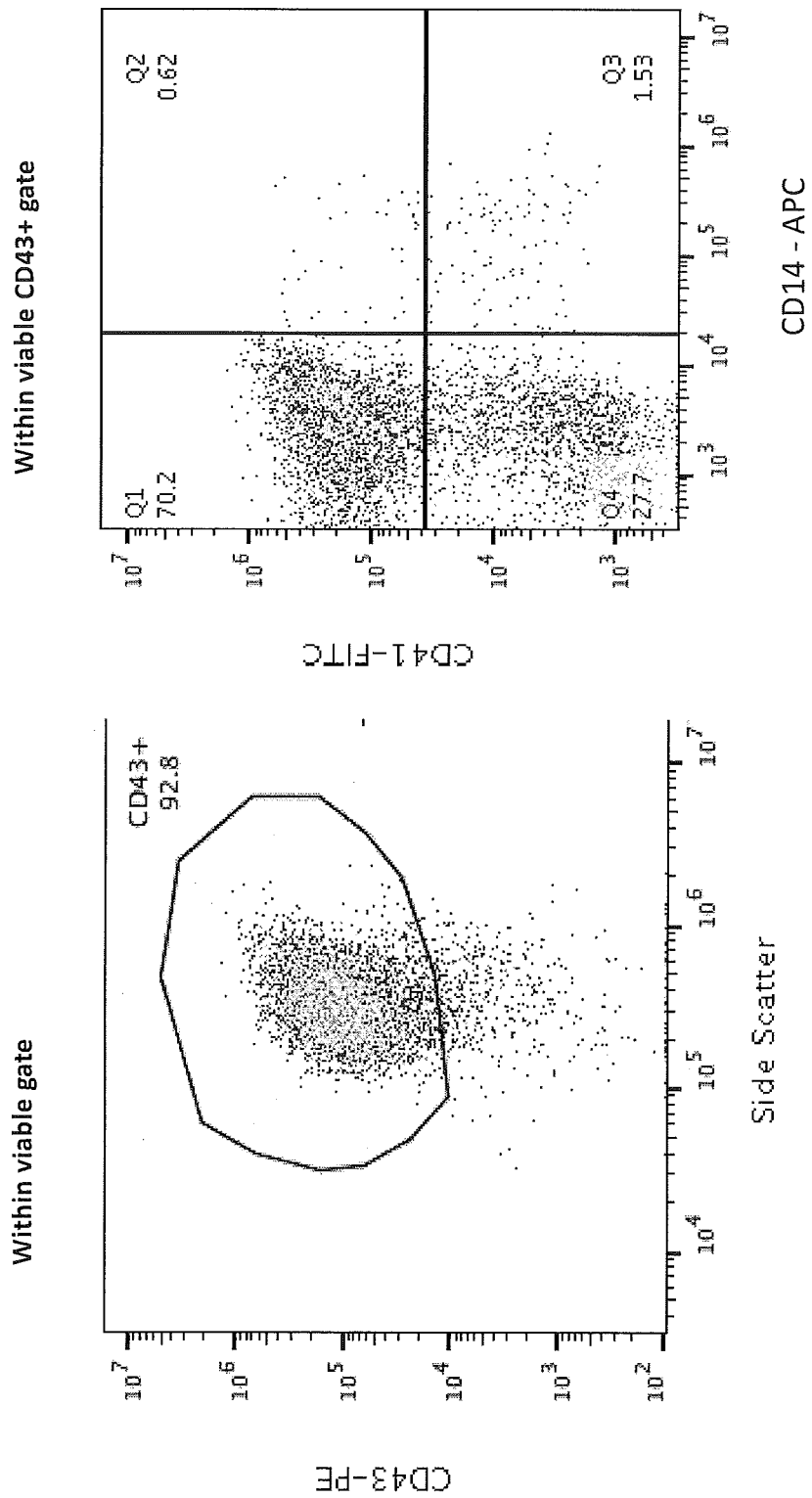
Figure 18B:
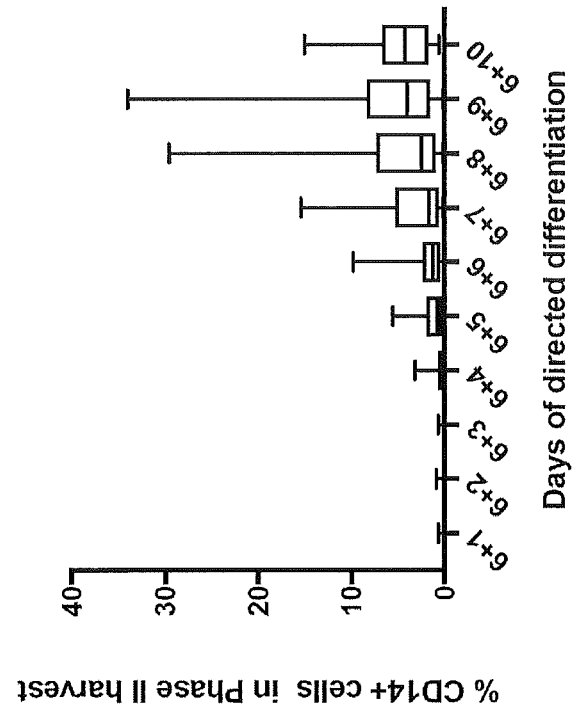
FIG. 18A and FIG. 18B depict average composition characteristics of Phase II suspension cells.
Figure 18A:
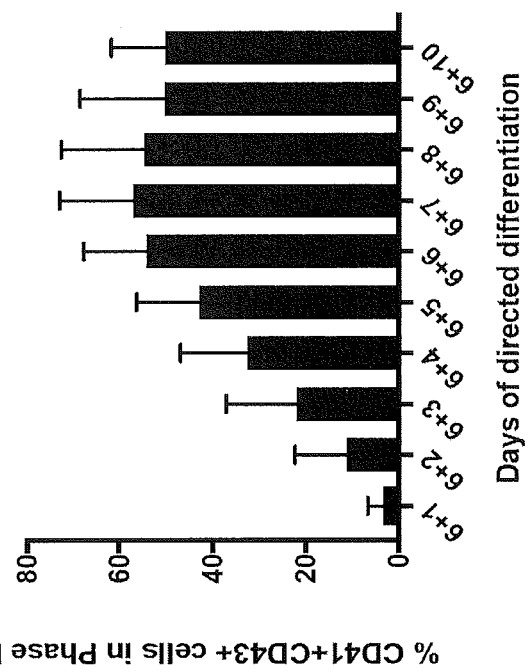
Figure 19B:
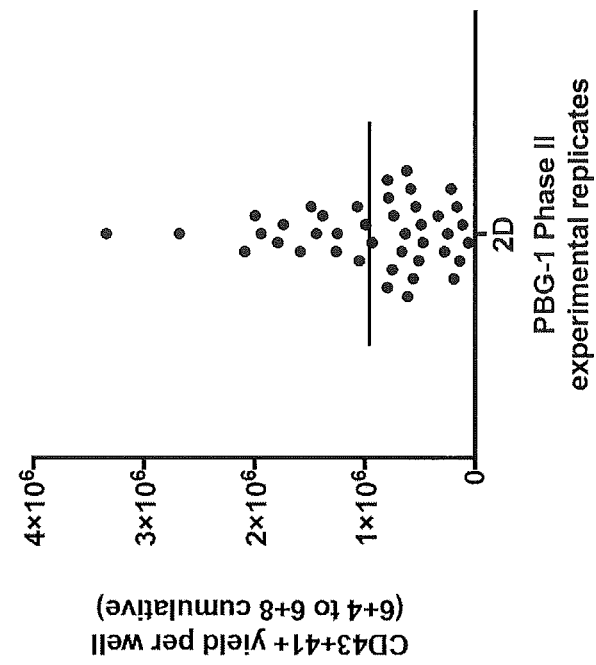
FIG. 19A and FIG. 19B depict yields of released preMKs.
Figure 19A:
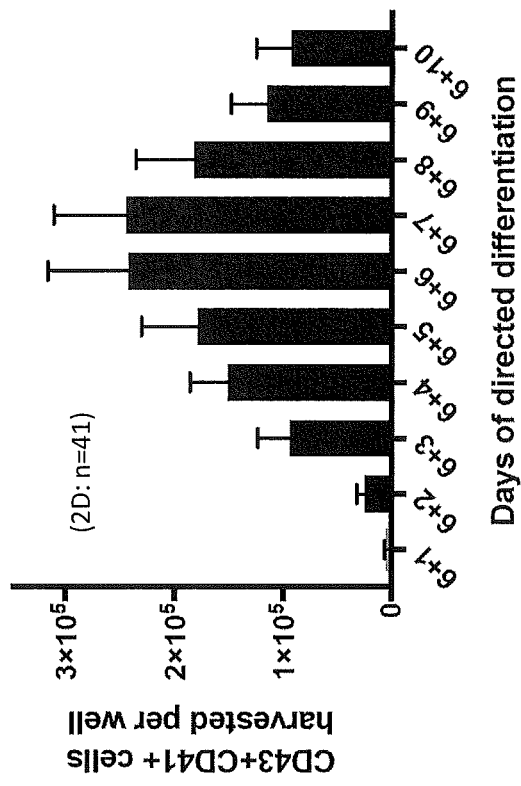

Within 2-3 days after initiation of Phase II (i.e. day 6+2 to 6+3), small, round, refractile cells appear within the adherent hemogenic endothelial cells and are eventually released into the supernatant above the adherent hemogenic endothelial monolayer (FIG. 17A). These released cells contain preMKs, as defined by cell surface expression of CD43 and CD41 and lacking expression of CD14 (FIG. 17B, FIG. 17C). These floating and weakly attached Phase II cells that appear on top of the adherent cell layer are harvested daily by gentle rinsing and collection of the medium into conical tubes, and are analyzed daily for expression of CD43, CD41, and CD14. The purity of the released cells is low for the first several days of Phase II and plateaus thereafter, with an average peak preMK purity of 50-60% by day 6+6 (FIG. 18A). CD14+ myeloid cells are not major contaminants in PBG-1 directed differentiation cultures for the first 6-7 days of Phase II, although there is some variability thereafter (FIG. 18B). The kinetics of preMK production peaks at day 6+6 and 6+7, on average, and decreases thereafter (FIG. 19A). Over multiple independent PBG-1 differentiations (n=41), the average cumulative preMK (CD43+CD41+CD14−) yield was determined to be approximately 1 million per well (range: 0.1 to 3.3 million) (FIG. 19B).

When preMKs from these cultures are transferred to Phase III conditions, they differentiate into mature MKs within several days. Cells that are initially uniformly small, round, and refractile (FIG. 20A) begin to increase in size by day 2-4 (FIG. 20B and FIG. 20C). Simultaneously, proplatelet-producing MKs can be readily observed (FIG. 20C and FIG. 20D). By 3-4 days of Phase III, the proportion of CD61+ (megakaryocytic lineage) cells co-expressing the mature MK markers CD42a and CD42b are determined by FACS (FIG. 21A and FIG. 21B) and the purity of mature MKs (CD61+CD42a+CD42b+ cells) can reach levels as high as 70-90% of all nucleated cells in the culture (FIG. 21C).

Figure 23A:
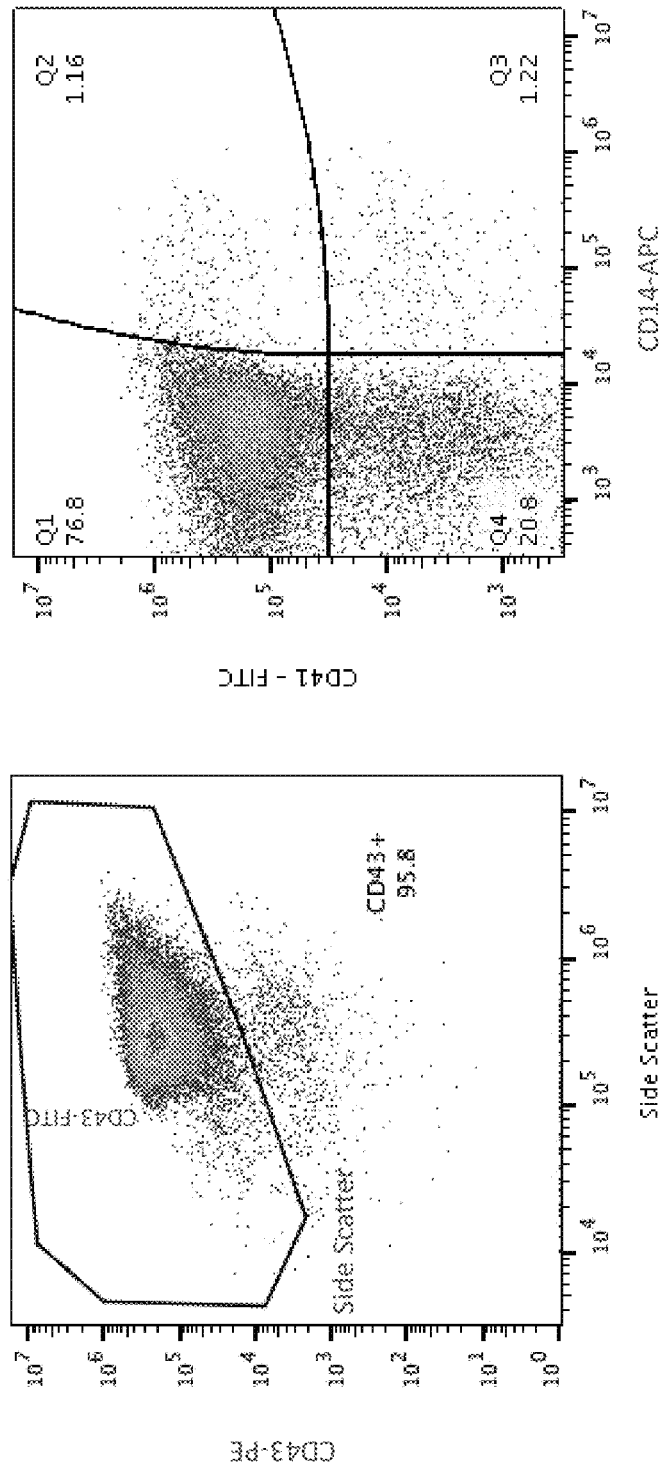
Figure 23B:
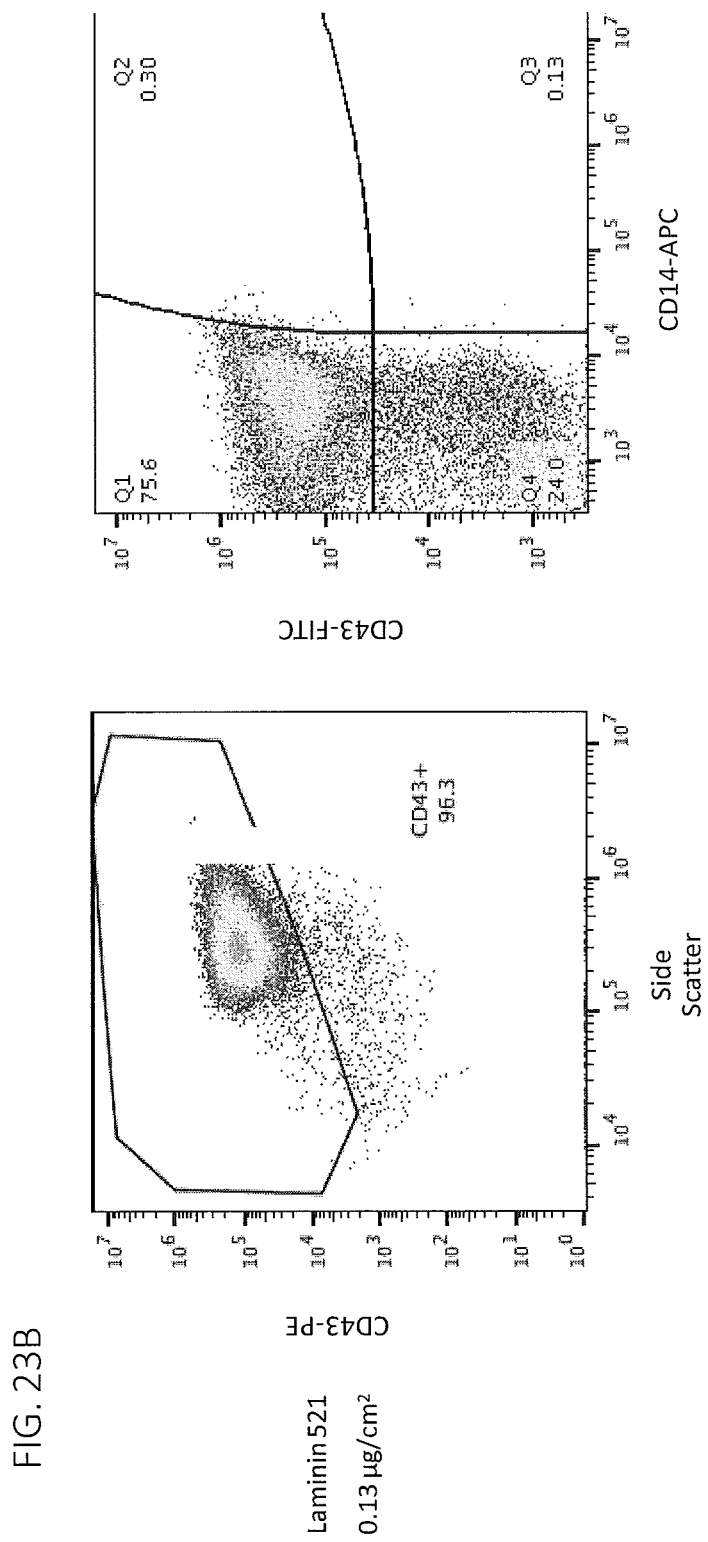
Figure 24B:
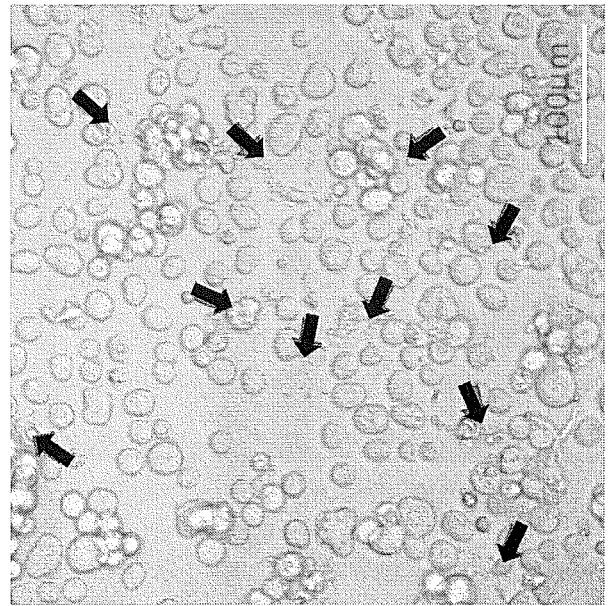
FIG. 24A and FIG. 24B show production of proplatelets from MKs differentiated from preMKs generated from Laminin 521 cultures. Phase III (Day 6+6+3) cultures initiated with preMKs from Collagen IV cultures are shown in FIG. 24A, and Phase III (Day 6+6+3) cultures initiated with preMKs from Laminin 521 cultures are shown in FIG. 24B. Red arrows indicate examples of proplatelets.
Figure 24A:
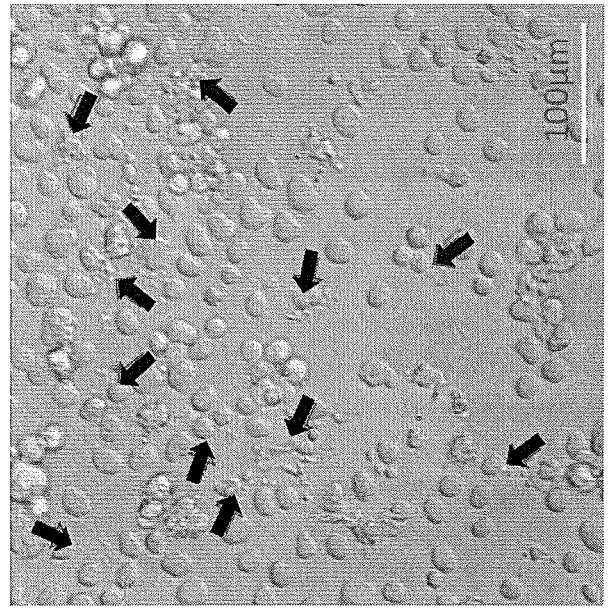
Figure 25A:
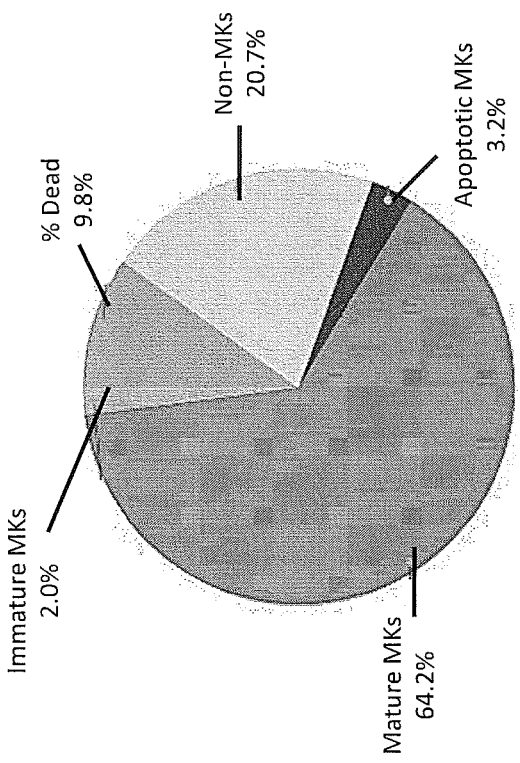
FIG. 25A and FIG. 25B show flow cytometric subset breakdowns of Phase III (Day 6+6+3) cultures.
Figure 25B:
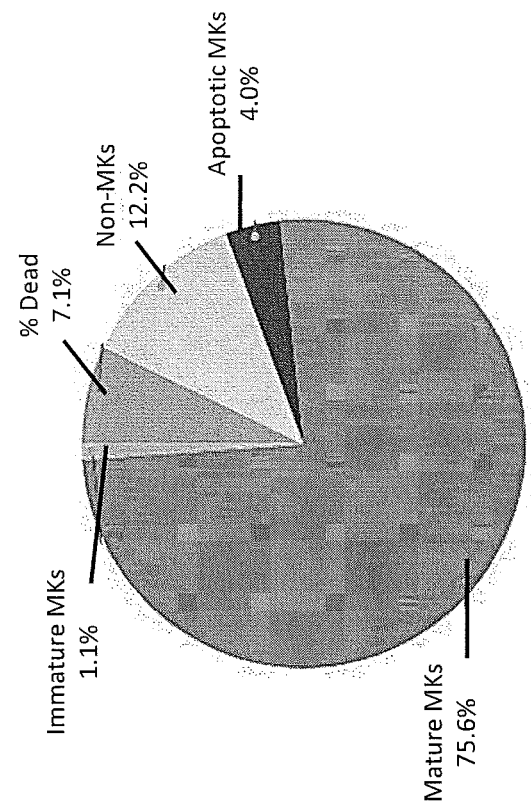

Example 4. Recombinant Laminin521 can Replace Collagen IV to Support Directed Differentiation of PBG-1 into MKs Collagen IV is purified from human placental material and is only available as a Research Use Only reagent. Therefore, Collagen IV is not compatible with cGMP production of PBG-1 derived megakaryocytes, and an alternate strategy must be developed before these cells can be employed for clinical use. One potential solution is to replace the Collagen IV with a recombinant matrix component that is produced from recombinant sources. Here, it is shown that recombinant Laminin-521 can be utilized as a suitable alternative to Collagen IV for directed differentiation of iPSCs to MKs. PBG-1 clumps generated by harvesting with 0.5 mM EDTA exhibited the same characteristic set of morphological changes through the course of 6 days of Phase I differentiation on 0.13 ug/cm² of recombinant Laminin-521 as on 4.2 ug/cm² human Collagen IV (FIGS. 22A-22B). When transitioned to Phase II, the Laminin-521 cultures produced similar yields and purities of preMKs as the corresponding Collagen IV cultures (FIGS. 23A-23C). Upon 3 days of additional differentiation, the cells in Phase III showed similar size, morphology, and propensity for proplatelet production, regardless of whether they were generated on Collagen IV or Laminin-521 (FIGS. 24A-24B). The proportion of CD61+ (megakaryocytic lineage) cells co-expressing the mature MK markers CD42a and CD42b were also measured and found to be similar for cells generated on either matrix (FIGS. 25A-25B).

Example 5. WNT Modulators can Affect Phase I and II Differentiation Efficiency

WNT signaling is important during development The GSK3 kinase inhibitors CHIR98014 and CHIR99021 act as WNT agonists. When the Phase I differentiation conditions described herein (using Laminin 521 matrix) were augmented with 0.6 uM CHIR98014 or 6 uM CHIR99021 for the first 48 hours of differentiation only, a dramatic increase in Phase I differentiation efficiency was observed at day 6, as determined by immunofluorescence staining of CD31 and CD34 (FIGS. 26A-26C). The control and CHIR98014 cultures were then transitioned to Phase II, where the production and release of preMKs were tracked by immunofluorescence staining of CD41 and CD43. Visual estimation of the number of CD41+ cells suggests that the higher Phase I efficiency engendered by WNT modulators in the first 48 hours can correspond to a higher output during Phase II (FIGS. 27A-27B). Therefore, a short period of addition of WNT modulators can impact differentiation efficiency throughout subsequent differentiation phases.

Example 6. Packed Bed Bioreactor with Laminin 521-Coated Macrocarriers

Figure 28:
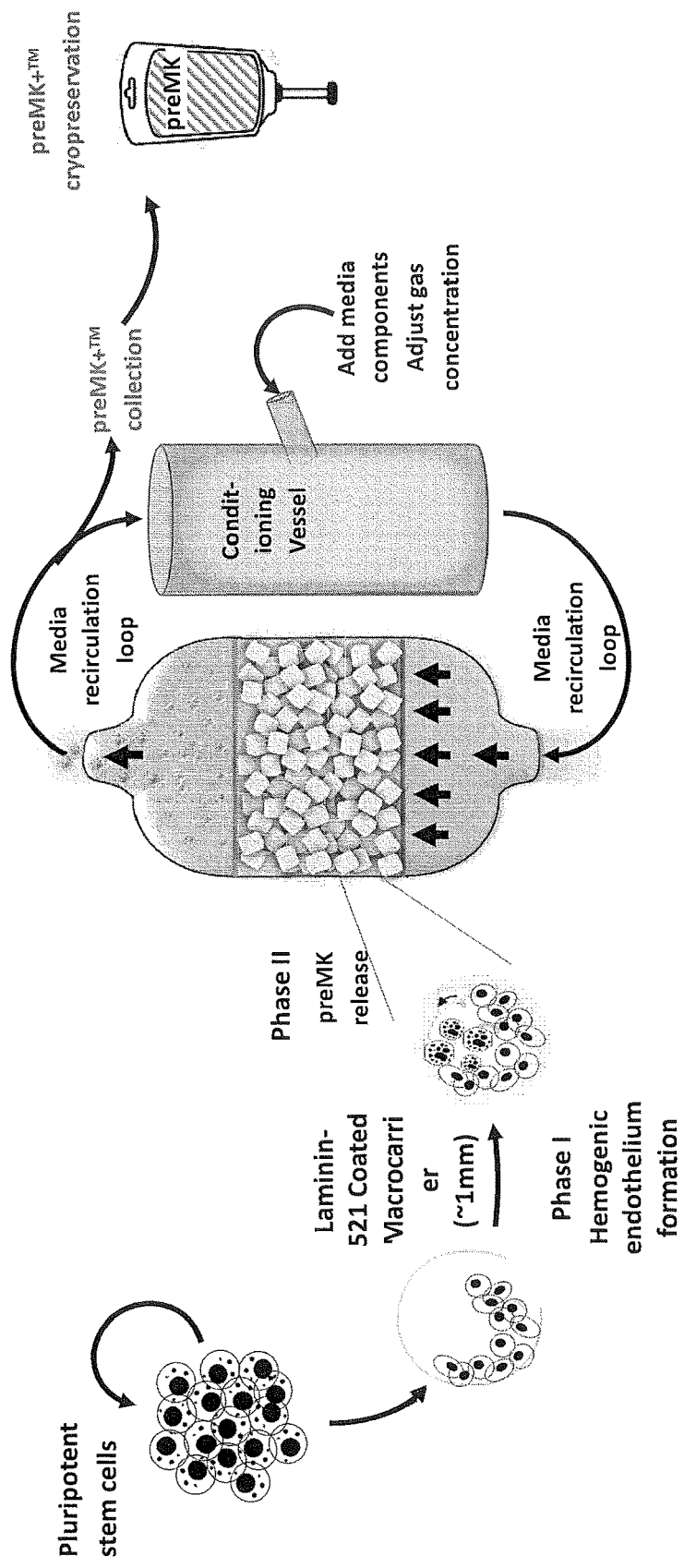
FIG. 28 is a schematic that depicts exemplary directed differentiation protocol of PBG1 into megakaryocytic progenitors using a packed bed bioreactor strategy, a 3D, matrix dependent method. In the embodiment described here, Laminin 521 coated Raschig rings made of PTFE are used as macrocarriers to compose the packed bed.

To enable yields required for clinical production of megakaryocytes and platelets, it is crucial to transition the entire differentiation process from small-scale tissue culture plasticware (2D, matrix dependent) to a 3D scalable solution. Here, we provide evidence that a Laminin 521-coated PTFE macrocarrier in the shape of a 1 mm Raschig ring can provide support for the differentiation of PBG-1 cells and that this macrocarrier material would be amenable for use in a packed bed bioreactor, as illustrated in the schematic (FIG. 28). PTFE rings were first incubated overnight on a rocker at 4° C. with 1.25 ug/ml Laminin-521. Before use, the PTFE rings were equilibrated in a 6-well plate with Essential 8 media plus H1152, a ROCK inhibitor. Pluripotent PBG-1 iPSCs were harvested using 0.5 mM EDTA, resuspended Essential 8 media plus H1152, and seeded as clumps onto the PTFE rings. Every 10 minutes, the plate was run for 30 seconds at 75 rpm on an orbital shaker. After 1 hour, the plate was shaken continuously at 75 rpm overnight. 24 hours later, 90% of the media was removed and replaced with Phase I media, with daily media exchanges. During Phase I, the PBG-1 cells exhibited growth areas on the inside of the Raschig rings (FIG. 29), and the growth areas developed similar morphological characteristics to those seen in 2D cultures (FIG. 22). Flow cytometric analysis of these cells indicated a high proportion of hemogenic endothelial cells, with ~80% of the cells expressing CD31, with more than half of those cells double positive for CD34+(FIG. 31A). Upon switching to Phase II media and initiating half daily media exchanges, the morphology changed from a generally flat colony to a 3D spheroid-type structure, although it should be noted these structures were still attached to the Laminin 521 coating on the inside of the ring-shaped macrocarrier (FIG. 30). Cells that were released during Phase II had a high preMK content even as early as Day 6+2, with ~75% of the cells co-expressing CD43 and CD41 (FIG. 31B), a purity that compares favorably to 2D matrix-dependent cultures (FIG. 18A). Cells released at day 6+3 were collected and cultured for an additional 3 days in Phase III media in an ultra-low-adherent plate, and ~80% of these cells co-expressed CD61 and CD42b (FIG. 31C), indicating that efficient MK differentiation had occurred. Such macrocarriers are amenable for use as material for a packed bed bioreactor in which initial differentiation of iPSCs to hemogenic endothelium (i.e. Phase I of directed differentiation), as well as the further differentiation and release of preMKs (i.e. Phase II of directed differentiation) could occur in the same vessel (FIG. 28). In this design, a packed bed bioreactor is set up with Laminin-521 coated macrocarriers freshly seeded with pluripotent PBG-1 iPSCs. The packed bed is then exposed to a continuous flow of media to enable Phase I differentiation to hemogenic endothelium. After percolating through the packed bed, the media would be circulated through a conditioning chamber, where fresh media components would be added, and oxygen/$CO_2$ concentrations would be adjusted via sparging or other means before the media would be recirculated to the cells. At the completion of Phase I, the media would be switched to allow Phase II differentiation and production and release of preMKs. Appropriately sized and shaped macrocarrier substrates such as the 1 mm Raschig rings would enable sufficient media flow and channel width to enable the released cells to percolate through the packed bed and out of the reactor for collection and cryostorage. This design decreases the shear forces experienced by the cells, allows for efficient media usage due to its perfusion based design, and enables the continuous collection of preMKs as they are released.

Figure 34B:
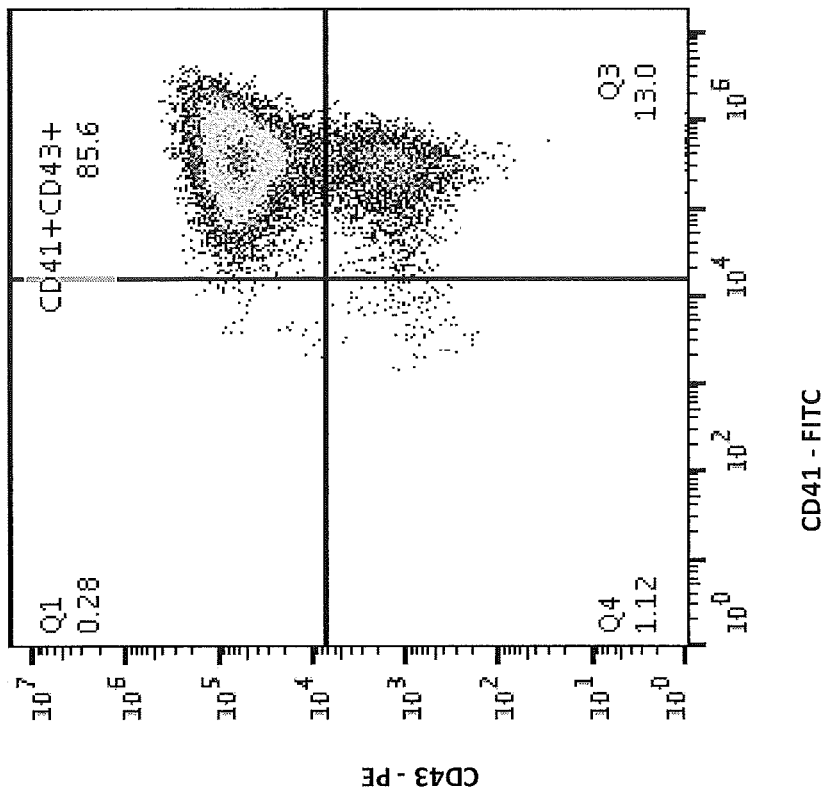
FIG. 34A, FIG. 34B, FIG. 34C, and FIG. 34D describe Phase II in a directed differentiation initiated with self-aggregating spheroids of PBG1 iPSCs.
Figure 34A:
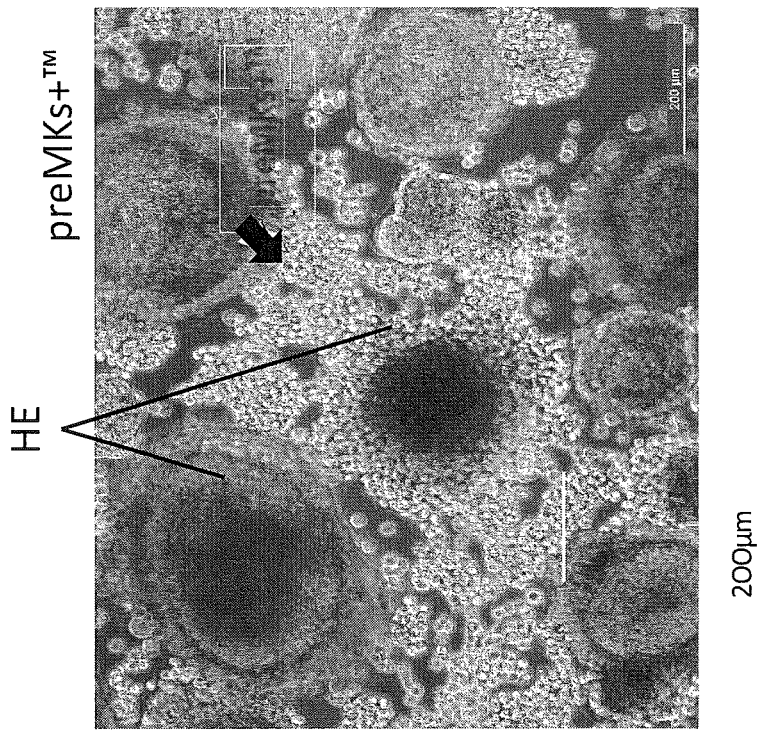
Figure 34C:
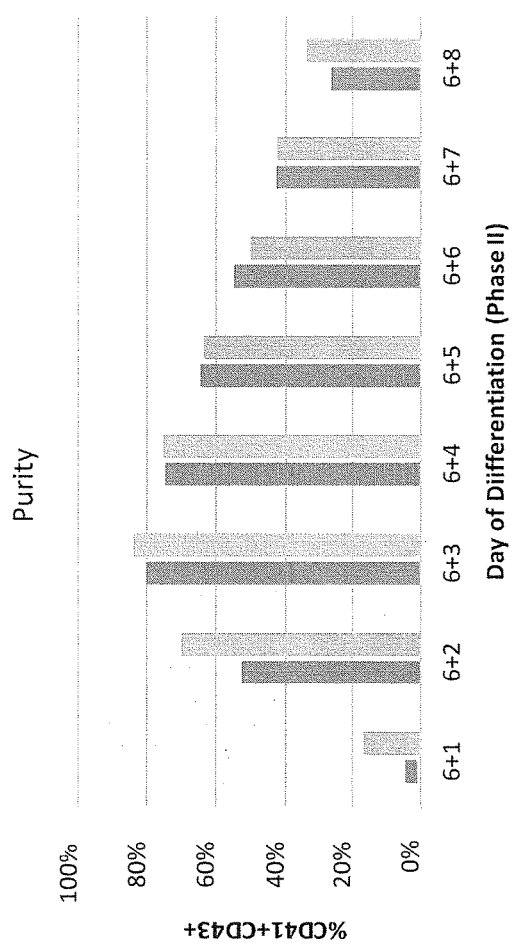
Figure 34D:
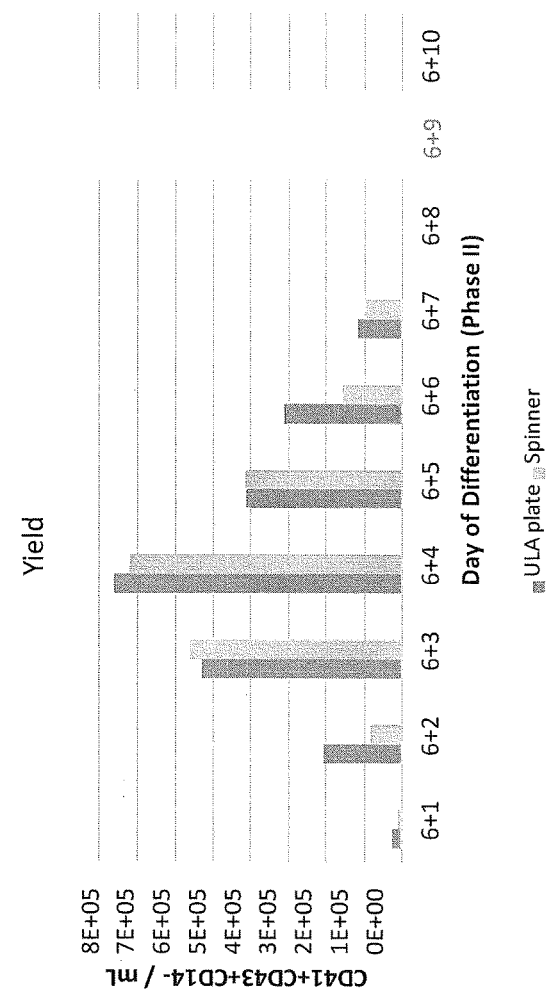
Figure 35A:
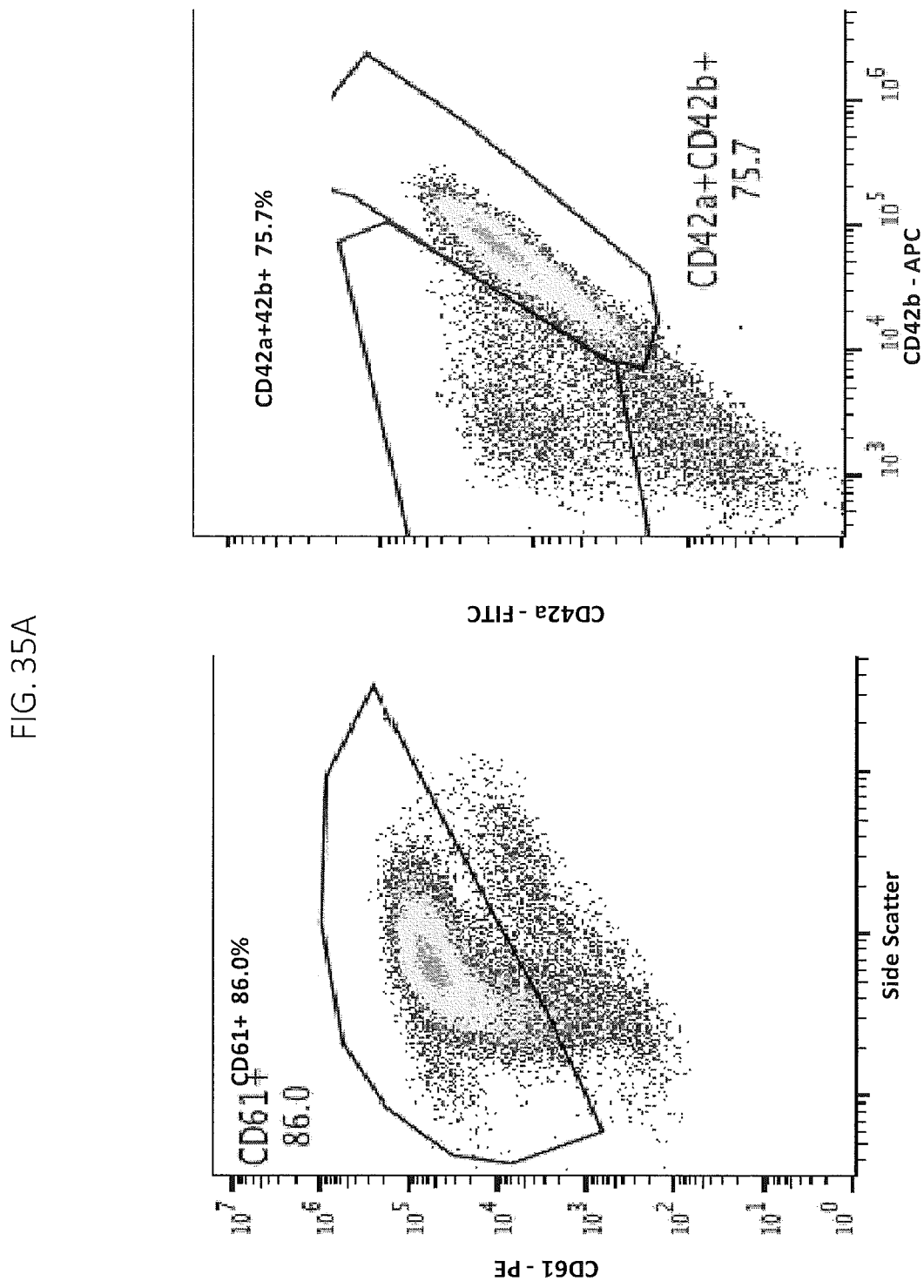
FIG. 35A, FIG. 35B, and FIG. 35C depict Phase III MK differentiation from 3D, matrix-independent cultures initiated from self-aggregating spheroids of PBG1 iPSCs.
Figure 35C:
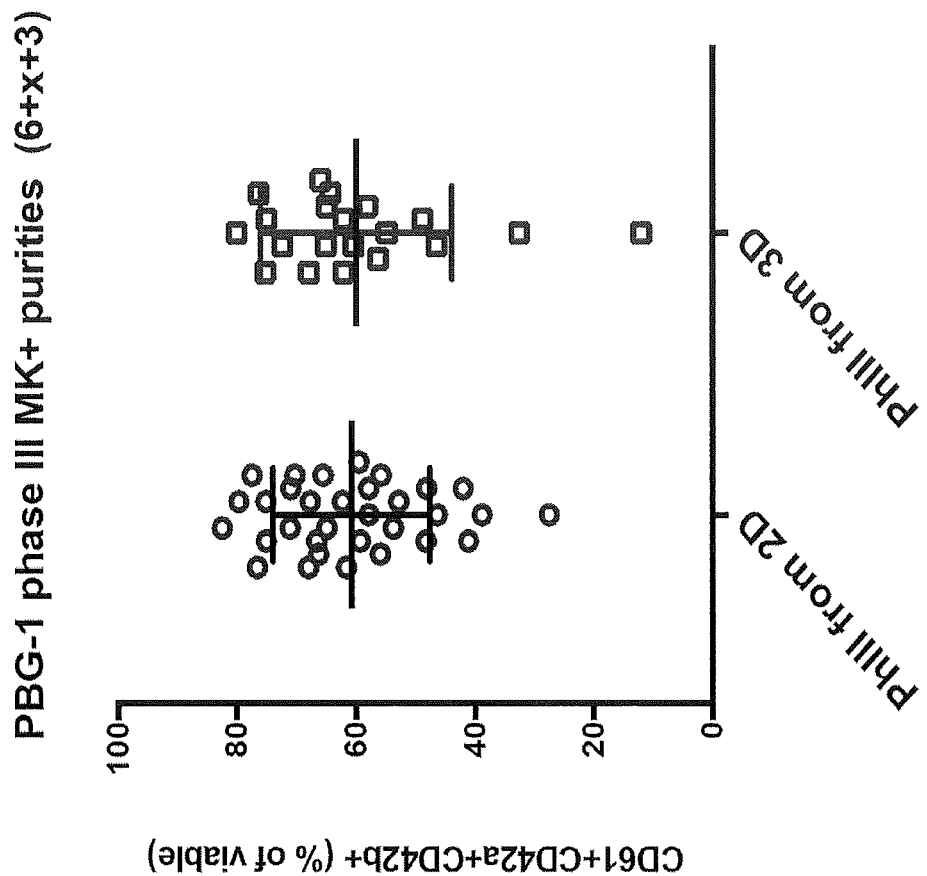
Figure 35B:
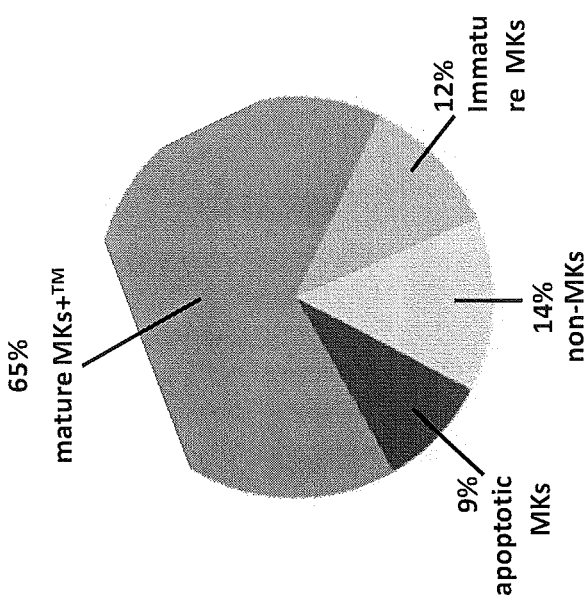
Figure 37:
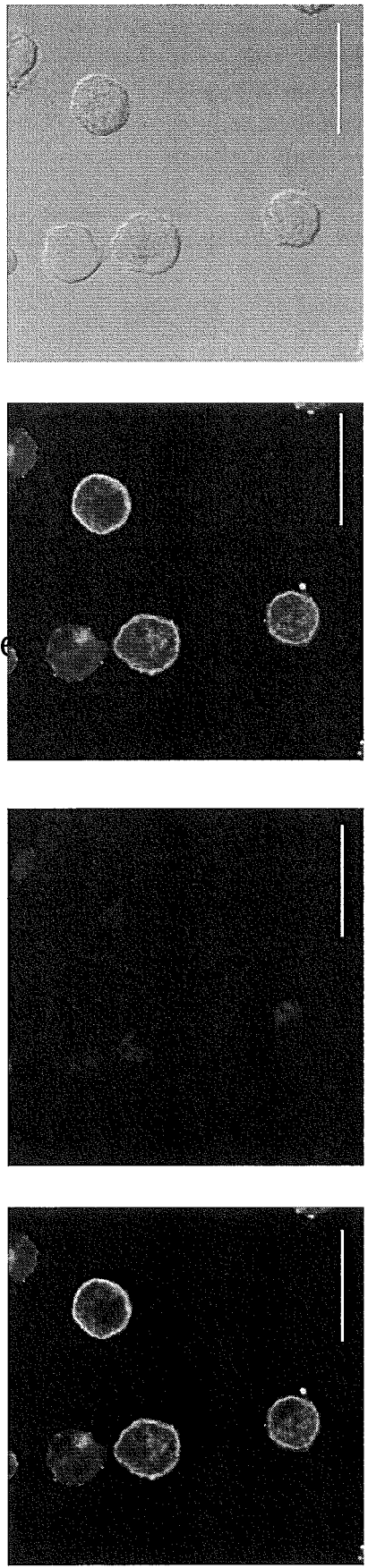
FIG. 37 depicts PBG1-derived megakaryocytes immunostained for the megakaryocyte-specific protein β1-tubulin. Simultaneously, nuclei were visualized by nucleic acid staining.
Figure 40A:
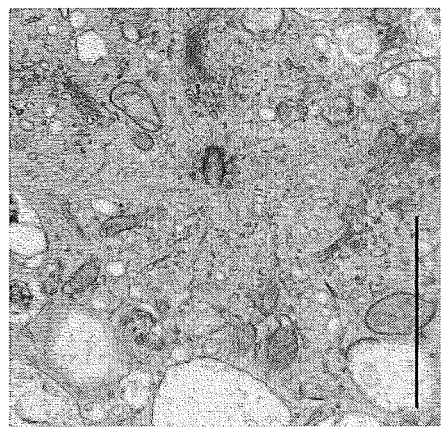
FIG. 40A, FIG. 40B, FIG. 40C and FIG. 40D are electron microscopy images showing a PBG1-derived megakaryocyte.
Figure 40B:
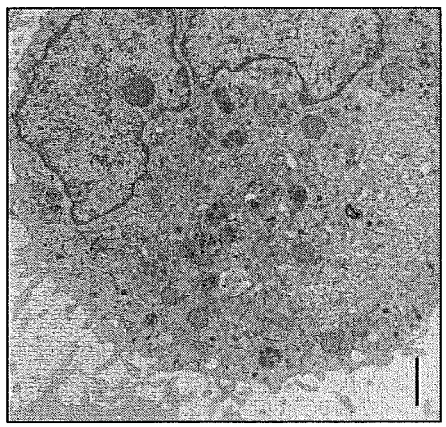
Figure 40C:
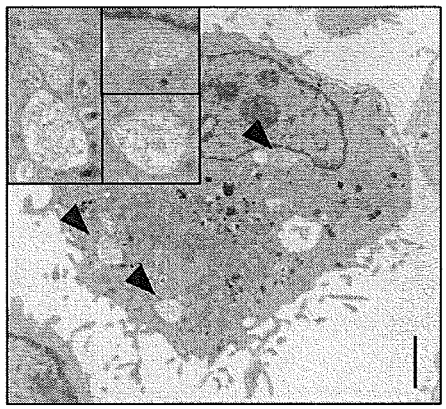
Figure 40D:
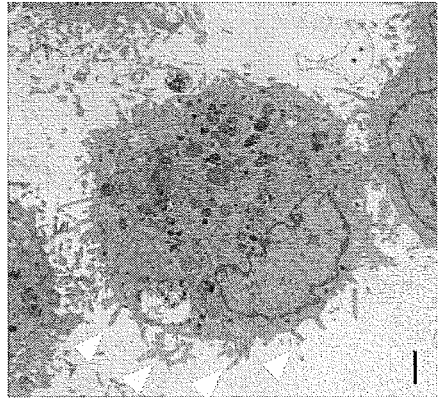

Example 7. Self-Aggregating iPSC-Derived Spheroids in a Stir Tank Bioreactor Another example of a scalable 3D solution involves performing differentiations using self-aggregating spheroids suspended in stirred or shaken ultra-low-adherent vessels (FIG. 32). In this example, pluripotent PBG-1 iPSCs were dissociated into single cells using TrypLE, resuspended at 0.5-1 million cells/ml in pluripotency maintenance media (such as Essential 8, Nutristem, StemFlex, other similar media, or combinations thereof) plus H1152 or other ROCK inhibitor, and incubated at 37 C, 5% CO2, 20% O2 in a 6-well ultra low adherent plate on an orbital shaker at 90 rpm, or a spinner flask with constant agitation (90 rpm for 50 ml volume in a 125 ml spinner flask). Within 24 hours in either system, the PBG-1 cells self-aggregated to form spheroids approximately 50-150 um in diameter (FIG. 33A, also see FIG. 11A for similar example in a different vessel). Agitation was then paused, and the spheroids were allowed to settle to the bottom of the vessel (approximately 5 minutes). 50%-100% of the media was then exchanged with Phase I differentiation media to promote the differentiation towards hemogenic endothelium, and agitation was resumed, with incubation in hypoxic conditions (37 C, 5% CO2, 5% O2). Media exchanges were similarly performed on a daily basis for a total of 6 days (4 days in 37 C, 5% CO2, 5% O2, followed by 2 days in 37 C, 5% CO2, 20% O2), during which time the spheroids grew larger and developed characteristic structure and shape by day 6 (FIG. 33A). When a sample of these spheroids at day 6 were dissociated and assessed by flow cytometry, ~44% of the cells were found to express the hemogenic endothelial markers CD31 and CD34 (FIG. 33B), a purity that compared favorably to 2D matrix-dependent cultures (FIG. 16B). To transition to Phase II, agitation was paused and the spheroids were allowed to settle to the bottom of the vessel (approximately 5 minutes). 50-100% of the media was then exchanged with Phase II differentiation media to promote the differentiation and release of suspension cells (FIG. 34A). On a daily basis thereafter, suspension cells were collected and a partial media exchange was performed. To do this, agitation was paused and the hemogenic endothelial spheroids were allowed to settle to the bottom of the vessel (approximately 5 minutes). Approximately 80% of the media (together with the suspension cells) was collected, and centrifuged. Half the working volume of fresh Phase II differentiation media was added to the spheroids, along with a sufficient volume of conditioned media (i.e. supernatant post-centrifugation) to restore the original working volume. The remaining supernatant was then discarded, with a portion of the cell pellet used for FACS analysis (FIG. 34B), and the remainder cryopreserved or transferred to Phase III for maturation to mature MKs. Flow cytometric analysis of the suspension cells revealed that the majority of the cells released between days 6+2 and 6+6 co-expressed the preMK markers CD43 and CD41 (FIG. 34B, FIG. 34C). Overall preMK purities and yields from 3D self-aggregating spheroid cultures (FIG. 34C, FIG. 34D) compared favorably to purities and yields from 2D cultures (FIG. 18A, FIG. 19A). Upon transition to static Phase III cultures, preMKs from 3D self-aggregating spheroid cultures generated similar MK purities as preMKs from 2D culture systems (FIGS. 35A-35C). Furthermore, Phase III differentiation cultures generated from 3D self-aggregating spheroid cultures contained cells that increased dramatically in size and were able to generate proplatelets (FIG. 36), consistent with their identity as bona fide megakaryocytes.

Example 8. Detailed Characterization of PBG1 iPSC-Derived Megakaryocytes

Figure 41C:
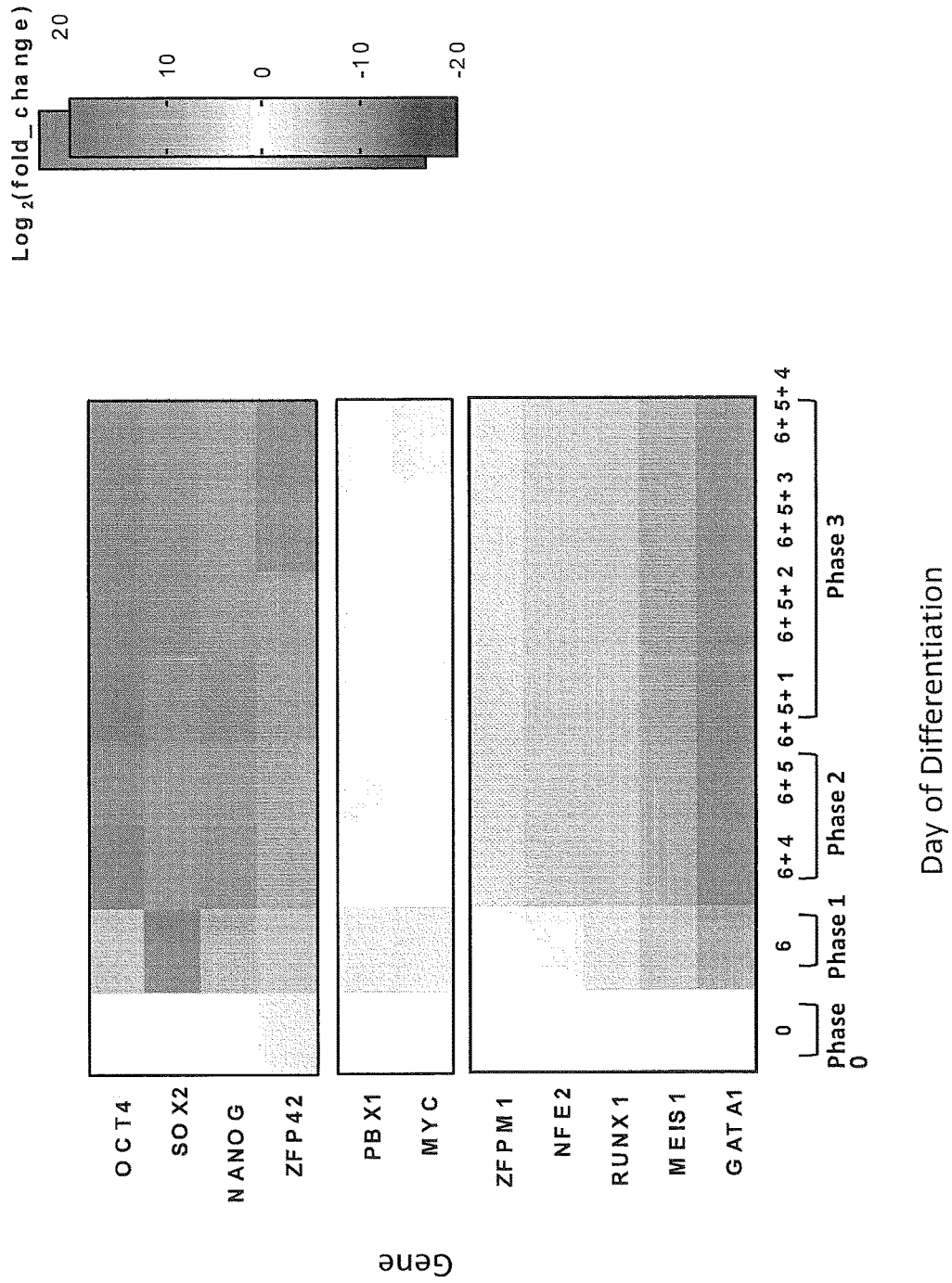

Megakaryocytes generated using the methods described herein demonstrate many features associated with functional mature MKs, including when imaged by immunofluorescence microscopy for the MK-specific protein beta-1-tubulin (FIG. 37), as well as proteins associated with alpha-granules (PF4 and VWF, FIGS. 38A-38F) and dense granules (LAMP1 and serotonin, FIGS. 39A-39F). Electron microscopy images of PBG1-derived MKs reveal characteristic ultrastructural features, including multivesicular bodies, glycogen granules, and an invaginated membrane system (FIGS. 40A-40D). Gene expression analysis revealed the downregulation of pluripotency genes such as OCT4 (FIG. 41A) and upregulation of megakaryocyte lineage genes, such as NFE2 (FIG. 41B). Similar analyses were performed on a panel of relevant genes, and the results of this analysis are consistent with the loss of a pluripotent stem cell signature and the acquisition of a megakaryocyte signature (FIG. 41C).

Figure 43B:
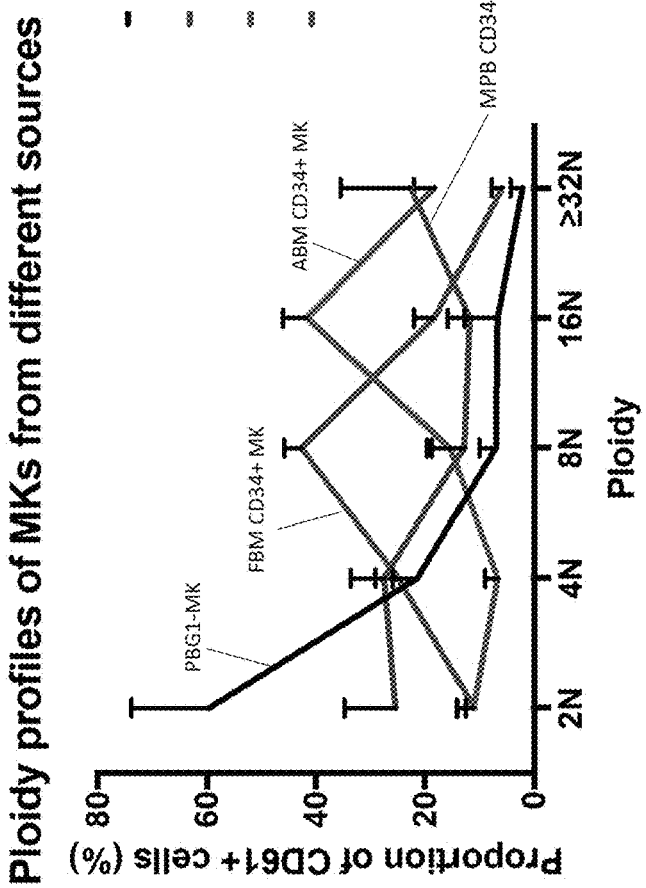
FIG. 43A and FIG. 43B provide ploidy measurements on PBG1 derived megakaryocytes.
Figure 43A:
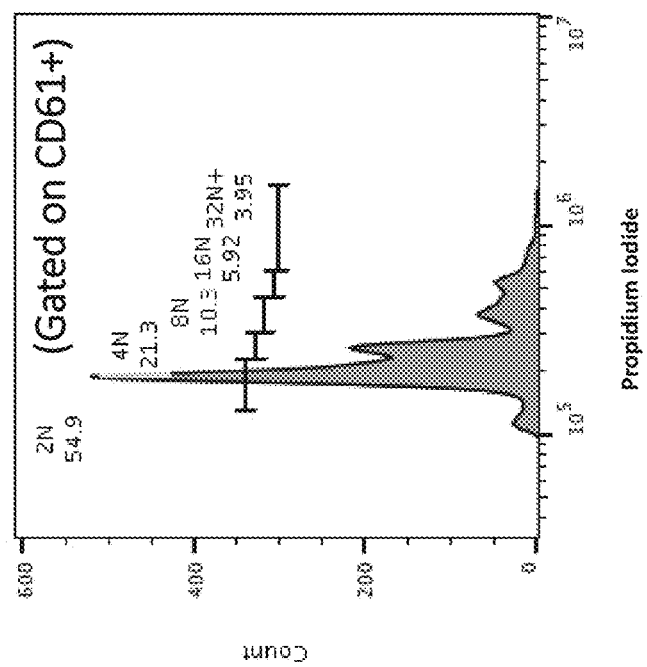

When compared to primary megakaryocytes (natural product) derived from bone marrow CD34$^+$, peripheral blood CD34$^+$, or cord-blood CD34$^+$ cells, PBG1-derived MKs, it was found that PBG1 iPSC– derived MKs had a similar average size (FIGS. 42A-42C), yet a characteristic lower ploidy distribution (FIGS. 43A-43B), compared to primary megakaryocytes (natural product) derived from CD34$^+$ bone marrow, peripheral blood, or cord-blood stem cells (FIG. 42C, FIG. 43B). PBG1 hiPSC derived megakaryocytes also had a characteristic growth factor, cytokine, and chemokine expression profile of factors similar to that present in human platelets, including the presence of multiple factors not previously reported in megakaryocytes (FIG. 44). To prepare the data, hiPSC-MK at 25 million/mL in 1×PBS were lysed by freezing the cells at −80° C. overnight and then thawed at 37° C. This freeze/thaw cycle was repeated 4 times. The resulting suspension was filtered using a 0.22 μm syringe filter. Lysates were tested for a select panel of growth factors, cytokines, and chemokines using multiplexing laser bead technology (Eve Technologies). Data was corrected for background (PBS, which was processed similarly as hiPSC-MK), then compared to commercially available human platelet lysate (HPL), fresh MK differentiation media (used in the final stage of differentiation), and Conditioned Media, i.e. MK differentiation media removed from hiPSC-MK before lysis. While a strong overlap was observed between hiPSC-MK and HPL, there were also several proteins measured in hiPSC-MK that were not previously described in megakaryocytes or platelets (as indicated by " ").

Figure 45A:
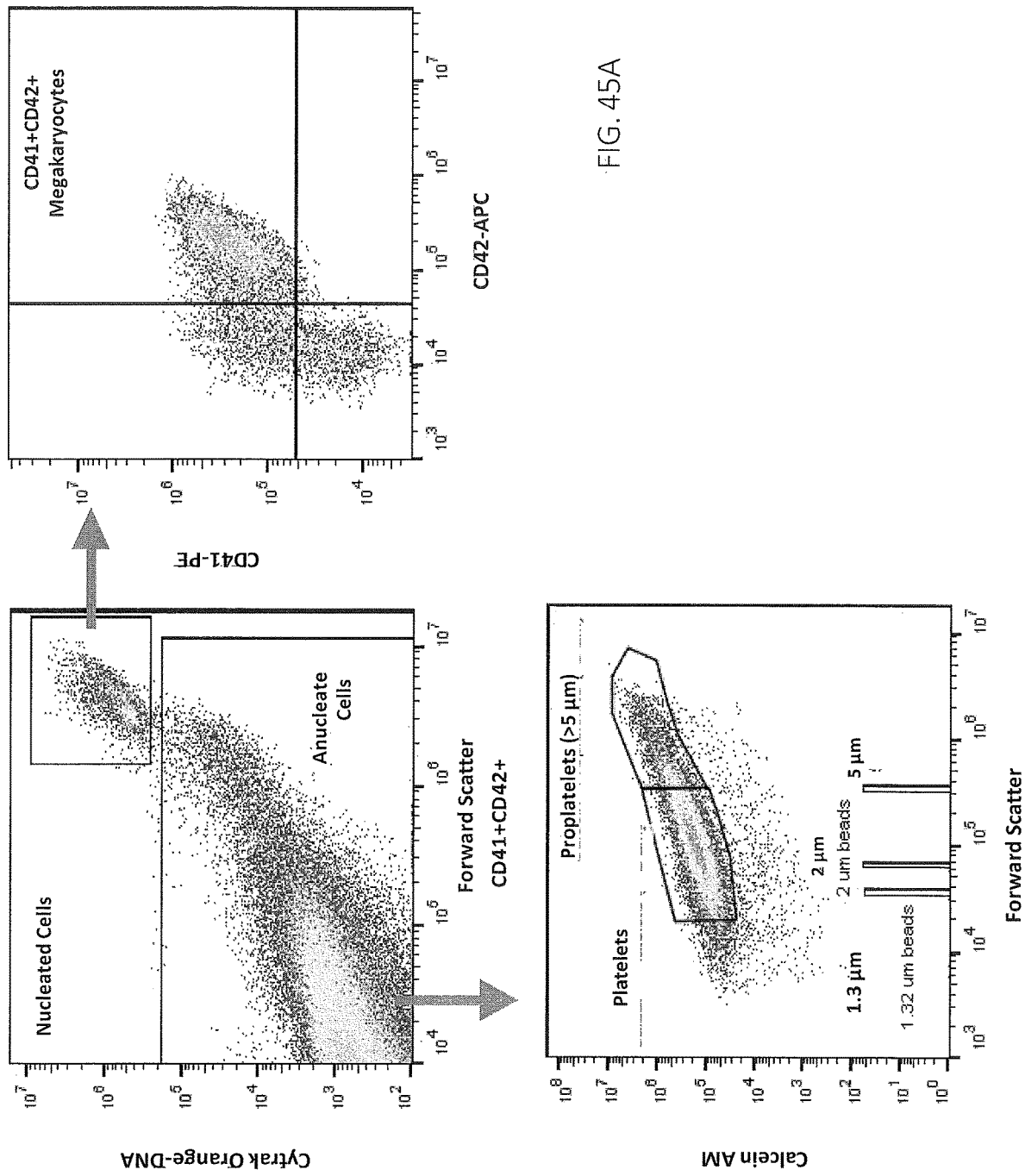
FIG. 45A, FIG. 45B, and FIG. 45C depict hiPSC platelet production.
Figure 45C:
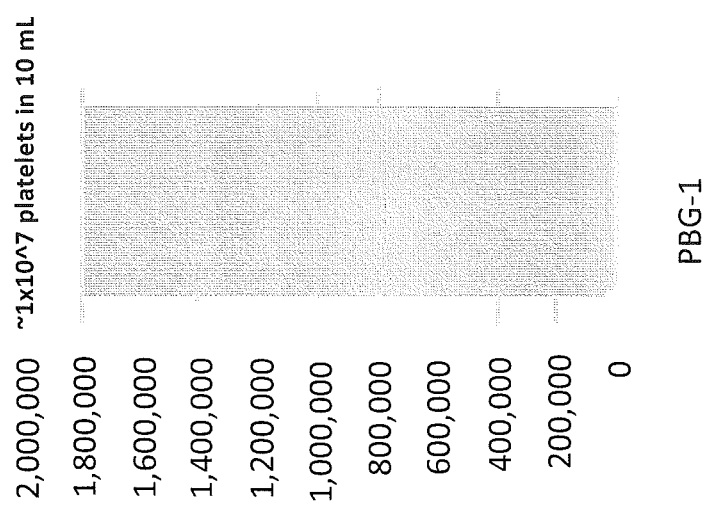
Figure 45B:
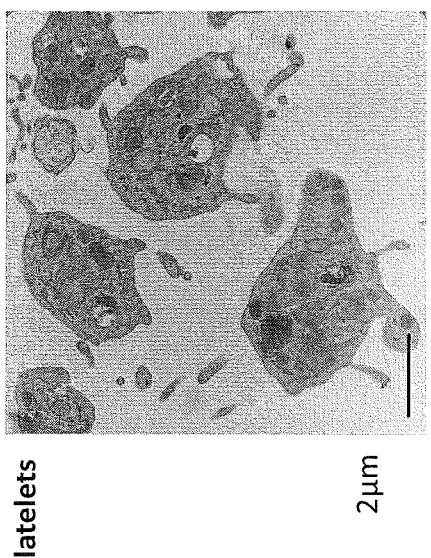

The results described herein demonstrate a robust process for generating clinical grade human iPSC-derived megakaryocytes. Human iPSC-derived megakaryocytes can be isolated and concentrated for further characterization or use in downstream applications, such as the generation of human platelets (FIGS. 45A-45C).

OTHER EMBODIMENTS

As described herein, the present disclosure features compositions and methods for producing megakaryocytic progenitors and megakaryocytes. In one aspect, the disclosure provides a megakaryocyte or megakaryocytic progenitor differentiated from a clinical grade hiPSC cell or cell line. In some embodiments, the present disclosure provides an isolated population of cells comprising the megakaryocyte or megakaryocytic progenitor according to any aspect delineated herein. In some embodiments, the present disclosure provides a composition comprising a megakaryocyte or megakaryocytic progenitor according to any aspect delineated herein.

In some embodiments, the disclosure provides a composition or pharmaceutical composition comprising a lysate of a megakaryocyte according to any aspect delineated herein. In some embodiments, the disclosure provides a composition or pharmaceutical composition comprising a lysate of a platelet generated from the megakaryocyte according to any aspect delineated herein. In some embodiments, the disclosure provides a method of producing a megakaryocyte, the method comprising differentiating a clinical grade hiPSC cell or cell line. In various embodiments of any aspect delineated herein, the megakaryocyte is one or more of $CD42b^+$, $CD61^+$, and $DNA^+$. In various embodiments of any aspect delineated herein, the megakaryocyte has a diameter of about 10-30 µm. In certain embodiments, the megakaryocyte has a diameter of about 10-20 µm. In various embodiments of any aspect delineated herein, the megakaryocyte has a ploidy of at least 4N, 8N, or 16N. In various embodiments of any aspect delineated herein, the megakaryocytic progenitor is $CD14^-$, $CD41^+$, and $CD43^+$. In various embodiments of any aspect delineated herein, the megakaryocytic progenitor is capable of continuously being produced to at least day 10 after initiation of differentiation from a hemo-endothelial progenitor (i.e., Phase II, Day 6+10). In various embodiments of any aspect delineated herein, the megakaryocytic progenitor is capable of continuously being produced to at least day 17 after initiation of differentiation from a hemo-endothelial progenitor (i.e., Phase II, Day 6+17). In various embodiments of any aspect delineated herein, the clinical grade hiPSC cell or cell line is selected from the group consisting of PBG1, PBG2, and PBG3.

In various embodiments of any aspect delineated herein, the isolated population of cells or the composition contains a platelet generated from a megakaryocyte of the disclosure. In various embodiments of any aspect delineated herein, the isolated population of cells or the composition contains at least 50% $CD42b^+$ of $CD41^+CD61^+$ cells. In various embodiments of any aspect delineated herein, the isolated population of cells or the composition contains at least 50% megakaryocytes having ploidy of 4N or greater. In certain embodiments, at least 50% megakaryocytes have ploidy 4N-16N. In various embodiments of any aspect delineated herein, the isolated population of cells or composition contains megakaryocytes having a mean ploidy of 4N or greater.

From the foregoing description, it will be apparent that variations and modifications may be made to the disclosure described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method for megakaryocyte production comprising:
    culturing dissociated pluripotent stem cells in a matrix-independent culture and under continuous agitation such that the pluripotent stem cells form self-aggregating pluripotent cell spheroids;
    differentiating, under continuous agitation, the self-aggregating pluripotent cell spheroids in a first culture medium into hemogenic endothelial cell spheroids; and
    differentiating, under continuous agitation, the hemogenic endothelial cell spheroids in a second culture medium to produce megakaryocytic progenitors, causing the hemogenic endothelial cell spheroids to release the megakaryocytic progenitors into suspension while maintaining the hemogenic endothelial cell spheroids for subsequent production and release of the megakaryocytic progenitors.

2. The method of claim 1 wherein the first culture medium comprises one or more of Bone morphogenic protein 4 (BMP4), Basic fibroblast growth factor (bFGF), and Vascular endothelial growth factor (VEGF).

3. The method of claim 1 wherein the second culture medium comprises one or more of Stem cell factor (SCF), Thrombopoietin (TPO), Fms-related tyrosine kinase 3 ligand (Flt3-L), Interleukin-3 (IL-3), Interleukin-6 (IL-6) and Heparin.

4. The method of claim 1 wherein the pluripotent stem cells are human induced pluripotent stem cells.

5. The method of claim 1 further comprising the step of seeding the megakaryocytic progenitors onto a non-adherent surface in a culture medium before differentiating the megakaryocytic progenitors into megakaryocytes.

6. The method of claim 1 further comprising the step of differentiating the megakaryocytic progenitors in a third culture medium into megakaryocytes.

7. The method of claim 6 wherein the third culture medium comprises one or more of Stem cell factor (SCF), Thrombopoietin (TPO), Interleukin-6 (IL-6), Interleukin-9 (IL-9) and Heparin.

8. A method for megakaryocyte production comprising:
    differentiating, in a matrix-independent culture, pluripotent stem cells in a first culture medium into hemogenic endothelial cells; and
    differentiating the hemogenic endothelial cells in a second culture medium into megakaryocytic progenitors,
    wherein each of the differentiating the pluripotent stem cells and the differentiating the hemogenic endothelial cells is carried out under continuous agitation to enable the pluripotent stem cells to self-aggregate and differentiate into hemogenic endothelial cell spheroids and the hemogenic endothelial cells in the hemogenic endothelial cell spheroids to differentiate into megakaryocyte progenitors, causing the hemogenic endothelial cell spheroids to release the megakaryocytic progenitors into suspension while maintaining the hemogenic endothelial cell spheroids for subsequent production and release of additional megakaryocytic progenitors.

9. The method of claim 8 wherein the first culture medium comprises one or more of Bone morphogenic protein 4 (BMP4), Basic fibroblast growth factor (bFGF), and Vascular endothelial growth factor (VEGF) and the second culture medium comprises one or more of Stem cell factor (SCF), Thrombopoietin (TPO), Fms-related tyrosine kinase 3 ligand (Flt3-L), Interleukin-e (IL-3), Interleukin-6 (IL-6) and Heparin.

10. The method of claim 8 wherein the pluripotent stem cells are human induced pluripotent stem cells.

11. The method of claim 8 further comprising the step of differentiating the megakaryocytic progenitors in a third culture medium into megakaryocytes, the third culture medium comprising one or more of Stem cell factor (SCF), Thrombopoietin (TPO), Interleukin-6 (IL-6), Interleukin-9 (IL-9) and Heparin.

* * * * *